(12) United States Patent
Nagai et al.

(10) Patent No.: US 12,410,157 B2
(45) Date of Patent: Sep. 9, 2025

(54) COMPOUND USEFUL AS TOLL-LIKE RECEPTOR 7 ACTIVATION INHIBITOR

(71) Applicants: TOYAMA PREFECTURAL UNIVERSITY, Toyama (JP); TEIKA PHARMACEUTICAL CO., LTD., Toyama (JP); NATIONAL INSTITUTE OF ADVANCED INDUSTRIAL SCIENCE AND TECHNOLOGY, Tokyo (JP)

(72) Inventors: Yoshinori Nagai, Toyama (JP); Naoki Okamoto, Toyama (JP); Shigeto Fujishita, Toyama (JP); Takatsugu Hirokawa, Tokyo (JP)

(73) Assignees: TOYAMA PREFECTURAL UNIVERSITY, Toyama (JP); TEIKA PHARMACEUTICAL CO., LTD., Toyama (JP); NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 510 days.

(21) Appl. No.: 18/008,871

(22) PCT Filed: Jun. 7, 2021

(86) PCT No.: PCT/JP2021/021564
§ 371 (c)(1),
(2) Date: Dec. 7, 2022

(87) PCT Pub. No.: WO2021/251337
PCT Pub. Date: Dec. 16, 2021

(65) Prior Publication Data
US 2023/0234944 A1    Jul. 27, 2023

(30) Foreign Application Priority Data

Jun. 8, 2020 (JP) ................................ 2020-099708

(51) Int. Cl.
| | | |
|---|---|---|
| C07D 405/10 | (2006.01) |
| A61P 37/06 | (2006.01) |
| C07C 33/38 | (2006.01) |
| C07C 43/178 | (2006.01) |
| C07C 43/23 | (2006.01) |
| C07C 57/48 | (2006.01) |
| C07C 69/757 | (2006.01) |
| C07C 219/22 | (2006.01) |
| C07C 219/30 | (2006.01) |
| C07C 311/04 | (2006.01) |
| C07D 205/04 | (2006.01) |
| C07D 211/38 | (2006.01) |
| C07D 295/096 | (2006.01) |
| C07D 295/185 | (2006.01) |
| C07D 307/94 | (2006.01) |

(52) U.S. Cl.
CPC ............ *C07D 405/10* (2013.01); *A61P 37/06* (2018.01); *C07C 33/38* (2013.01); *C07C 43/1788* (2013.01); *C07C 43/23* (2013.01); *C07C 57/48* (2013.01); *C07C 69/757* (2013.01); *C07C 219/22* (2013.01); *C07C 219/30* (2013.01); *C07C 311/04* (2013.01); *C07D 205/04* (2013.01); *C07D 211/38* (2013.01); *C07D 295/096* (2013.01); *C07D 295/185* (2013.01); *C07D 307/94* (2013.01)

(58) Field of Classification Search
CPC ..... C07D 405/10; C07D 205/04; A61P 37/06; C07C 33/38; C07C 43/1788; C07C 43/23; C07C 57/48; C07C 69/757; C07C 219/22; C07C 219/30; C07C 31/94
See application file for complete search history.

(56) References Cited

U.S. PATENT DOCUMENTS

| | | |
|---|---|---|
| 2007/0149597 A1 | 6/2007 | Nishi et al. |
| 2010/0008900 A1 | 1/2010 | Chan et al. |

FOREIGN PATENT DOCUMENTS

| | | |
|---|---|---|
| JP | 2006-063068 A | 3/2006 |
| WO | WO-2015/169994 A1 | 11/2015 |
| WO | WO-2017/047769 A1 | 3/2017 |

OTHER PUBLICATIONS

Christensen et al., "Toll-like receptor 7 and TLR9 dictate autoantibody specificity and have opposing inflammatory and regulatory roles in a murine model of lupus," Immunity. 25(3):417-28 (2006).
Deane et al., "Control of toll-like receptor 7 expression is essential to restrict autoimmunity and dendritic cell proliferation," Immunity. 27(5):801-10 (2007).
Fukui et al., "Unc93B1 restricts systemic lethal inflammation by orchestrating toll-like receptor 7 and 9 trafficking," Immunity. 35:69-81 (2011).
International Search Report mailed Aug. 3, 2021, for International Application No. PCT/JP2021/021564, Nagai et al., "Novel Compound Useful as Toll-Like Receptor 7 Activation Inhibitor," filed Jun. 7, 2021 (4 pages).

(Continued)

*Primary Examiner* — Timothy R Rozof
(74) *Attorney, Agent, or Firm* — Clark & Elbing LLP

(57) ABSTRACT

CB-7 exhibits a weak TLR7 inhibiting effect in normal mice. The present invention provides a novel compound with a stronger TLR7 inhibiting effect than CB-7, a pharmaceutically acceptable salt of said compound, or a prodrug of said compound or salt. The present invention also provides a drug for the prevention or treatment of diseases associated with the activation of TLR7, said drug including the aforementioned TLR7 activation inhibitor.

10 Claims, 16 Drawing Sheets

Specification includes a Sequence Listing.

(56) References Cited

OTHER PUBLICATIONS

Kawashima et al., "Synthesis of cyclobakuchiols A, B, and C by using conformation-controlled stereoselective reactions," Chemistry. 20(1):272-8 Supplemental material (2014) (40 pages).

Komatsuda et al., Up-regulated expression of Toll-like receptors mRNAs in peripheral blood mononuclear cells from patients with systemic lupus erythematosus, Clin Exp Immunol. 152(3):482-7 (2008).

Kumar et al., "Regulation of B cell tolerance by the lupus susceptibility gene Ly108," Science. 312(5780):1665-9 (2006).

Lehmann et al., "An unconventional role for miRNA: let-7 activates Toll-like receptor 7 and causes neurodegeneration," Nat Neurosci. 15(6):827-35 (2012).

Römmler et al., "Guanine modification of inhibitory oligonucleotides potentiates their suppressive function," J Immunol. 191(6):3240-53 (2013) supplemental material. (24 pages).

Office Action dated Jun. 5, 2024, for Chinese Patent Application No. 202180038262.5, Nagai et al., "Novel Compounds for Use as Inhibitors of Activation," filed Jun. 7, 2021 (English translation) (13 pages).

Saline #1
(BUN 64.0 mg/dL, Cr 0.41 mg/dL)

Wire loop lesion    Crescent formation

B2-24-4-5A·HCOOH #1
(BUN 18.0 mg/dL, Cr 0.10 mg/dL)

Fig. 13 (A) Helper T cell; Fig. 13 (B) Cytotoxic T cell; Fig. 13 (C) Activated T cell; Fig. 13 (D) Naive T cell; Fig. 13 (E) Memory T cell

SEQUENCE LISTING

```
<160> NUMBER OF SEQ ID NOS: 4

<210> SEQ ID NO 1
<211> LENGTH: 22
<212> TYPE: RNA
<213> ORGANISM: artificial
<220> FEATURE:
<223> OTHER INFORMATION: microRNA

<400> SEQUENCE: 1
uagcuuauca gacugauguu ga                                    22

<210> SEQ ID NO 2
<211> LENGTH: 23
```

```
<212> TYPE: RNA
<213> ORGANISM: artificial
<220> FEATURE:
<223> OTHER INFORMATION: microRNA

<400> SEQUENCE: 2
ugagugugug ugugugagug ugu                                    23

<210> SEQ ID NO 3
<211> LENGTH: 22
<212> TYPE: RNA
<213> ORGANISM: artificial
<220> FEATURE:
<223> OTHER INFORMATION: microRNA

<400> SEQUENCE: 3
ugagguagua gguugugugg uu                                     22

<210> SEQ ID NO 4
<211> LENGTH: 20
<212> TYPE: RNA
<213> ORGANISM: artificial
<220> FEATURE:
<223> OTHER INFORMATION: microRNA

<400> SEQUENCE: 4
gcccgucugu ugugugacuc                                        20
```

COMPOUND USEFUL AS TOLL-LIKE RECEPTOR 7 ACTIVATION INHIBITOR

SEQUENCE LISTING

The instant application contains a Sequence Listing which has been submitted electronically in ASCII format and is hereby incorporated by reference in its entirety. Said ASCII copy, created on Dec. 7, 2022, is named 51007-027001_Sequence_Listing_12_7_22_ST25 and is 1,148 bytes in size.

TECHNICAL FIELD

This invention relates to novel compounds useful as a Toll-like receptor 7 (TLR7) activation inhibitor and a drug for prevention or treatment of a disease involving TLR7 activation containing the activation inhibitor.

BACKGROUND ART

Immune system can be broadly classified into innate immune system and acquired immune system. The innate immune system is a defense mechanism that operates in an early stage of infection, in which phagocytic cells such as dendritic cells and macrophages play a central role. On the other hand, the acquired immune system is an acquired defense mechanism to deal with myriad antigens, in which lymphocytes play a central role. The acquired immunity is initiated when T cells, which are a type of lymphocyte, receive antigens from activated dendritic cells. In other words, activation of the innate immunity is essential for induction of the acquired immunity.

TLRs expressed within phagocytic cells or on the plasma membrane thereof specifically recognize bacterial and viral components and induce the production of inflammatory cytokines by activating transcription factors such as NF-κB. For example, TLR7 localizes to endosomes and lysosomes of B cells and plasmacytoid dendritic cells and recognizes virus-derived single-stranded RNA. When TLR7 recognizes a ligand, TLR7 induces the production of type I interferon (IFN-α) to protect against viral infection. Since TLR7 also recognizes nucleic acids (autoantigens) released from damaged or dead cells of the self, IFN-α is one of the factors associated with the onset and exacerbation of non-infectious inflammatory diseases such as autoimmune diseases. When classical dendritic cells are differentiation-induced from monocytes by IFN-α, the classical dendritic cells are activated upon uptake of dead cells and promote proliferation and differentiation of autoreactive T cells through antigen presentation. IFN-α also promotes class-switching in autoreactive B cells and differentiation into plasma cells by inducing expression of BAFF (B cell activating factor) or APRIL (a proliferation inducing ligand) in dendritic cells. As a result, autoantibody production in living organism is stimulated, and immune complexes composed of nucleic acids and the autoantibodies stimulate plasmacytoid dendritic cells to promote IFN-α production. This chronicity of IFN-α production leads to progression and exacerbation of the disease.

The autoimmune diseases are a group of disorders characterized by appearance of antibodies against self-antigens (e.g., antinuclear antibodies), which are often accompanied by various characteristic inflammations. As the disease progresses, the autoimmune diseases cause severe damage to various organs, including multiple organs such as skin and kidneys, muscles, nerves, and blood vessels. Systemic lupus erythematosus is a typical example of autoimmune disease caused by abnormal TLR7 signaling and IFN-α production. The number of patients with systemic lupus erythematosus is estimated to be 1.4 million worldwide and 100,000 in Japan (the number of patients with systemic lupus erythematosus who were issued a specific disease medical care beneficiary certificate in 2016 was 63,792), and the disease is particularly prevalent among women in their 20s and 30s. Systemic lupus erythematosus is an intractable immunological disease of unknown cause, and is designated as a specific disease by the Ministry of Health, Labour and Welfare. Kumar, K. R., et al. suggests that in a mouse model of systemic lupus erythematosus (BXSB), translocation of a region containing TLR7 gene which is originally localized to the X chromosome is responsible for pathogenesis of the disease (Kumar, K. R., et al. Science. 312:1665-1669, 2006). TLR7 transgenic mice develop systemic lupus erythematosus-like glomerulonephritis and about half die by 20 weeks of age (Deane, J. A., et al. Immunity. 27:801-810, 2007). Mice in which the 34th aspartic acid residue in Unc93B1 involved in the transport of TLR7 or TLR9 from the endoplasmic reticulum to endosomes is mutated to an alanine residue develop autoimmune-like symptoms due to increased TLR7 responsiveness and more than half die within a year due to hepatitis (Fukui, R., et al. Immunity. 35:69-81, 2011). Human patients with systemic lupus erythematosus have higher TLR7 gene expression in peripheral blood mononuclear cells than healthy individuals, and produce large amounts of proinflammatory cytokines upon TLR7 ligand stimulation (Komatsuda, A., et al. Clin Exp Immunol. 152: 482-487, 152: 482-487, 2008). Deletion of TLR7 in mouse models of autoimmune diseases is also known to ameliorate the pathology. MRL/Mp$^{lpr/lpr}$ mouse, which is a spontaneous autoimmune disease model and a representative animal model of human systemic lupus erythematosus, produces autoantibodies such as antinuclear antibodies and develops vasculitis, polyarthritis, and glomerulonephritis with aging. The deletion of TLR7 in the MRL/Mp$^{lpr/lpr}$ mice suppresses lymphocyte activation and reduces symptoms of nephritis (Christensen, S. R., et al. 2006. Immunity. 25(3):417-428). In contrast, the deletion of TLR9 in MRL/Mp$^{lpr/lpr}$ mice reduced anti-DNA antibody titers but did not improve symptoms of nephritis.

Many problems still remain in the treatment of autoimmune diseases. Rheumatoid arthritis, which is the most common autoimmune disease, is an inflammatory disease that primarily affects the synovial membrane of joints, and an autoimmune disease that causes persistent polyarthritis, cartilage and bone damage, and progressive joint destruction. The involvement of inflammatory cytokines in autoimmune diseases has been analyzed mainly in mouse models of rheumatoid arthritis and rheumatoid arthritis patients. IL-1 receptor antagonists as IL-1 inhibitors, anti-TNF-α antibodies as TNF-α inhibitors, and anti-IL-6 receptor antibodies as IL-6 inhibitors have been approved and used in practice for the treatment of rheumatoid arthritis, and all of them are more effective than conventional standard drug therapy. In addition, biologics, including antibody drugs, are expected to be useful to systemic lupus erythematosus. In fact, a recombinant human IgG1 lambda monoclonal antibody against the B-cell activator B lymphocyte stimulator (BLyS) (trade name: belimumab) has been shown to be effective in treating some patients with systemic lupus erythematosus because of its ability to suppress the proliferation of autoreactive B cells which are involved in the exacerbation of the disease, and has been marketed in Japan and overseas. For example, in EU, it is approved as an adjunctive or concomitant therapy for the treatment of adult patients with autoantibody-positive systemic lupus erythematosus whose disease activity is high despite standard treatment. It is also indicated in U.S. for the treatment of the patients, but its efficacy in patients with severe active lupus nephritis or central nervous system lupus has not yet been clinically evaluated and is of limited prescription. In a phase III trial in Northeast Asia, including Japan, announced in November 2016, the reported positive trial results for the efficacy of belimumab, but the responder rate was only 54% after 52 weeks of intravenous administration (10 mg/kg). In addition, mouse-human chimeric IgG1κ monoclonal antibody against CD20 (trade name: rituximab), which is specifically expressed on the surface of B cells, has been used for the treatment of malignant lymphoma and has attracted attention as a treatment for systemic lupus erythematosus, but clinical trials were aborted due to reports of serious adverse events, including deaths. Currently, clinical trials using IFN-α and antibodies against its receptor are underway. Favorable results have been obtained in safety and efficacy evaluations, but albeit at low frequency, several adverse events (anemia, lymphopenia, hepatic hypofunction, etc.) have been reported. Thus, although the use of biologic agents can be expected to improve disease states to a high degree, they require regular and long-term administration, causing problems related to the physical and medical-economic burden on the patient, which may reduce the effectiveness of this therapeutic modality. In addition, steroids are used as first-line agents in many autoimmune diseases for which effective treatments have not yet been established. The steroids have strong anti-inflammatory effects, but they also have immunosuppressive effects, and long-term use of the steroids can cause side effects. Therefore, the development of inhibitors against TLR7 or TLR9 is underway to create alternative therapeutic agents to the steroids, and to date, oligonucleotide-based inhibitors of TLR7 and TLR9 (Rommler, F., et al. J. Immunol., 191:3240-3253, 2013) and inhibitors of TLR7 and TLR9 based on small molecule compounds (Lamphier, M., et al. Mol. Pharmacol., 85:429-440, 2014) have been reported, but have not been put to practical use. On the other hand, hydroxychloroquine, approved in Japan in 2015, is a small molecule drug that can be administered orally, but has not been actively prescribed due to concerns about retinopathy and other side effects.

TLR7 has been implicated in a variety of diseases other than systemic lupus erythematosus. Alzheimer's disease is a progressive cognitive loss in which patients have an excess of senile plaques consisting of neurofibrillary tangles made of amyloid-3 and t proteins in the cerebral cortex and subcortical gray matter. The main cause of the disease is thought to be deposition of amyloid-D protein in neurons. The juvenile-onset form of the disease accounts for 2-7% of cases, while the usual form, which is hereditary due to a mutation, occurs in older adults aged 60 years or older, and its incidence increases with age. The Ministry of Health, Labour and Welfare (MHLW) reported in 2013 that 4.62 million people in Japan suffer from dementia, the majority of whom are believed to have Alzheimer's disease. In U.S., it is estimated that there are more than 5 million Alzheimer's disease patients, with annual costs of over US$100 billion in home health care, family care, social care, lost productivity, and premature death. Recently, TLR7 has been implicated in brain diseases caused by neurodegenerative diseases, stroke, or multiple sclerosis. It has been reported that let-7 (microRNA)-induced neurotoxicity, which is abundant in the brain, is dependent on TLR7 (Lehmann, S. M., et al. Nat Neurosci. 15(6):827-835). let-7 is more abundant in the cerebrospinal fluid of patients with Alzheimer's disease than in healthy controls and is thought to be involved in neuronal degeneration.

In a previous screening study, the inventors found that cyclobactiol and its analogous compounds, which are isolated from the mature seeds of the *Psoralea glandulosa* L. and are also contained in *Psoralea corylifolia* of the Chinese herbal medicine, selectively inhibit NF-κB activation upon TLR7 or TLR9 ligand stimulation, and filed an international application together with their collaborators, Teika Pharmaceutical Co. Ltd. and Tokyo Institute of Technology (International Publication No. WO/2017/047769).

RELATED ART DOCUMENTS

Non-Patent Documents

Non-patent document 1: Kumar K R, et al. Regulation of B cell tolerance by the lupus susceptibility gene Ly108. Science. 312:1665-1669, 2006

Non-patent document 2: Deane J A, et al. Control of toll-like receptor 7 expression is essential to restrict autoimmunity and dendritic cell proliferation. Immunity. 27:801-810, 2007

Non-patent document 3: Fukui R, et al. Unc93B1 restricts systemic lethal inflammation by orchestrating Toll-like receptor 7 and 9 trafficking. Immunity. 35:69-81, 2011

Non-patent document 4: Komatsuda A, et al. Up-regulated expression of Toll-like receptors mRNAs in peripheral blood mononuclear cells from patients with systemic lupus erythematosus. Clin Exp Immunol. 152: 482-487, 2008

Non-patent document 5: Christensen S R, et al. Toll-like receptor 7 and TLR9 dictate autoantibody specificity and have opposing inflammatory and regulatory roles in a murine model of lupus. Immunity. 25(3):417-428, 2006

Non-patent document 6: Rommler F, et al. Guanine modification of inhibitory oligonucleotides potentiates their suppressive function. J. Immunol, 191:3240-3253, 2013

Non-patent document 7: Lehmann S M, et al. An unconventional role for miRNA: let-7 activates Toll-like receptor 7 and causes neurodegeneration. Nat Neurosci. 15(6): 827-835, 2012

Non-Patent Document

Patent document 1: WO/2017/047769

SUMMARY OF THE INVENTION

Problems to be Solved by the Invention

CB-7, which showed the highest TLR7 inhibitory effect in Patent Document 1, suppressed TLR7 activation in mouse immune cells (macrophages and dendritic cells) and human immune cells (peripheral blood mononuclear cells and dendritic cells), but its TLR7 inhibitory effect in normal mice was weak and its efficacy in a mouse model of systemic lupus erythematosus was also limited.

Means of Solving the Problems

The inventors investigated methods and substances to create chemical compounds with higher TLR7 inhibitory activity than the lead compound CB-7 and efficacy at the animal level. As a result, they found that several derivatives with novel structures inhibited the induction of the production of inflammatory cytokines IL-6 or IFN-α by TLR7 activation up to about 45 times stronger than CB-7.

According to the present invention, there is provided a chemical compound represented by the following formula

[Chemical 1]

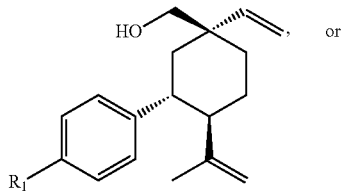
(I)

or

[Chemical 2]

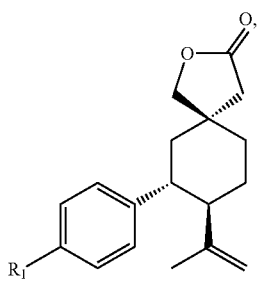
(II)

a pharmacologically acceptable salt thereof, or a prodrug thereof,
in which in formulae (I) and (II),
$R_1$ is:
  $C_{3-5}$ alkoxy group containing at least two oxygen atoms;
  $C_{2-4}$ alkoxy group containing at least one hydroxyl group; and
  the following formula

[Chemical 3]

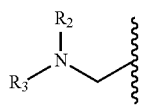

in which $R_2$ and $R_3$ are each independently $C_{1-3}$ alkyl group; or the following formula

[Chemical 4]

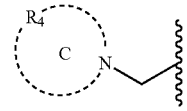

in which C ring is a 3- to 7-membered nitrogen-containing heterocyclic ring,
$R_4$ is a group represented by a combination of —NH—, —O—, —CF$_2$—, —CHF—, —C$_2$H$_2$F$_2$— or —CHF—X—CHF—, and
X is $C_{1-4}$ alkyl group.

According to the present invention, there is also provided the chemical compound, the pharmacologically acceptable salt thereof, or the prodrug thereof, in which $R_1$ is:

[Chemical 5]

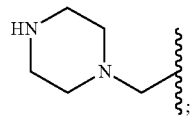

[Chemical 6]

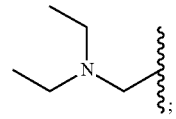

[Chemical 7]

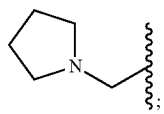

[Chemical 8]

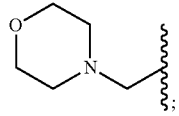

[Chemical 9]

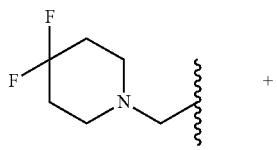   +

[Chemical 10]

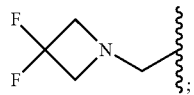

[Chemical 11]

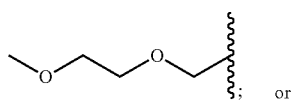   or

[Chemical 12]

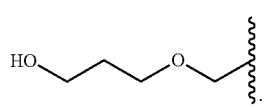

According to the present invention, there is also provided the chemical compound, the pharmacologically acceptable salt thereof, or the prodrug thereof, in which the chemical compound is represented by any of the following formulae:

[Chemical 13]

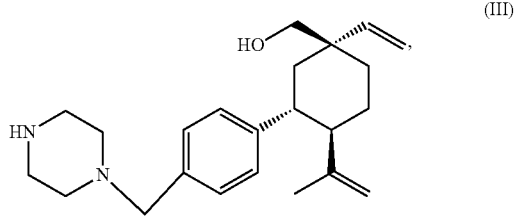
(III)

[Chemical 14]

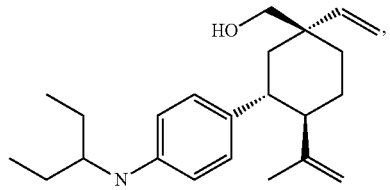
(IV)

[Chemical 15]

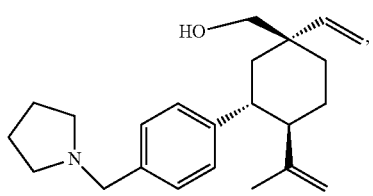
(V)

[Chemical 16]

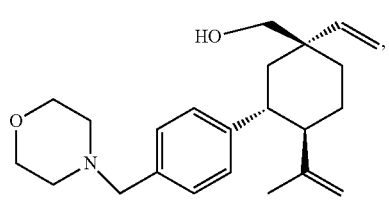
(VI)

[Chemical 17]

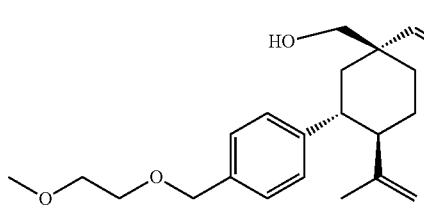
(VII)

[Chemical 18]

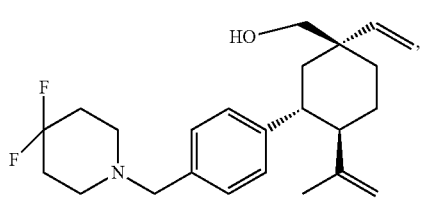
(XIII)

[Chemical 19]

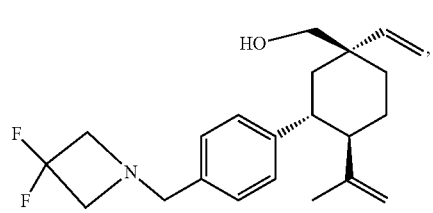
(IX)

[Chemical 20]

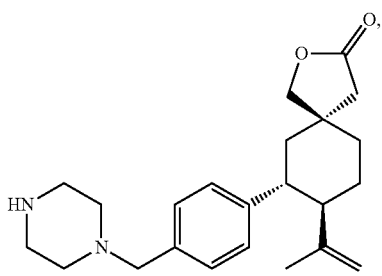
(X)

[Chemical 21]

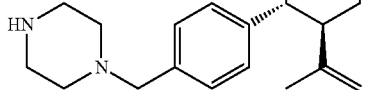
(XI)

[Chemical 22]

(XII)

[Chemical 23]

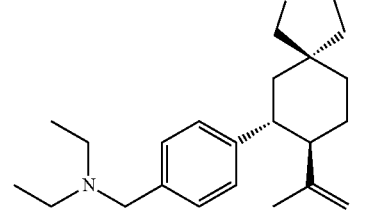
(XIII)

According to the present invention, there is also provided the chemical compound, the pharmacologically acceptable salt, or the prodrug thereof, in which the pharmacologically acceptable salt is a hydrochloride salt or a formate salt.

According to the present invention, there is also provided a toll-like receptor 7 (TLR7) activation inhibitor including the chemical compound, the pharmacologically acceptable salt thereof, or the prodrug thereof.

According to the present invention, there is also provided the TLR7 activation inhibitor, including an inhibitory effect on production of NF-κB, IL-6, TNF-α or IFN-α due to TLR7 activation.

According to the present invention, there is also provided a drug for prevention or treatment of a disease involving TLR7 activation, including the TLR7 activation inhibitor.

According to the present invention, there is also provided the drug for the prevention or the treatment, in which the disease involving the TLR7 activation is an autoimmune disease, an autoinflammatory syndrome, autoimmune pancreatitis, atherosclerosis, sepsis, neurodegenerative disease, graft rejection, graft-versus-host disease, periodontal disease, viral immunodeficiency, IgA nephropathy, primary nephrotic syndrome, primary membranous proliferative glomerulonephritis, purpura nephritis, Langerhans cell histiocytosis, hemophagocytic lymphohistiocytosis, Rosai-Dorfman disease, obesity, type 2 diabetes mellitus or ulcerative colitis.

According to the present invention, there is also provided the drug for the prevention or the treatment, in which the disease involving the TLR7 activation is the autoimmune disease.

According to the present invention, there is also provided the drug for the prevention or the treatment, in which the autoimmune diseases is systemic lupus erythematosus, Sjogren syndrome, scleroderma, polymyositis/dermatomyositis, mixed connective tissue disease, duplication syndrome, antiphospholipid antibody syndrome, Behcet's disease, adult Still's disease, rheumatic fever, malignant rheumatoid arthritis, rheumatoid arthritis, juvenile rheumatoid arthritis, HLA-B27 related rheumatic diseases, IgG4-related syndrome, ANCA-related vasculitis, vasculitis syndrome, multiple sclerosis, psoriasis vulgaris, inflammatory bowel disease, autoimmune thyroid disease, autoimmune hemolytic anemia, idiopathic thrombocytopenic purpura, primary biliary cirrhosis, primary biliary cholangitis, myasthenia gravis, Goodpasture's syndrome, Guillain-Barre syndrome, chronic atrophic gastritis, rapidly progressive glomerulonephritis, anti-glomerular basement membrane nephritis, Addison's disease, type I diabetes mellitus, vitiligo vulgaris, pemphigus vulgaris, pemphigoid, autoimmune neutropenia, autoimmune hepatitis, or autoimmune pancreatitis.

According to the present invention, there is also provided the drug for the prevention or the treatment, in which the autoimmune disease is the systemic lupus erythematosus.

Effects of the Invention

Long-term observations from clinical studies have demonstrated that abnormal TLR7 signaling is one of etiologic factors in patients with systemic lupus erythematosus, and therapeutic strategies that inhibit TLR7 activation and the associated production of proinflammatory cytokines and IFN-α are considered important. The use of biologics for the treatment or prevention of autoimmune diseases is not suitable as a long-term therapeutic agent for autoimmune diseases in view of the physical and medical-economic burden on patients. Therefore, there is a need for effective means of treating autoimmune diseases on a long-term basis that is non-invasive, safe, simple, and economical.

The present invention provides a TLR7 activation inhibitor and a drug for prevention or treatment for diseases involving TLR7 activation containing the TLR7 activation inhibitor, which are non-invasive, safe, simple, and economical. The present invention also provides a drug for prevention or treatment for inflammatory diseases that are effective in inhibiting the activity of NF-κB, IL-6 and IFN-α.

DESCRIPTION OF EMBODIMENTS

Summary and Definitions

Figure 1:
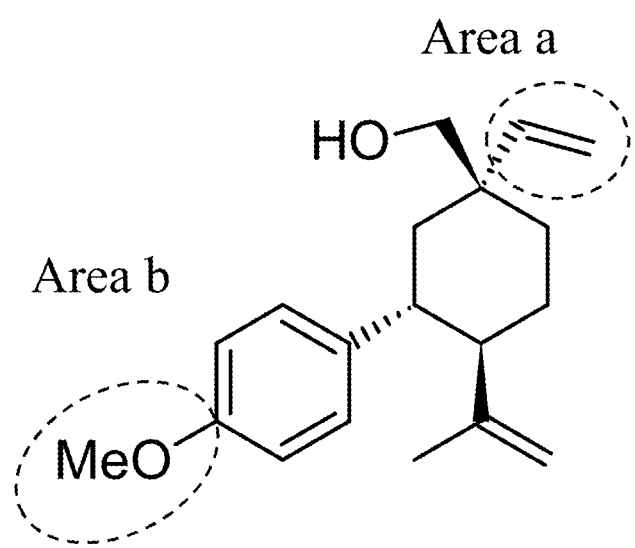
FIG. 1 shows the modified Areas (Areas a and b) in the lead compound CB-7.

Hereinafter, embodiments of the present invention are illustrated in detail. In order to avoid redundancy, explanation for similar contents is not repeated.

For convenience, certain terms employed in the context of the present disclosure are collected here. Unless defined otherwise, all technical and scientific terms used herein have the same meaning as commonly understood by one of the ordinary skilled in the art to which this invention belongs. The singular forms "a", "an", and "the" are used herein to include plural referents unless the context clearly dictates otherwise.

Notwithstanding that the numerical ranges and parameters setting forth the broad scope of the invention are approximations, the numerical values set forth in the specific examples are described as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art.

A wavy line in some formulae represents a covalent bond with a chemical compound represented by formula (I) or (II).

EMBODIMENTS

According to the present invention, there is provided a chemical compound represented by the following formula

[Chemical 24]

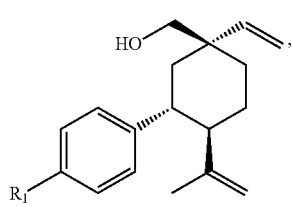

(I)

[Chemical 25]

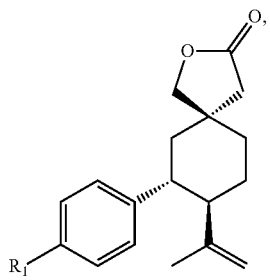

(II)

a pharmacologically acceptable salt thereof, or a prodrug thereof, in which in formulae (I) and (II), $R_1$ is:

$C_{3-5}$ alkoxy group containing at least two oxygen atoms;

$C_{2-4}$ alkoxy group containing at least one hydroxyl group; and the following formula

[Chemical 26]

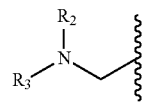

in which $R_2$ and $R_3$ are each independently $C_{1-3}$ alkyl group; or the following formula

[Chemical 27]

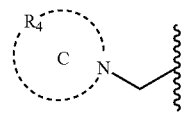

in which C ring is a 3- to 7-membered nitrogen-containing heterocyclic ring, $R_4$ is a group represented by a combination of —NH—, —O—, —$CF_2$—, —CHF—, —$C_2H_2F_2$- or —CHF—X—CHF—, and X is $C_{1-4}$ alkyl group.

$R_1$ may be:

[Chemical 28]

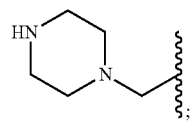

[Chemical 29]

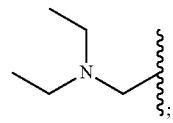

-continued
[Chemical 30]
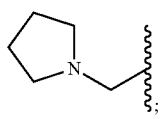
[Chemical 31]
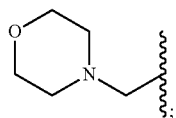
[Chemical 32]
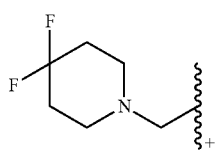
[Chemical 33]
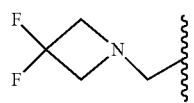
[Chemical 34]
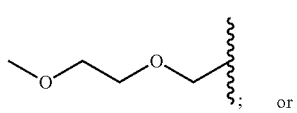; or
[Chemical 35]
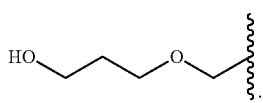.
The chemical compound may be a chemical compound, a pharmacologically acceptable salt thereof, or a prodrug thereof represented by any of the following formulae:
[Chemical 36]
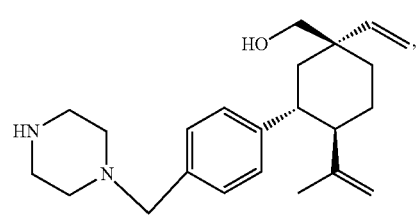 (III)
[Chemical 37]
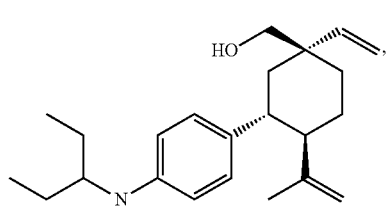 (IV)
-continued
[Chemical 38]
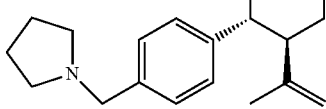 (V)
[Chemical 39]
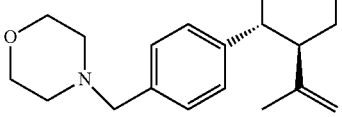 (VI)
[Chemical 40]
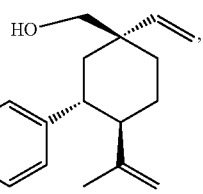 (VII)
[Chemical 41]
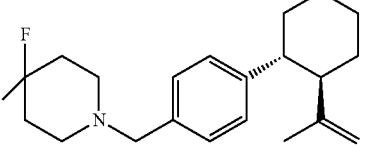 (XIII)
[Chemical 42]
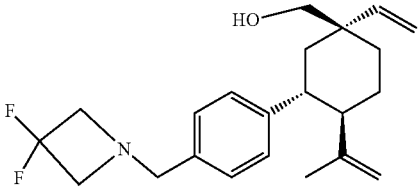 (IX)
[Chemical 43]
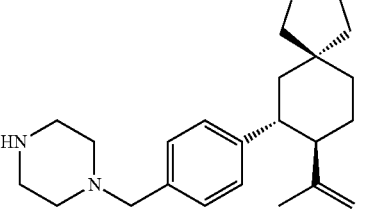 (X)

[Chemical 44]

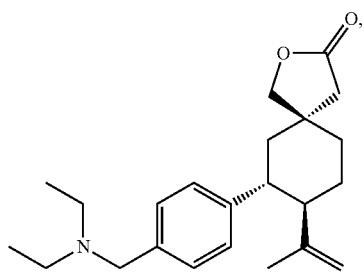

(XI)

[Chemical 45]

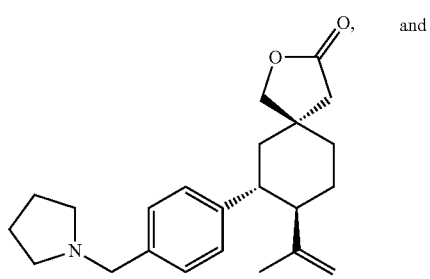

(XII) and

[Chemical 46]

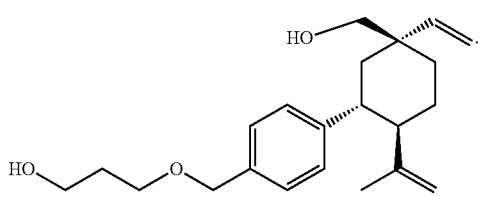

(XIII)

The compounds of the invention may form salts, which are preferably pharmacologically acceptable salts. The pharmacologically acceptable salts are not particularly limited to specific salts as long as they maintain the activity of the compound and do not adversely affect the organism. The salts can include: for example, salts with acids such as acetic acid, propionic acid, butyric acid, formic acid, trifluoroacetic acid, maleic acid, tartaric acid, citric acid, stearic acid, succinic acid, ethyl succinic acid, malonic acid, lactobionic acid, gluconic acid, glucoheptonic acid, benzoic acid, methanesulfonic acid, ethanesulfonic acid, 2-hydroxyethanesulfonic acid, benzenesulfonic acid, paratoluenesulfonic acid (tosic acid), lauryl sulfate, malic acid, aspartic acid, glutamic acid, adipic acid, cysteine, N-acetylcysteine, hydrochloric acid, hydrobromic acid, phosphoric acid, sulfuric acid, hydroiodic acid, nicotinic acid, oxalic acid, picric acid, thiocyanic acid, undecanoic acid, acrylic acid polymer and carboxyvinyl polymer; salts with inorganic bases such as lithium, sodium, potassium and calcium; salts with organic amines such as morpholine and piperidine; and salts with amino acids. Preferably, the salt is a salt with hydrochloric acid (hydrochloride salt) or with formic acid (formate salt).

The prodrug means a chemical compound that is converted to the chemical compound represented by one of the formulas (I) to (XIII) by reaction with enzymes or stomach acid under physiological conditions in living organism. For example, esters that release the chemical compounds by hydrolysis in living organism are included.

The chemical compounds of the invention or salts thereof may be solvates. The solvates should be non-toxic and water soluble. The suitable solvates include, for example, solvates with water and solvates with alcoholic solvents (methanol, ethanol, etc.).

The present invention also provides a TLR7 activation inhibitor containing the chemical compound, pharmacologically acceptable salt, or prodrug thereof. TLR7 activation has biological responses that are known activities of TLR7, such as cytokine production (e.g., TNF-α, IL-6, IL-12, IFN-α and IFN-β) in macrophages or dendritic cells, chemokine production (e.g., CCL2, CCL5, CXCL8 and CXCL10), enhanced cell proliferation in B cells, enhanced expression of co-stimulatory molecules (e.g., CD80 and CD86), antibody production and induction of class switch, and induction of immune unresponsiveness in T cells. The TLR7 activation inhibitor can inhibit the activation (biological responses), preferably NF-κB, IL-6, TNF-α or IFN-α production caused by the TLR7 activation. The inhibition of TLR7 activation can be achieved by inhibiting the TLR7 activation (e.g., NF-κB, IL-6, TNF-α and IFN-α production) by 10%, 20%, 30%, 40%, 50%, 60%, 70%, 80%, 90%, 95%, 98%, 99%, or 99.9% or by a range between two values selected arbitrarily from the above group of numbers. The TLR7 activation inhibitor of the present invention may also be used as research reagents for the analysis of TLR7 expression, function and related signaling mechanisms.

The TLR7 activation inhibitor of the present invention can inhibit TLR7 activation and is useful as a medicament for prevention or treatment of diseases involving TLR7 activation. In other words, the present invention also provides a drug for prevention or treatment of diseases involving TLR7 activation, which contains the TLR7 activation inhibitor of the above invention.

The disease involving the TLR7 activation include, for example, an autoimmune disease, an autoinflammatory syndrome, autoimmune pancreatitis, atherosclerosis, sepsis, neurodegenerative disease, graft rejection, graft-versus-host disease, periodontal disease, viral immunodeficiency, IgA nephropathy, primary nephrotic syndrome, primary membranous proliferative glomerulonephritis, purpura nephritis, Langerhans cell histiocytosis, hemophagocytic lymphohistiocytosis, Rosai-Dorfman disease, obesity, type 2 diabetes mellitus and ulcerative colitis, but not limited thereto.

A target disease of the drug for the prevention or the treatment according to the present invention is preferably the autoimmune disease. The autoimmune disease includes, for example, systemic lupus erythematosus, Sjogren syndrome, scleroderma, polymyositis/dermatomyositis, mixed connective tissue disease, duplication syndrome, antiphospholipid antibody syndrome, Behcet's disease, adult Still's disease, rheumatic fever, malignant rheumatoid arthritis, rheumatoid arthritis, juvenile rheumatoid arthritis, HLA-B27 related rheumatic diseases (e.g., ankylosing spondylitis, Reiter's syndrome, and psoriatic arthritis), IgG4-related syndrome, ANCA-related vasculitis (microscopic polyangiitis, granulomatosis with polyangiitis, and eosinophilic granulomatosis with polyangiitis), vasculitis syndrome (polymyalgia rheumatica, giant cell arteritis, and polyarteritis nodosa), multiple sclerosis, psoriasis vulgaris, inflammatory bowel disease, autoimmune thyroid disease (Hashimoto's thyroiditis, and Basedow's disease), autoimmune hemolytic anemia, idiopathic thrombocytopenic purpura, primary biliary cirrhosis, primary biliary cholangitis, myasthenia gravis, Goodpasture's syndrome, Guillain-Barre syndrome, chronic atrophic gastritis, rapidly progressive glomerulonephritis, anti-glomerular basement membrane nephritis, Addison's disease, type I diabetes mellitus, vitiligo vulgaris, pemphigus vulgaris, pemphigoid, autoimmune neutropenia, autoimmune hepatitis, or autoimmune pancreatitis. The autoimmune disease is preferably the systemic lupus erythematosus.

The drug for the prevention or the treatment according to the present invention can be formulated by blending the chemical compound represented by any of the formulas (I) to (XIII) as an active ingredient with a pharmaceutically acceptable carrier or additive as appropriate, according to known methods for manufacturing pharmaceutical preparations (e.g., methods described in the Japanese Pharmacopoeia). Specifically, the formulated drug includes, for example, oral or parenteral preparations such as tablets (including sugar-coated tablets, film-coated tablets, sublingual tablets, orally disintegrating tablets, and bacal tablets), round tablets, dispersions, granules, capsules (including soft capsules and microcapsules), trochees, syrups, liquids, emulsions, suspension formulations, controlled release preparations (e.g., rapid release, sustained release, and sustained release microcapsules), aerosols, films (e.g., orally disintegrating films, films applied to the oral mucosa, etc.), injectables (e.g., subcutaneous, intravenous, intramuscular, and intraperitoneal injectables), intravenous drips, transdermal formulations, ointments, lotions, pastes, suppositories (e.g., anal suppositories, and vaginal suppositories), pellets, intranasal, transpulmonary (inhalation), ophthalmic solutions. Ratio of the carriers or additives can be set appropriately based on the range usually employed in the pharmaceutical field. The carriers or additives that can be used include, for example, various carriers such as water, saline, other aqueous solvents, and aqueous or oil-based substrates, and various additives such as excipients, binding agents, pH adjusters, disintegrants, absorption accelerators, lubricants, coloring agents, taste masking agents, and flavoring agents, but not limited thereto.

The additives that can be mixed into tablets, capsules, etc, include: for example, binders such as gelatin, cornstarch, tragacanth, and gum arabic; excipients such as crystalline cellulose; bulking agents such as cornstarch, gelatin, and alginic acid; lubricants such as magnesium stearate; sweeteners such as sucrose, lactose, or saccharin; and flavoring agents such as peppermint, acamonium oil, or cherry. If unit form of the formulation is the capsule, the above types of materials can additionally contain liquid carriers such as fats and oils. Sterile compositions for injection can be prepared according to normal formulation procedures (e.g., dissolving or suspending active ingredient(s) in a solvent such as water for injection or natural vegetable oil). Aqueous solutions for injection include, for example, saline, isotonic solutions containing glucose or other auxiliary agents (e.g., D-sorbitol, D-mannitol, and sodium chloride), and appropriate dissolution aids, such as alcohol (e.g., ethanol), polyalcohol (e.g., propylene glycol, and polyethylene glycol), nonionic surfactants (e.g., polysorbate 80, and HCO-50) may be used in combination. Oil-based liquids include, for example, sesame oil and soybean oil. The oil-based liquids may be used in combination with benzyl benzoate, benzyl alcohol, etc., as dissolution aids. It may also be blended with buffers (e.g., phosphate buffer, and sodium acetate buffer), painless agents (e.g., benzalkonium chloride, and procaine hydrochloride), stabilizers (e.g., human serum albumin, and polyethylene glycol), preservatives (e.g., benzyl alcohol, and phenol), antioxidants, etc.

The drug for the prevention or the treatment according to the present invention can be safely administered to humans and mammals other than humans (e.g., rats, mice, rabbits, sheep, pigs, cattle, cats, dogs, and monkeys).

The drug for the prevention or the treatment according to the present invention can be produced according to the usual methods by adding the active ingredient at a ratio of usually 0.01 to 100% (w/w), preferably 0.1 to 95% (w/w) of the total amount of the formulation, depending on the dosage form, administration method, carrier, and other factors.

Dosage of the drug for the prevention or the treatment according to the present invention varies depending on subjects, symptoms, route of administration, etc. In the case of oral administration, the dosage in a human weighing, for example, about 60 kg is generally about 0.01 to 1000 mg per day, preferably about 0.1 to 100 mg per day, more preferably about 0.5 to 50 mg per day. For parenteral administration, the single dose depends on the patient's condition, symptoms, and method of administration. For example, injectable formulation is usually administered intravenously at a dose of about 0.01 to 100 mg per kg of body weight, preferably about 0.01 to 50 mg per kg, more preferably about 0.01 to 20 mg per kg. The total daily dose may be a single dose or divided doses.

The drug for the prevention or the treatment according to the present invention can be used in combination with other agents. The other agents include, for example, agents for treating autoimmune diseases, agents for treating hyperlipidemia, non-steroidal anti-inflammatory drugs, and steroidal agents. In particular, it is preferable to use the drug according to the present invention in combination with the agents for treating autoimmune diseases. The agents for treating autoimmune diseases include steroids including glycocorticoids, non-steroidal anti-inflammatory agents, biological agents (e.g., antibody drugs), immunosuppressive agents, and antimalarial drugs.

The present invention includes each of the following inventions:

- a method for inhibiting TLR7 activation, including administering to a mammal an effective amount of a chemical compound represented by any of the formulae (I) to (XIII), a pharmacologically acceptable salt thereof, or a prodrug thereof;
- a chemical compound represented by any of the formulae (I) to (XIII), a pharmacologically acceptable salt thereof, or a prodrug thereof, for inhibition of TLR7 activation;
- use of a chemical compound represented by any of the formulae (I) to (XIII), a pharmacologically acceptable salt thereof, or a prodrugs thereof to produce TLR7 activation inhibitors;
- a method for preventing or treating diseases involving TLR7 activation, including administering to a mammal an effective amount of a chemical compound represented by any of the formulae (I) to (XIII), a pharmacologically acceptable salt thereof, or a prodrug thereof;
- a chemical compound represented by any of the formulae (I) to (XIII), a pharmacologically acceptable salt thereof, or a prodrug thereof, for prevention or treatment of diseases involving TLR7 activation.
- use of a chemical compound represented by any of the formulae (I) to (XIII), a pharmacologically acceptable salt thereof, or a prodrug thereof, to produce a drug for prevention or treatment of diseases involving TLR7 activation.

EXAMPLES

Example 1: Synthesis of Derivatives with Modified Areas a and b

Areas a and b in CB-7 shown in FIG. 1 were modified. The modifications were performed by Albany Molecular Research Inc. (USA). Tables 1 and 2 show the CB-7 derivatives obtained by the modification. B2-24-4·HCl was obtained as the hydrochloride salt.
TABLE 1
(1) CB-7 derivatives with modified Areas a and b
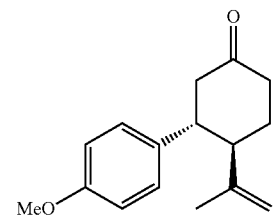 [SMILES: C=C(C)[C@@H]1CCC(=O)C[C@H]1c1ccc(OC)cc1]
I-7 (Intermediate)
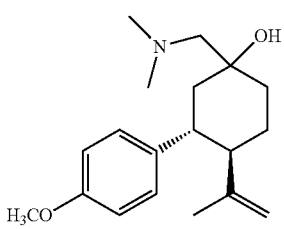 [SMILES: C=C(C)[C@@H]1CCC(O)(CN(C)C)C[C@H]1c1ccc(OC)cc1]
B2-2A
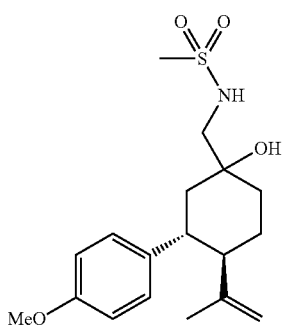 [SMILES: C=C(C)[C@@H]1CCC(O)(CNS(C)(=O)=O)C[C@H]1c1ccc(OC)cc1]
B2-3A
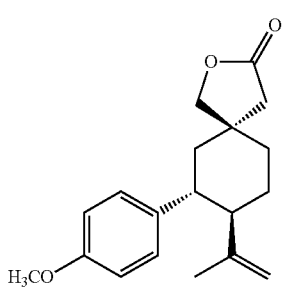 [SMILES: C=C(C)[C@@H]1CC[C@]2(COC(=O)C2)C[C@H]1c1ccc(OC)cc1]
B2-5A
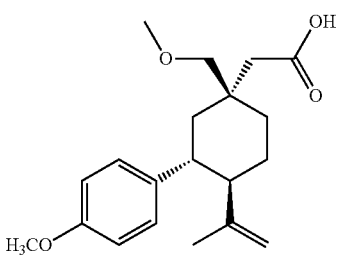 [SMILES: C=C(C)[C@@H]1CC[C@@](COC)(CC(=O)O)C[C@H]1c1ccc(OC)cc1]
B2-5B
TABLE 1-continued
(1) CB-7 derivatives with modified Areas a and b
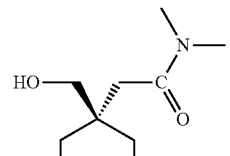
B2-6
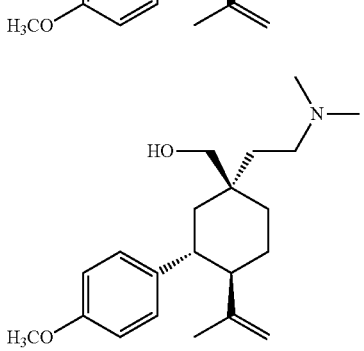
B2-6A
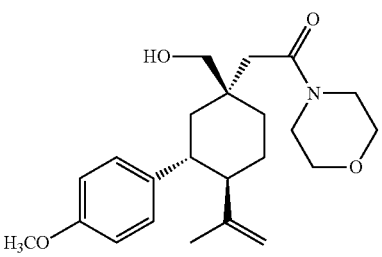 [SMILES: C=C(C)[C@@H]1CC[C@@](CO)(CC(=O)N2CCOCC2)C[C@H]1c1ccc(OC)cc1]
B2-6-7
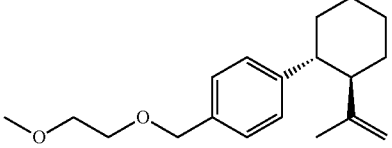
B2-13
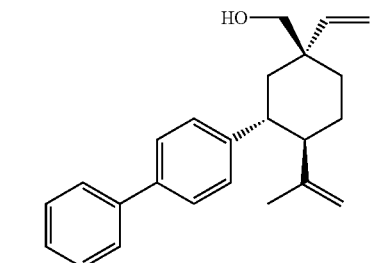
B2-18
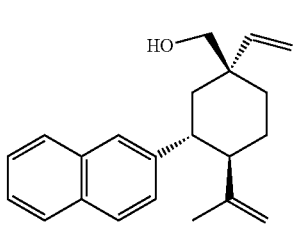 [SMILES: C=C[C@]1(CO)CC[C@@H](C(=C)C)[C@H](c2ccc3ccccc3c2)C1]
B2-19

TABLE 1-continued
(1) CB-7 derivatives with modified Areas a and b
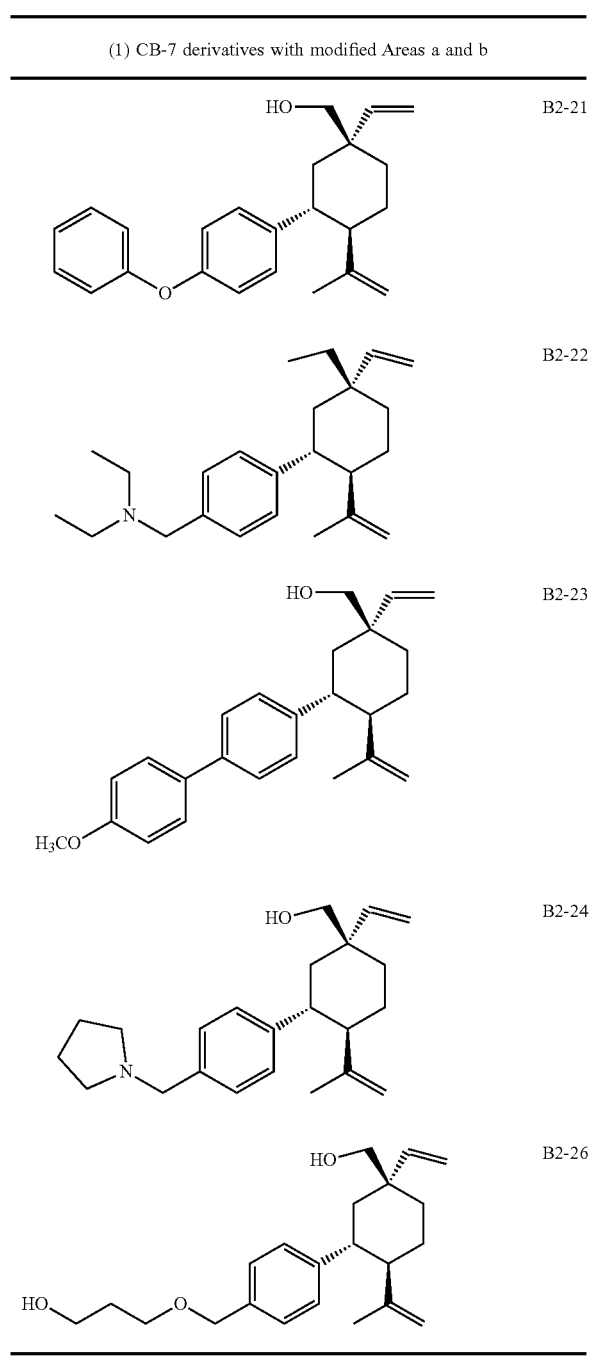
TABLE 2
(2) CB-7 derivatives with modified Areas a and b
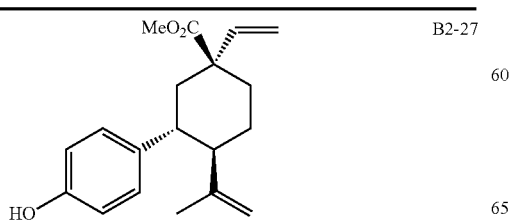
TABLE 2-continued
(2) CB-7 derivatives with modified Areas a and b
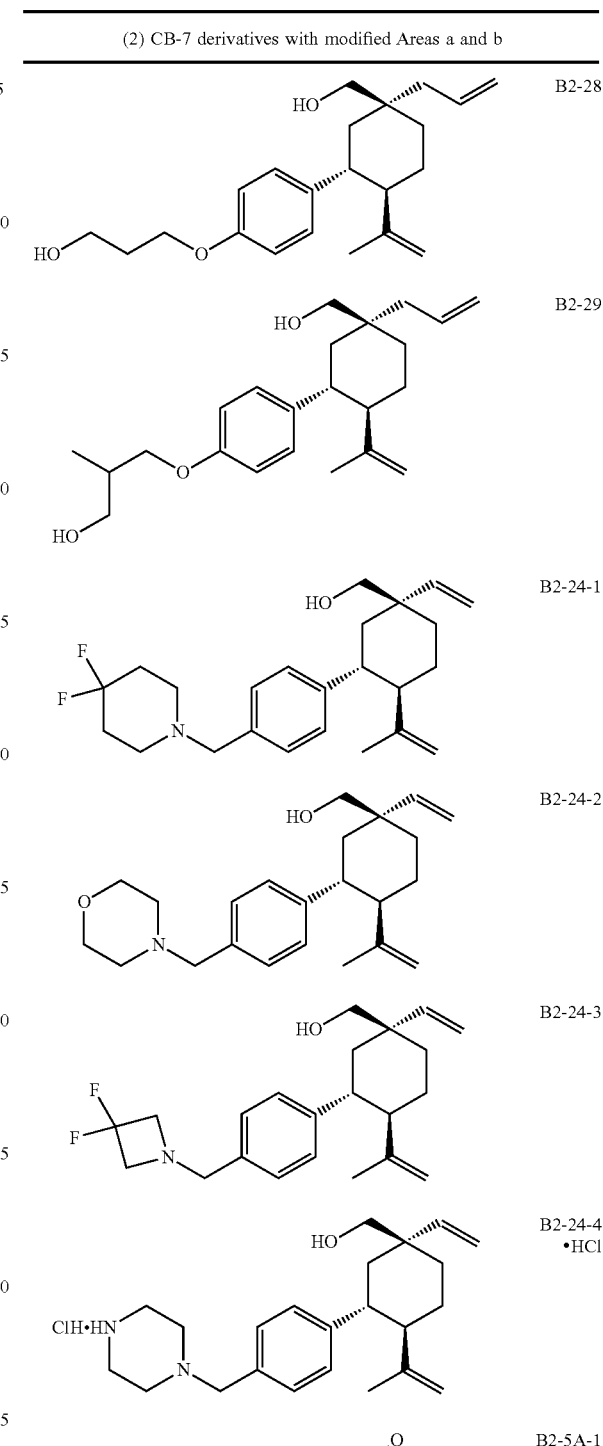
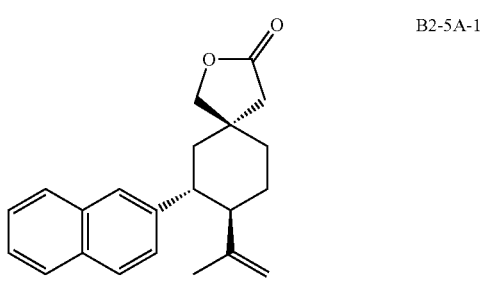

TABLE 2-continued (2) CB-7 derivatives with modified Areas a and b

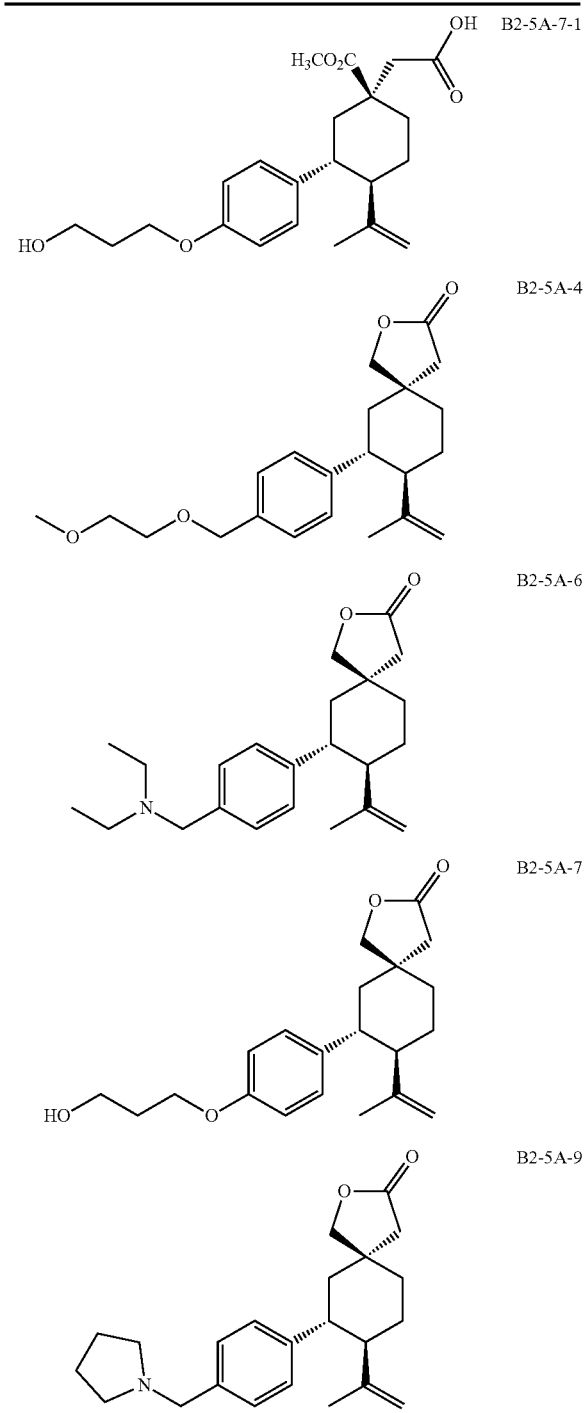

Synthesis of Each Chemical Compound

Reagents were purchased from the commercial markets and used as received. $^1$H NMR spectra were obtained on a 300 MHz Bruker AVANCE 300 spectrometer and a 400 MHz Bruker AVANCE 400 spectrometer using tetramethylsilane as an internal standard. Thin layer chromatography (TLC) was performed using a Whatman No. 4500-101 (Diamond No. MK6F silica gel 60 angstrom) plate.

The name of the chemical compound (numbered chemical compound) represented by ["chemical compound" plus "number"] (e.g., chemical compound 1) or ["chemical compound Int-" plus "number"] (e.g., chemical compound Int-1) is only valid in each synthetic example. Thus, even if a numbered chemical compound in a synthetic example is identical to a numbered chemical compound in another synthetic example, both chemical compounds may be structurally different, and even if a numbered chemical compound in a synthetic example differs from a numbered chemical compound in another synthetic example, both chemical compounds may be structurally identical. In other words, identity between numbered chemical compounds is determined by structure.

Synthesis Example 1

Synthesis of Chemical Compounds B2-6 and B2-6A

A method for the production of chemical compounds B2-6 (also called ALB-208276) and B2-6A (also called ALB-208787) is as follows (also called scheme 1).

[Chemical 47]

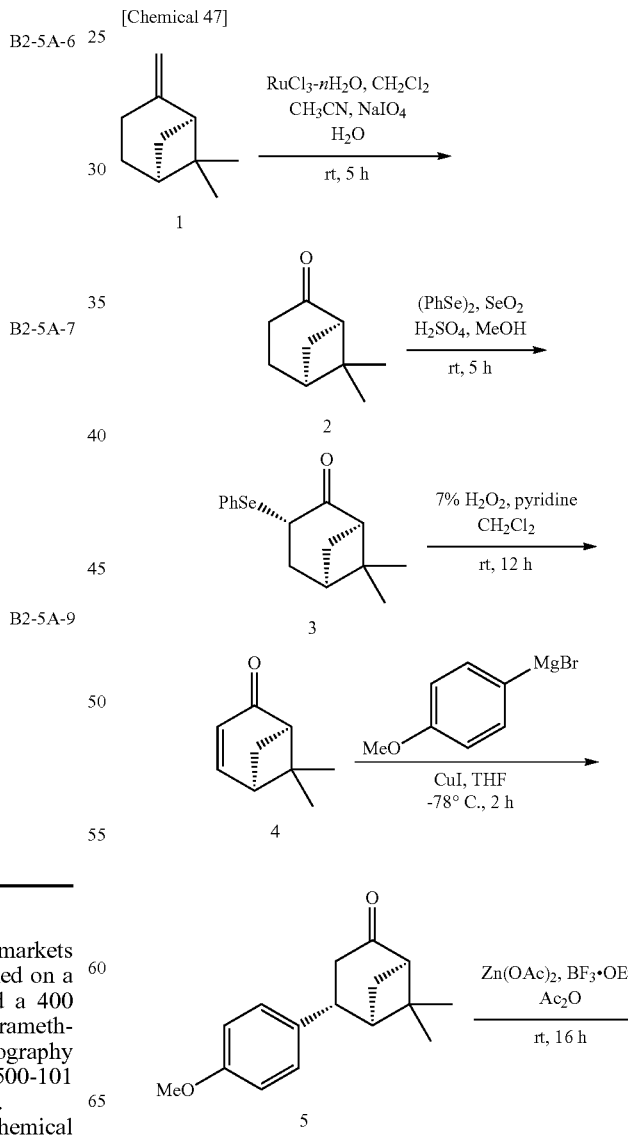

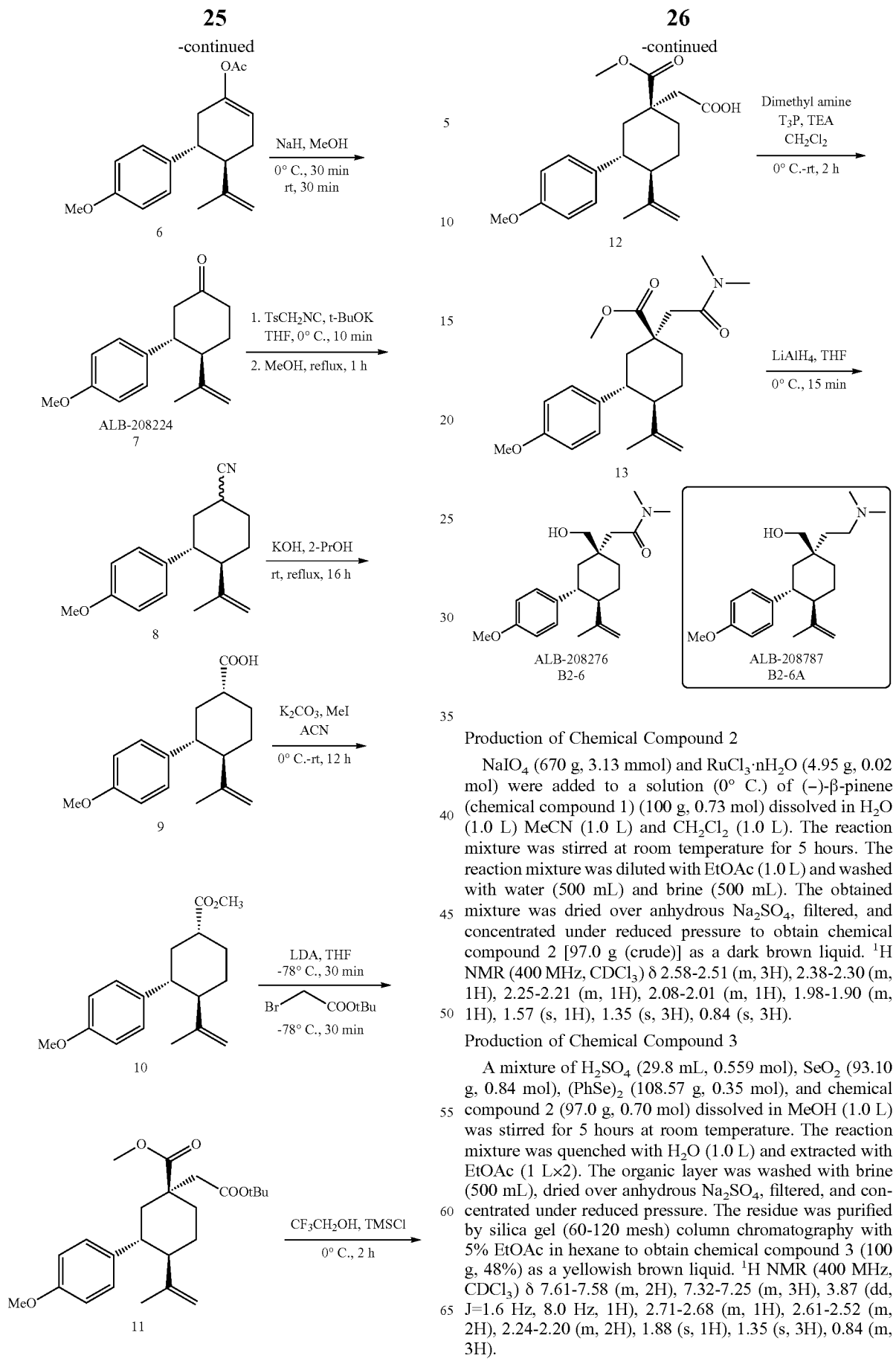

Production of Chemical Compound 2

NaIO$_4$ (670 g, 3.13 mmol) and RuCl$_3$·nH$_2$O (4.95 g, 0.02 mol) were added to a solution (0° C.) of (−)-β-pinene (chemical compound 1) (100 g, 0.73 mol) dissolved in H$_2$O (1.0 L) MeCN (1.0 L) and CH$_2$Cl$_2$ (1.0 L). The reaction mixture was stirred at room temperature for 5 hours. The reaction mixture was diluted with EtOAc (1.0 L) and washed with water (500 mL) and brine (500 mL). The obtained mixture was dried over anhydrous Na$_2$SO$_4$, filtered, and concentrated under reduced pressure to obtain chemical compound 2 [97.0 g (crude)] as a dark brown liquid. $^1$H NMR (400 MHz, CDCl$_3$) δ 2.58-2.51 (m, 3H), 2.38-2.30 (m, 1H), 2.25-2.21 (m, 1H), 2.08-2.01 (m, 1H), 1.98-1.90 (m, 1H), 1.57 (s, 1H), 1.35 (s, 3H), 0.84 (s, 3H).

Production of Chemical Compound 3

A mixture of H$_2$SO$_4$ (29.8 mL, 0.559 mol), SeO$_2$ (93.10 g, 0.84 mol), (PhSe)$_2$ (108.57 g, 0.35 mol), and chemical compound 2 (97.0 g, 0.70 mol) dissolved in MeOH (1.0 L) was stirred for 5 hours at room temperature. The reaction mixture was quenched with H$_2$O (1.0 L) and extracted with EtOAc (1 L×2). The organic layer was washed with brine (500 mL), dried over anhydrous Na$_2$SO$_4$, filtered, and concentrated under reduced pressure. The residue was purified by silica gel (60-120 mesh) column chromatography with 5% EtOAc in hexane to obtain chemical compound 3 (100 g, 48%) as a yellowish brown liquid. $^1$H NMR (400 MHz, CDCl$_3$) δ 7.61-7.58 (m, 2H), 7.32-7.25 (m, 3H), 3.87 (dd, J=1.6 Hz, 8.0 Hz, 1H), 2.71-2.68 (m, 1H), 2.61-2.52 (m, 2H), 2.24-2.20 (m, 2H), 1.88 (s, 1H), 1.35 (s, 3H), 0.84 (m, 3H).

Production of Chemical Compound 4

At 0° C., 7% $H_2O_2$ (70.00 mL, 0.160 mmol) and pyridine (12.20 mL, 0.22 mol) were added to a solution of chemical compound 3 (32.50 g, 0.110 mol) dissolved in $CH_2Cl_2$ (400 mL) and the mixture was stirred for 12 hours at room temperature. The reaction mixture was diluted with $CH_2Cl_2$ (500 mL) and washed with water (200 mL) and brine (250 mL). The obtained organic layer was dried over anhydrous $Na_2SO_4$, filtered, and concentrated under reduced pressure. The crude product was purified by silica gel (60-120 mesh) column chromatography using 0-5% EtOAc in hexane to obtain chemical compound 4 (13.00 g, 81%) as a brown liquid. $^1$H NMR (400 MHz, $CDCl_3$) δ 7.54-7.50 (m, 1H), 5.95 (d, J=8.8 Hz, 1H), 2.86-2.83 (m, 1H), 2.73-2.57 (m, 2H), 2.13 (s, 1H), 1.51 (s, 3H), 1.04 (m, 3H).

Production of Chemical Compound 5

At −78° C., a solution of chemical compound 4 (8.00 g, 58.8 mmol) dissolved in THF (100 mL) was added to a mixture of CuI (5.60 g, 29.4 mmol) and 4-methoxyphenylmagnesium bromide (70.60 mL, 1 M in THF, 70.6 mmol) dissolved in THF (10 mL) and the mixture was stirred at −78° C. for 2 hours. The reaction mixture was quenched with saturated $NH_4Cl$ (250 mL) and extracted with EtOAc (200 mL×2). The organic layer was washed with brine (100 mL), dried over anhydrous $Na_2SO_4$, filtered, and concentrated under reduced pressure. The crude product was purified by silica gel (60-120 mesh) column chromatography using 0-10% EtOAc in hexane to obtain chemical compound 5 (9.00 g, 63%) as a colorless liquid. $^1$H NMR (400 MHz, $CDCl_3$) δ 7.17 (d, J=8.4 Hz, 2H), 6.85 (d, J=8.4 Hz, 2H), 3.80 (s, 3H), 3.377 (t, J=8.0 Hz, 1H), 2.81-2.61 (m, 3H), 2.57-2.51 (m, 1H), 2.39-2.36 (m, 1H), 1.89 (d, J=10.8 Hz, 1H), 1.39 (s, 3H), 0.98 (m, 3H).

Production of Chemical Compound 6

$Zn(OAc)_2$ (8.36 g, 45.0 mmol) and $BF_3·OEt_2$ (2.81 mL, 22.0 mmol) were added to a solution of chemical compound 5 (10.70 g, 43.0 mmol) dissolved in $Ac_2O$ (100 mL) and the mixture was stirred at room temperature for 16 hours. The reaction mixture was diluted with $H_2O$ (100 mL). The obtained mixture was extracted with EtOAc (100 mL×2). The organic layer was mixed, washed with saturated $NaHCO_3$ (1000 mL) and brine (500 mL), dried over $MgSO_4$ and concentrated under reduced pressure to obtain a residual oil. It was purified by combiflash column chromatography using 0-10% EtOAc in hexane to obtain chemical compound 6 (7.00 g, 56%) as an off-white solid. $^1$H NMR (400 MHz, $CDCl_3$) δ 7.09 (d, J=8.4 Hz, 2H), 6.80 (d, J=8.8 Hz, 2H), 5.45-5.44 (m, 1H), 4.67-4.59 (m, 2H), 3.77 (s, 3H), 2.96-2.89 (m, 1H), 2.70-2.64 (m, 1H), 2.39-2.24 (m, 4H), 2.11 (s, 3H), 1.49 (s, 3H).

Production of Chemical Compound 7 (also called ALB-208224 or 1-7 (Intermediate))

NaH (0.57 g, 60% in mineral oil, 14.0 mmol) was gradually added to a solution of chemical compound 6 (7.00 g, 28.0 mmol) dissolved in MeOH (100 mL) (0° C.) over 30 minutes. The reaction mixture was quenched with saturated $NH_4Cl$ (10 mL), and MeOH in the mixture was evaporated under reduced pressure. The obtained solid was filtered, washed with water (250 mL), and dried to obtain chemical compound 7 (ALB-208224 or 1-7 (intermediate)) (5.90 g, 99%) as an off-white solid. $^1$H NMR (400 MHz, $CDCl_3$) δ 7.00 (d, J=8.4 Hz, 2H), 6.75 (d, J=8.8 Hz, 2H), 4.56 (d, J=10.4 Hz, 2H), 3.71 (s, 3H), 2.89-2.82 (m, 1H), 2.67-2.60 (m, 1H), 2.45 (d, J=10 Hz, 4H), 2.04-2.00 (m, 1H), 1.84-1.76 (m, 1H), 1.44 (s 3H).

Production of Chemical Compound 8

An ice-cold solution of p-toluenesulfonylmethyl isocyanide (2.39 g, 12.2 mmol) dissolved in THF (25 mL) and tert-BuOK (2.75 g, 24.6 mmol) was stirred for 10 minutes, and then a solution of compound 7 (1.50 g, 6.14 mmol) dissolved in THF (5.0 mL) was added to the solution. The reaction mixture was stirred at 0° C. for 10 minutes, and MeOH (20 mL) was added to the mixture. The obtained mixture was stirred under reflux for 1 hour and concentrated under reduced pressure. The crude product was purified by combiflash column chromatography using 0-30% EtOAc in hexane to obtain chemical compound 8 (0.60 g, 38%) as a colorless liquid. $^1$H NMR (400 MHz, $CDCl_3$) δ 7.05 (d, J=8.4 Hz, 2H), 6.82 (d, J=8.8 Hz, 2H), 4.64 (d, J=10.4 Hz, 2H), 3.78 (s, 3H), 2.96-2.89 (m, 1H), 2.74-2.68 (m, 1H), 2.53-2.49 (m, 4H), 2.11-2.07 (m, 1H), 1.91-1.55 (m, 1H), 1.51 (s, 3H).

Production of Chemical Compound 9

At room temperature, KOH (5.20 g, 94.1 mmol) was added to a solution of chemical compound 8 (2.40 g, 9.41 mmol) dissolved in 2-propanol (30 mL). The reaction mixture was stirred under reflux for 16 hours. The reaction mixture was diluted with cold water (100 mL) and acidified by the addition of HCl (2 N). The obtained mixture was extracted with EtOAc (50 mL×2). The organic layer was mixed, washed with brine (100 mL), dried over $MgSO_4$ and concentrated under reduced pressure to obtain chemical compound 9 (2.20 g, 85%) as an off-white solid. $^1$H NMR (400 MHz, $CDCl_3$) δ 7.17 (d, J=8.8 Hz, 2H), 6.85 (d, J=8.8 Hz, 2H), 4.64 (d, J=10.4 Hz, 2H), 3.79 (s, 3H), 3.37 (t, J=8.0 Hz, 2H), 2.81-2.54 (m, 4H), 2.39-2.36 (m, 1H), 1.89 (t, J=5.4 Hz, 1H), 2.11-2.07 (m, 1H), 1.91-1.55 (m, 1H), 1.51 (s, 3H).

Production of Chemical Compound 10

At 0° C., $K_2CO_3$ (3.25 g, 23.58 mmol) and MeI (1.57 mL, 25.27 mmol) were dropped to an ice-cold solution of chemical compound 9 (2.30 g, 8.424 mmol) dissolved in $CH_3CN$ (20 mL). The reaction mixture was stirred at room temperature for 12 hours. The obtained mixture was extracted with EtOAc (100 mL×3). The organic layer was mixed, washed with brine (100 mL), dried over $MgSO_4$ and concentrated under reduced pressure. The crude product was purified by combiflash column chromatography using 0-20% EtOAc in hexane to obtain chemical compound 10 (2.20 g, 91.6%) as a pale yellow oil. $^1$H NMR (400 MHz, $CDCl_3$) δ 7.04 (d, J=8.8 Hz, 2H), 6.79 (d, J 8.4 Hz, 2H), 4.55 (m, 2H), 3.76 (s, 3H), 3.65 (s, 3H), 2.54-2.45 (m, 2H), 2.30-2.24 (m, 1H), 2.10-2.06 (m, 2H), 1.89-1.85 (m, 1H), 1.62-1.58 (m, 3H), 1.49 (s 3H).

Production of Chemical Compound 11

At −78° C., chemical compound 10 (1.00 g, 3.40 mmol) dissolved in THF (4.0 mL) was dropped to a solution of lithium diisopropylamide (5.20 mL, 2.0 M in THF, 10.4 mmol) dissolved in THF (6.0 mL). The reaction mixture was stirred at −78° C. for 30 minutes. tert-butyl 2-bromoacetate (1.00 mL, 6.80 mmol) was added to the reaction mixture, and the reaction mixture was quenched with saturated $NH_4Cl$ solution (15 mL). The obtained mixture was extracted with EtOAc (50 mL×3). The organic layer was mixed, washed with brine (25 mL), dried over $Na_2SO_4$ and concentrated under reduced pressure. The crude product was purified by combiflash column chromatography using 0-10% EtOAc in hexane to obtain chemical compound 11 (0.50 g, 36%) as a colorless liquid.

Production of Chemical Compound 12

TMSCl (0.5 mL, 3.94 mmol) was dropped to a solution (0° C.) of chemical compound 11 (0.5 g, 1.24 mmol) dissolved in 2,2,2-trifluoroethanol (2.0 mL). The reaction mixture was stirred at 0° C. for 2 hours. The residual solvent was evaporated, and the residue was diluted with EtOAc (15 mL) and washed with water (20 mL). The organic layer was washed with brine (15 mL), dried over MgSO$_4$ and concentrated under reduced pressure to obtain a colorless viscous material. It was purified by combiflash column chromatography using 0-50% EtOAc in hexane to obtain chemical compound 12 (0.40 g, 74%) as a colorless viscous substance.

Production of Chemical Compound 13

At 0° C., TEA (0.26 mL, 1.20 mmol), T$_3$P (50% w/w in EtOAc) (0.39 mL, 1.20 mmol), and N, N-dimethylamine (1 M in THF) (0.4 mL, 0.80 mmol) in that order were added to an ice-cold solution of chemical compound 12 (0.14 g, 0.40 mmol) dissolved in CH$_2$Cl$_2$ (20 mL). The reaction mixture was stirred at room temperature for 2 hours and diluted with H$_2$O (5.0 mL). The obtained mixture was extracted with CH$_2$Cl$_2$ (5.0 mL×2). The organic layer was mixed, washed with brine (5.0 mL), dried over MgSO$_4$ and concentrated under reduced pressure. The crude product was purified by combiflash column chromatography using 0-60% EtOAc in hexane to obtain chemical compound 13 (0.15 g, 87%) as a colorless viscous material ESI MS m/z 374 [M+H]$^+$.

Production of Chemical Compounds ALB-208276 (B2-6) and ALB-208787 (B2-6A)

At 0° C., LiAlH$_4$ (0.50 mL, 2.0 M in THF, 0.90 mmol) was added to an ice-cold solution of chemical compound 13 (0.13 g, 0.30 mmol) dissolved in THF (5.0 mL). The reaction mixture was stirred at 0° C. for 15 minutes and diluted with H$_2$O and HCl (2 N). The obtained mixture was extracted with EtOAc (10 mL×2). The organic layer was mixed, washed with brine (10 mL), dried over MgSO$_4$ and concentrated under reduced pressure. The crude product was purified by combiflash column chromatography using 0-70% EtOAc in hexane to obtain ALB-208276 (B2-6) (0.03 g, 25%) and ALB-208787 (B2-6A) (0.015 g, 13%) as off-white colorless viscous substances.

ALB-208276(B2-6)

$^1$H NMR (400 MHz, DMSO-d$_6$) δ 7.05 (d, J=8.4 Hz, 2H), 6.77 (d, J=8.4 Hz, 2H), 4.78 (t, J=5.2 Hz, 1H), 4.48 (d, 2H), 3.70 (s, 3H), 3.60-3.52 (m, 2H), 2.97 (s, 3H), 2.78 (s, 3H), 2.67-2.60 (m, 1H), 2.24-2.22 (m, 3H), 1.79-1.52 (m, 3H), 1.46-1.35 (m, 6H); ESI MS m/z 346 [M+H]$^+$.

ALB-208787(B2-6A)

$^1$H NMR (400 MHz, CDCl$_3$) δ 7.06 (d, J=8.4 Hz, 2H), 6.79 (d, J=8.4 Hz, 2H), 4.53 (d, 2H), 3.77 (s, 3H), 3.77-3.60 (m, 2H), 2.71-2.65 (m, 1H), 2.59-2.41 (m, 2H), 2.32 (s, 6H), 2.27-2.20 (m, 1H), 1.88-1.83 (m, 2H), 1.68-1.51 (m, 3H), 1.52 (s, 3H), 1.48-1.42 (m, 3H); ESI MS m/z 332 [M+H]$^+$.

Synthesis Example 2

Synthesis of Chemical Compound B2-5A

A method for the production of chemical compound B2-5A (also called ALB-208786) is as follows (also called scheme 2).

[Chemical 48]

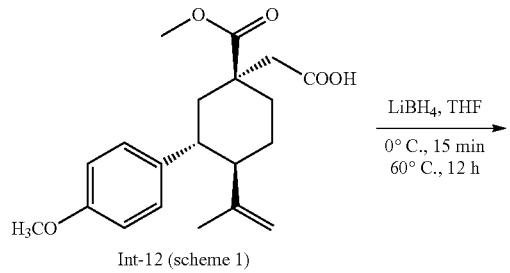

Int-12 (scheme 1)

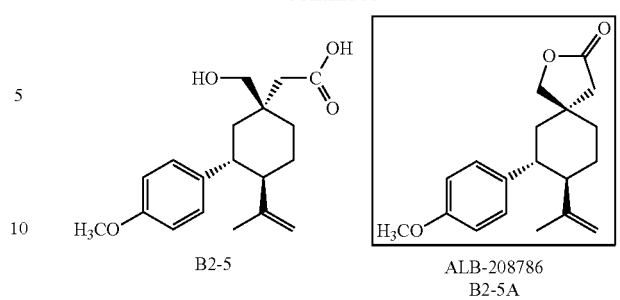

B2-5

ALB-208786
B2-5A

At 0° C., LiBH$_4$ (1.40 mL, 1.0 M in THF, 2.80 mmol) was added to an ice-cold solution of chemical compound Int-12 (chemical compound 12 in scheme 1) (0.10 g, 0.28 mmol) dissolved in THF (5.0 mL). The reaction mixture was stirred at 0° C. for 15 minutes, heated at 60° C. for 12 hours, and quenched with saturated NH$_4$Cl solution (10 mL). The obtained reaction mixture was extracted with EtOAc (10 mL×2). The extract was mixed, washed with brine (10 mL), dried over MgSO$_4$ and concentrated under reduced pressure. The crude product was purified by combiflash column chromatography using 0-70% EtOAc in hexane followed by mass triggered preparative-HPLC to obtain ALB-208786 (B2-5A) (0.005 g, 6%) as a colorless viscous substance. $^1$H NMR (400 MHz, CDCl$_3$) δ 7.03 (d, J=8.4 Hz, 2H), 6.81 (d, J=8.8 Hz, 2H), 4.57 (s, 2H), 4.31-4.27 (m, 2H), 3.78 (s, 3H), 2.53-2.46 (m, 1H), 2.35-2.23 (m, 3H), 1.93-1.88 (m, 2H), 1.81-1.77 (m, 1H), 1.67-1.53 (m, 3H), 1.51 (s, 3H); ESI MS m/z 301 [M+H]$^+$.

Synthesis Example 3

Synthesis of Chemical Compound B2-6-7

A method for the production of chemical compound B2-6-7 (also called ALB-209871) is as follows (also called scheme 3).

[Chemical 49]

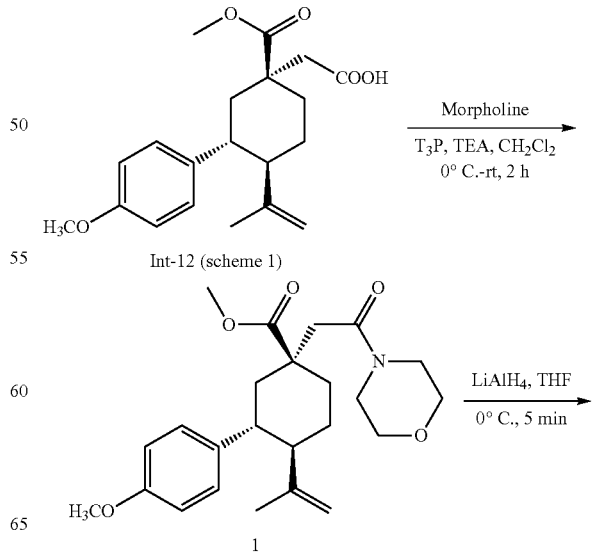

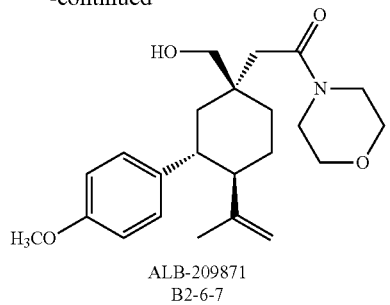

ALB-209871
B2-6-7

Production of Chemical Compound 1

At 0° C., TEA (0.04 mL, 0.29 mmol), T₃P (50% w/w in EtOAc) (0.14 mL, 0.43 mmol), and morpholine (0.02 g, 0.21 mmol) in that order were added to an ice-cold solution of chemical compound Int-12 (chemical compound 12 in scheme 1) (0.05 g, 0.14 mmol) dissolved in CH₂Cl₂ (3.0 mL). The reaction mixture was stirred at room temperature for 2 hours and diluted with H₂O (5.0 mL). The obtained reaction mixture was extracted with CH₂Cl₂ (5.0 mL×2). The organic layer was mixed, washed with brine (5.0 mL), dried over MgSO₄ and concentrated under reduced pressure. The crude product was purified by combiflash column chromatography using 0-70% EtOAc in hexane to obtain chemical compound 1 (0.055 g, 70%) as a colorless viscous material. ESI MS m/z 416 [M+H]⁺.

Production of Chemical Compound ALB-209871 (B2-6-7)

LiAlH₄ (0.10 mL, 2.0 M in THF, 0.21 mmol) was added to an ice-cold solution of chemical compound 1 (0.03 g, 0.70 mmol) dissolved in THF (3.0 mL). The reaction mixture was stirred at 0° C. for 5 minutes and diluted with saturated NH₄Cl solution (5.0 mL). The obtained reaction mixture was extracted with EtOAc (10 mL×2). The organic layer was mixed, washed with brine (5.0 mL), dried over MgSO₄ and concentrated under reduced pressure. The crude product was purified by combiflash column chromatography using 0-70% EtOAc in hexane to obtain chemical compound ALB-209871(B2-6-7) (0.002 g, 8%) as an off-white colorless viscous material. ¹H NMR (400 MHz, CDCl₃) δ 7.04 (d, J=8.4 Hz, 2H), 6.78 (d, J=8.8 Hz, 2H), 4.61-4.45 (m, 3H), 3.77-3.53 (m, 13H), 2.74-2.67 (m, 1H), 2.39-2.20 (m, 3H), 1.96-1.90 (m, 2H), 1.69-1.54 (m, 3H), 1.51 (s, 4H); ESI MS m/z 388 [M+H]⁺.

Synthesis Example 4

Synthesis of Chemical Compound B2-22

A method for the production of chemical compound B2-22 (also called ALB-210362) is as follows (also called scheme 4).

[Chemical 50]

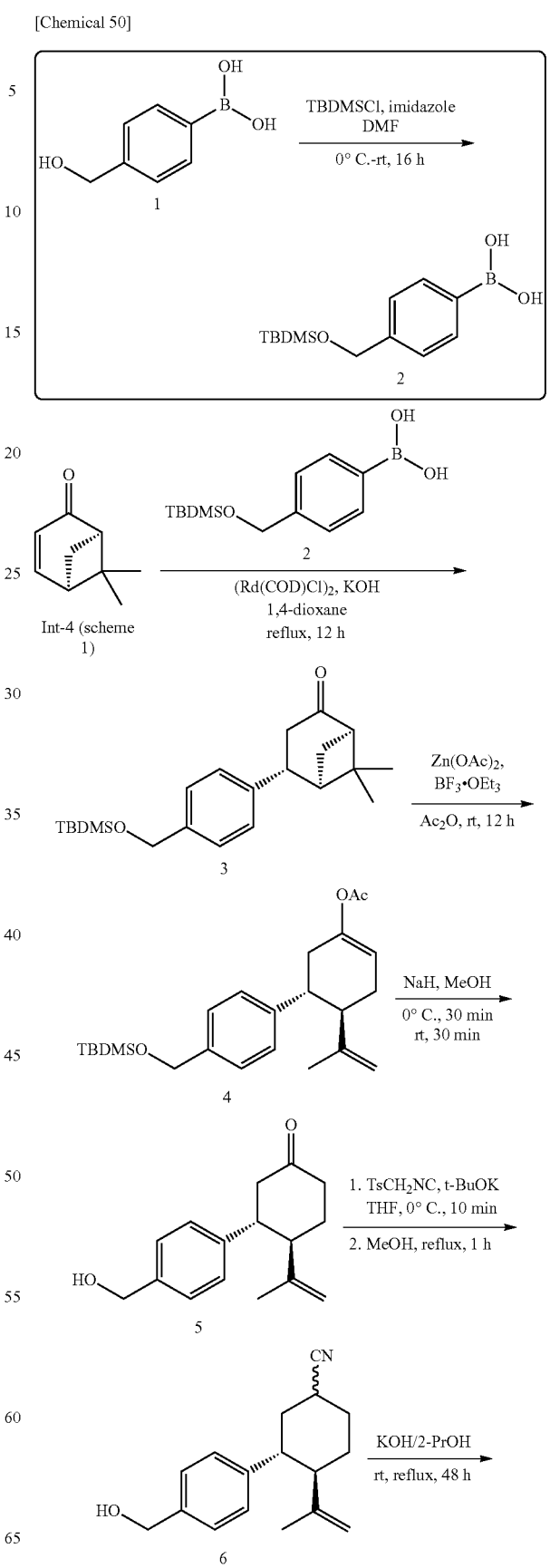

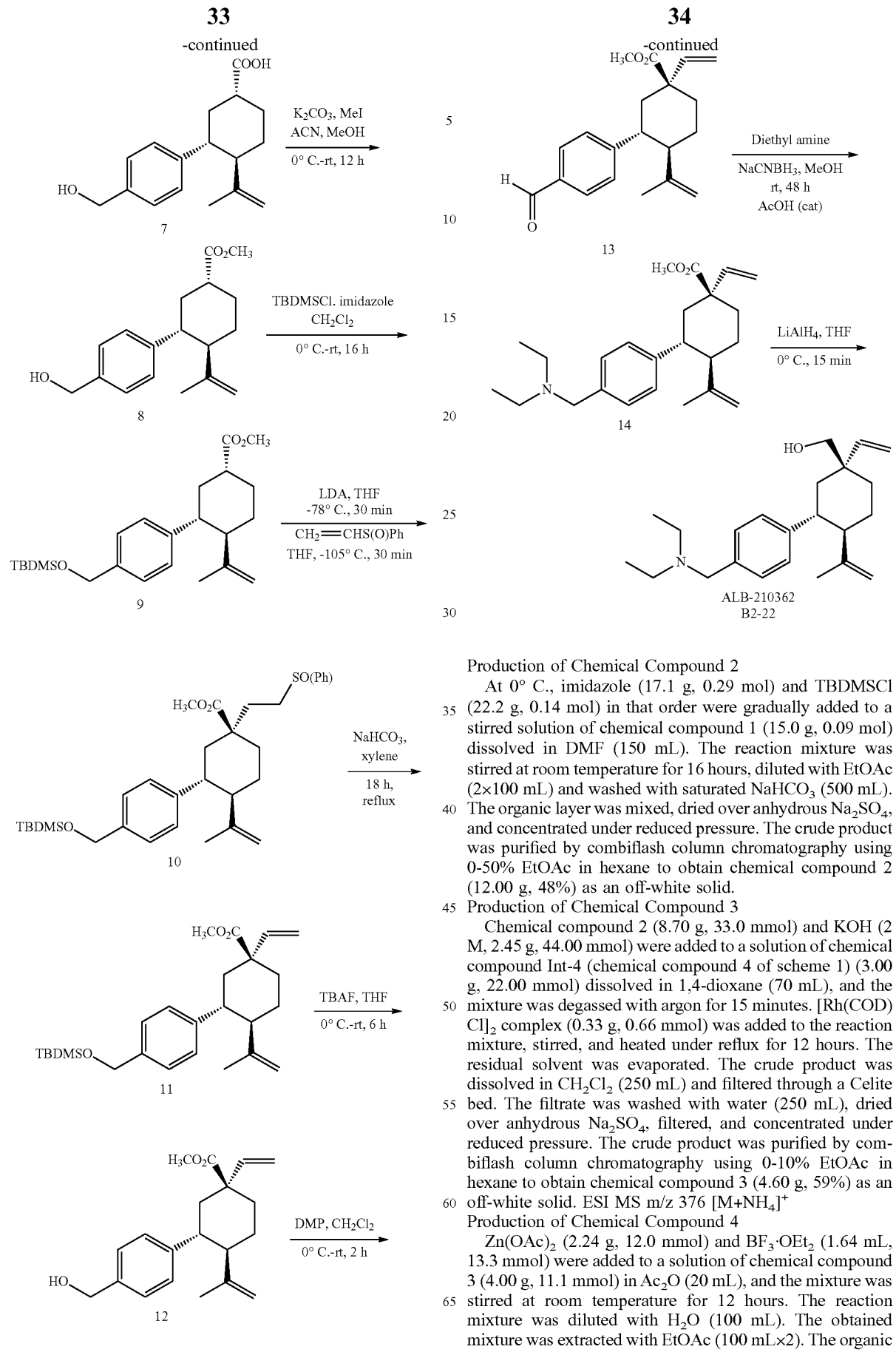

Production of Chemical Compound 2

At 0° C., imidazole (17.1 g, 0.29 mol) and TBDMSCl (22.2 g, 0.14 mol) in that order were gradually added to a stirred solution of chemical compound 1 (15.0 g, 0.09 mol) dissolved in DMF (150 mL). The reaction mixture was stirred at room temperature for 16 hours, diluted with EtOAc (2×100 mL) and washed with saturated NaHCO₃ (500 mL). The organic layer was mixed, dried over anhydrous Na₂SO₄, and concentrated under reduced pressure. The crude product was purified by combiflash column chromatography using 0-50% EtOAc in hexane to obtain chemical compound 2 (12.00 g, 48%) as an off-white solid.

Production of Chemical Compound 3

Chemical compound 2 (8.70 g, 33.0 mmol) and KOH (2 M, 2.45 g, 44.00 mmol) were added to a solution of chemical compound Int-4 (chemical compound 4 of scheme 1) (3.00 g, 22.00 mmol) dissolved in 1,4-dioxane (70 mL), and the mixture was degassed with argon for 15 minutes. [Rh(COD)Cl]₂ complex (0.33 g, 0.66 mmol) was added to the reaction mixture, stirred, and heated under reflux for 12 hours. The residual solvent was evaporated. The crude product was dissolved in CH₂Cl₂ (250 mL) and filtered through a Celite bed. The filtrate was washed with water (250 mL), dried over anhydrous Na₂SO₄, filtered, and concentrated under reduced pressure. The crude product was purified by combiflash column chromatography using 0-10% EtOAc in hexane to obtain chemical compound 3 (4.60 g, 59%) as an off-white solid. ESI MS m/z 376 [M+NH₄]⁺

Production of Chemical Compound 4

Zn(OAc)₂ (2.24 g, 12.0 mmol) and BF₃·OEt₂ (1.64 mL, 13.3 mmol) were added to a solution of chemical compound 3 (4.00 g, 11.1 mmol) in Ac₂O (20 mL), and the mixture was stirred at room temperature for 12 hours. The reaction mixture was diluted with H₂O (100 mL). The obtained mixture was extracted with EtOAc (100 mL×2). The organic layer was mixed and washed with saturated NaHCO₃ solution (250 mL) and brine (100 mL). The obtained reaction mixture was dried over MgSO₄ and concentrated under reduced pressure to obtain the residual oil. It was purified by combiflash column chromatography using 0-20% EtOAc in hexane to obtain chemical compound 4 (2.50 g, 78%) as an off-white solid.

Production of Chemical Compound 5

At 0° C. for 30 minutes, NaH (0.70 g, 60% in mineral oil, 17.4 mmol) was gradually added to a solution of chemical compound 4 (5.00 g, 17.4 mmol) dissolved in MeOH (50 mL). The reaction mixture was quenched with water (10 mL) at 0° C. MeOH in the mixture was evaporated, and the obtained solid was filtered and washed with water and then with hexane (250 mL) to obtain chemical compound 5 (3.60 g, 85%) as an off-white solid. ESI MS m/z 262 [M+NH₄]⁺.

Production of Chemical Compound 6

Chemical compound 5 (2.50 g, 10.2 mmol) dissolved in THF (5.0 mL) was added to an ice-cold solution of tert-BuOK (4.59 g, 40.9 mmol) and p-toluenesulfonylmethyl isocyanide (3.90 g, 20.4 mmol) in THF (20 mL). The mixture was stirred for 1 minute and MeOH (15 mL) was added thereto. The obtained mixture was stirred under reflux for 1 hour and concentrated under reduced pressure. The crude product was purified by combiflash column chromatography using 0-50% EtOAc in hexane to obtain chemical compound 6 (1.70 g, 65%) as a pale yellow liquid. ESI MS m/z 273 [M+NH₄]⁺.

Production of Chemical Compound 7

At room temperature, KOH (5.70 g, 101.00 mmol) was added to a solution of chemical compound 6 (2.60 g, 10.01 mmol) dissolved in 2-propanol (40 mL). The reaction mixture was stirred under reflux for 48 hours. The residual solvent was evaporated under reduced pressure. The crude product was dissolved in EtOAc (50 mL) and washed with water (50 mL). The aqueous layer was neutralized by adding HCl (2 N) and extracted with EtOAc (50 mL×2). The organic layer was mixed, washed with brine (50 mL), dried over MgSO₄ and concentrated under reduced pressure to obtain chemical compound 7 (1.30 g, 48%) as a pale yellow solid. ESI MS m/z 273 [M−H]⁺.

Production of Chemical Compound 8

At 0° C., K₂CO₃ (1.88 g, 13.50 mmol) and MeI (0.83 mL, 13.50 mmol) were dropped to a solution of chemical compound 7 (1.30 g, 4.50 mmol) dissolved in CH₃CN:MeOH (15:5 mL). The reaction mixture was stirred at room temperature for 12 hours and extracted with EtOAc (50 mL×2). The organic layer was mixed, washed with brine (50 mL), dried over MgSO₄ and concentrated under reduced pressure to obtain chemical compound 8 [1.10 g (crude)] as a brown viscous material. ESI MS m/z 271 [M+NH₄]⁺.

Production of Chemical Compound 9

At 0° C., imidazole (0.35 g, 6.00 mmol) and TBDMS-Cl (0.44 g, 2.90 mmol) in that order were gradually added to a stirred solution of chemical compound 8 (0.70 g, 2.40 mol) dissolved in CH₂Cl₂ (10 mL). The reaction mixture was heated to room temperature and stirred for 16 hours. The reaction solution was diluted with CH₂Cl₂ (2×500 mL) and washed with saturated NaHCO₃ (500 mL). The organic layer was mixed, dried over anhydrous Na₂SO₄, and concentrated under reduced pressure. The residue was purified by combiflash column chromatography using 0-10% EtOAc in hexane to obtain chemical compound 9 (0.63 g, 64%) as a colorless oil.

Production of Chemical Compound 10

At −78° C., chemical compound 9 (1.70 g, 4.20 mmol) dissolved in THF (5.0 mL) was dropped to a solution of lithium diisopropylamide (6.30 mL, 2.0 M in THF, 12.60 mmol) dissolved in THF (15 mL). The reaction mixture was stirred at −78° C. for 30 minutes, cooled to −105° C. (using MeOH, liquid N₂), and phenyl vinyl sulfoxide (1.12 mL, 8.40 mmol) was added thereto. The reaction mixture was stirred at −105° C. for 30 minutes, and saturated NH₄Cl solution (15 mL) was added to the flask. The obtained mixture was extracted with EtOAc (50 mL×2). The organic layer was mixed, washed with brine (50 mL), dried over MgSO₄ and concentrated under reduced pressure. The residue was purified by combiflash column chromatography using 0-10% EtOAc in hexane to obtain chemical compound 10 (0.80 g, 34%) as a pale yellow oil. ESI MS m/z 555 [M+H]⁺.

Production of Chemical Compound 11

A mixture of NaHCO₃ (1.20 g, 14.40 mmol) and chemical compound 10 (0.80 g, 1.44 mmol) dissolved in xylene (10 mL) was stirred under reflux for 18 hours and diluted with H₂O. The obtained mixture was extracted with EtOAc (30 mL×3). The organic layer was mixed, washed with brine (25 mL), dried over MgSO₄ and concentrated under reduced pressure to obtain the residual oil. It was purified by combiflash column chromatography using 0-20% EtOAc in hexane to obtain chemical compound 11 (0.40 g, 60%) as a colorless viscous material.

Production of Chemical Compound 12

At 0° C., TBAF (1.86 mL, 1 M in THF, 1.80 mmol) was added to an ice-cold solution of chemical compound 11 (0.40 g, 0.93 mmol) dissolved in THF (5.0 mL). The reaction mixture was stirred at room temperature for 6 hours and diluted with H₂O. The obtained mixture was extracted with EtOAc (10 mL×2). The organic layer was mixed, washed with brine (10 mL), dried over MgSO₄ and concentrated under reduced pressure to obtain the residual oil. This was purified by combiflash column chromatography using 0-30% EtOAc in hexane to obtain chemical compound 12 (0.15 g, 51%) as a colorless oil ESI MS m/z 332 [M+NH₄]⁺.

Production of Chemical Compound 13

At 0° C., Dess-Martin periodinane (0.40 g, 0.90 mmol) was added to an ice-cold solution of chemical compound 12 (0.135 g, 0.40 mmol) dissolved in CH₂Cl₂ (5.0 mL). The reaction mixture was stirred at room temperature for 2 hours. The reaction mixture was quenched with saturated Na₂S₂O₃ (5.0 mL) and saturated NaHCO₃ solution (5.0 mL), and extracted with CH₂Cl₂ (10 mL×2). The organic layer was mixed, washed with brine (10 mL), dried over MgSO₄ and concentrated under reduced pressure to obtain chemical compound 13 (0.11 g, 82%) as a colorless oil. ESI MS m/z 313 [M+H]⁺.

Production of Chemical Compound 14

At room temperature, diethylamine (0.009 g, 0.12 mmol) and NaCNBH₃ (0.016 g, 0.25 mmol) in that order were added to a solution of chemical compound 13 (0.025 g, 0.06 mmol) dissolved in MeOH (5.0 mL) and a small amount of AcOH. The reaction mixture was stirred at room temperature for 48 hours. MeOH in the mixture was evaporated under reduced pressure and diluted with H₂O. The obtained mixture was extracted with EtOAc (10 mL×2). The organic layer was mixed, washed with brine (5.0 mL), dried over MgSO₄ and concentrated under reduced pressure to obtain chemical compound 14 [0.025 g (crude)] as a colorless viscous material. ESI MS m/z 370 [M+H]⁺.

Production of Chemical Compound ALB-210362 (B2-22)

At 0° C., LiAlH₄ (0.08 mL, 2.0 M in THF, 0.16 mmol) was added to an ice-cold solution of chemical compound 14 (0.025 g, 0.06 mmol) dissolved in THF (4.0 mL). The reaction mixture was stirred at 0° C. for 15 minutes and quenched with HCl solution (2 N, 3 mL). The obtained mixture was extracted with EtOAc (5.0 mL×2). The organic layer was mixed, washed with brine (5.0 mL), dried over MgSO$_4$ and concentrated under reduced pressure. The residue was purified by mass-triggered preparative-HPLC to obtain chemical compound ALB-210362 (B2-22) (0.0055 g, 26%) as a colorless viscous material. $^1$H NMR (400 MHz, CDCl$_3$) δ 7.25 (d, J=8.0 Hz, 2H), 7.10 (d, J=8.0 Hz, 2H), 5.78-5.71 (m, 1H), 5.16-5.05 (m, 2H), 4.52 (d, 2H), 3.70-3.64 (m, 4H), 2.75-2.69 (m, 1H), 2.64-2.50 (m, 4H), 2.30-2.24 (m, 1H), 1.90-1.86 (m, 2H) 1.70-1.64 (m, 3H), 1.51 (s, 3H), 1.47-1.41 (m, 2H), 1.108 (t, J=7.2 Hz, 6H); ESI MS m/z 342 [M+H]$^+$.

Synthesis Example 5

Synthesis of Chemical Compound B2-24-1
A method for the production of chemical compound B2-24-1 (also called ALB-210798) is as follows (also called scheme 5).

[Chemical 51]

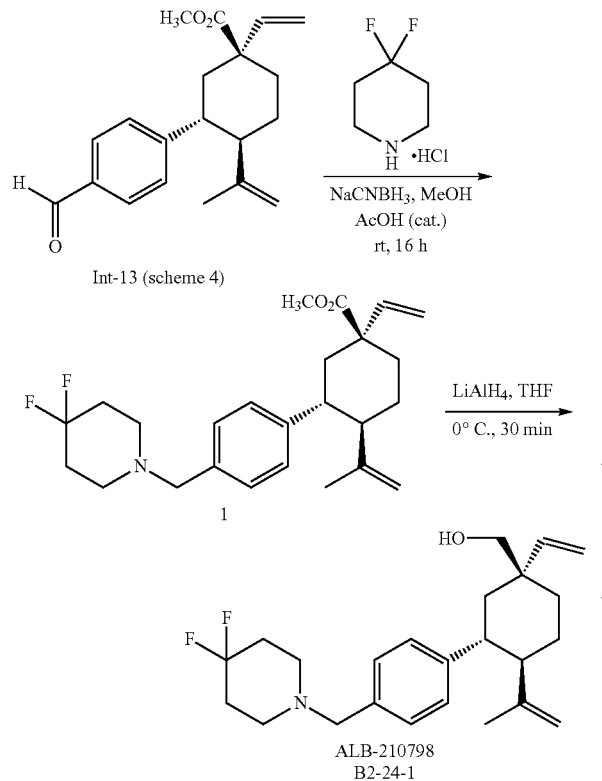

ALB-210798
B2-24-1

Production of Chemical Compound 1
At room temperature, 4,4-difluropiperdine hydrochloride (0.025 g, 0.12 mmol) and NaCNBH$_3$ (0.016 g, 0.25 mmol) in that order were added to a solution of chemical compound Int-13 (chemical compound 13 in scheme 4) (0.025 g, 0.08 mmol) dissolved in MeOH (4.0 mL) and a small amount of AcOH. The reaction mixture was stirred at room temperature for 16 hours. The MeOH in the mixture was evaporated and diluted with H$_2$O. The obtained mixture was extracted with EtOAc (10 mL×2). The organic layer was mixed and washed with brine (5.0 mL), dried over MgSO$_4$ and concentrated under reduced pressure to obtain chemical compound 1 [0.025 g (crude)] as a colorless viscous material. ESI MS m/z 418 [M+H]$^+$.

Production of Chemical Compound ALB-210798 (B2-24-1)
At 0° C., LiAlH$_4$ (0.07 mL, 2.0 M in THF, 0.14 mmol) was added to an ice-cold solution of chemical compound 1 (0.025 g, 0.05 mmol) dissolved in THF (4.0 mL). The reaction mixture was stirred at 0° C. for 30 minutes and quenched with saturated NH$_4$Cl solution (5.0 mL). The obtained mixture was extracted with EtOAc (5.0 mL×2). The organic layer was mixed, washed with brine (5.0 mL), dried over MgSO$_4$ and concentrated under reduced pressure. The residue was purified by mass-triggered preparative-HPLC to obtain chemical compound ALB-210798(B2-24-1) (0.007 g, 26%) as an off-white solid. $^1$H NMR (400 MHz, CDCl$_3$) δ 7.17 (d, J=8.0 Hz, 2H), 7.09 (d, J=8.0 Hz, 2H), 5.77-5.70 (m, 1H), 5.16-5.04 (m, 2H), 4.53 (d, 2H), 3.70 (m, 2H), 3.50 (s, 2H), 2.76-2.70 (m, 1H), 2.57-2.49 (m, 4H), 2.35-2.25 (m, 1H), 2.02-1.87 (m 6H), 1.70-1.64 (m, 2H), 1.51 (s, 3H), 1.47-1.44 (m, 2H); ESI MS m/z 390 [M+H]$^+$.

Synthesis Example 6

Synthesis of Chemical Compound B2-24-2
A method for the production of chemical compound B2-24-2 (also called ALB-210361) is as follows (also called scheme 6).

[Chemical 52]

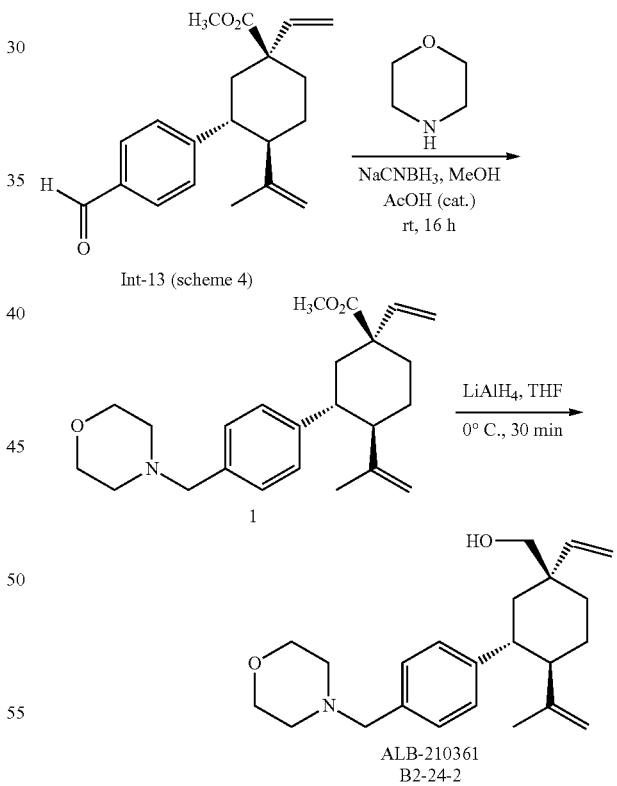

ALB-210361
B2-24-2

Production of Chemical Compound 1
At room temperature, morpholine (0.014 g, 0.12 mmol) and NaCNBH$_3$ (0.016 g, 0.25 mmol) in that order were added to a solution of chemical compound Int-13 (chemical compound 13 of scheme 4) (0.025 g, 0.08 mmol) dissolved in MeOH (4.0 mL) and a small amount of AcOH. The reaction mixture was stirred at room temperature for 16 hours. The MeOH in the mixture was evaporated and diluted with H₂O. The obtained mixture was extracted with EtOAc (10 mL×2). The organic layer was mixed, washed with brine (5.0 mL), dried over MgSO₄ and concentrated under reduced pressure to obtain chemical compound 1 [0.025 g (crude)] as a colorless viscous material. ESI MS m/z 384 [M+H]⁺.

Production of Chemical Compound ALB-210361 (B2-24-2)

At 0° C., LiAlH₄ (0.10 mL, 2.0 M in THF, 0.19 mmol) was added to an ice-cold solution of chemical compound 1 (0.025 g, 0.05 mmol) dissolved in THF (4.0 mL). The reaction mixture was stirred at 0° C. for 30 minutes and quenched with saturated NH₄Cl solution (5.0 mL). The obtained mixture was extracted with EtOAc (5.0 mL×2). The organic layer was mixed, washed with brine (5.0 mL), dried over MgSO₄ and concentrated under reduced pressure. The residue was purified by mass-triggered preparative HPLC to obtain chemical compound ALB-210361(B2-24-2) (0.007 g, 26%) as an off-white solid. ¹H NMR (400 MHz, CDCl₃) δ 7.19 (d, J=8.0 Hz, 2H), 7.09 (d, J=8.0 Hz, 2H), 5.78-5.70 (m, 1H), 5.16-5.04 (m, 2H), 4.53 (d, 2H), 3.70 (m, 6H), 3.47 (s, 2H), 2.76-2.70 (m, 1H), 2.44-2.25 (m, 5H), 1.91-1.85 (m, 2H), 1.70-1.64 (m, 3H) 1.50 (s, 3H), 1.47-1.41 (m, 2H); ESI MS m/z 356 [M+H]⁺.

Synthesis Example 7

Synthesis of Chemical Compound B2-24-3

The method for the production of chemical compound B2-24-3 (also called ALB-210795) is as follows (also called scheme 7).

[Chemical 53]

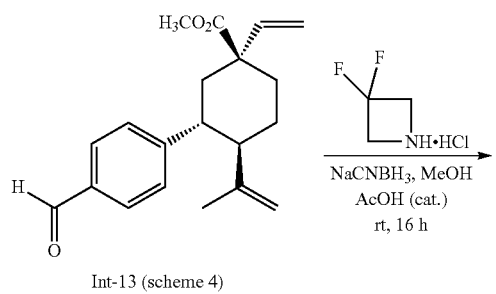

Production of Chemical Compound 1

At room temperature, 3,3-difluoroazitidine hydrochloride (0.02 g, 0.12 mmol) and NaCNBH₃ (0.016 g, 0.25 mmol) in that order were added to a solution of chemical compound Int-13 (chemical compound 13 in scheme 4) (0.025 g, 0.08 mmol) dissolved in MeOH (4.0 mL) and a small amount of AcOH. The reaction mixture was stirred at room temperature for 16 hours. The MeOH in the mixture was evaporated and diluted with H₂O. The obtained mixture was extracted with EtOAc (10 mL×2). The organic layer was mixed, washed with brine (5.0 mL), dried over MgSO₄ and concentrated under reduced pressure to obtain chemical compound 1 [0.025 g (crude)] as a colorless viscous material. ESI MS m/z 390 [M+H]⁺.

Production of Chemical Compound ALB-210795 (B2-24-3)

At 0° C., LiAlH₄ (0.08 mL, 2.0 M in THF, 0.15 mmol) was added to an ice-cold solution of chemical compound 1 (0.025 g, 0.05 mmol) dissolved in THF (4.0 mL). The reaction mixture was stirred at 0° C. for 30 minutes and quenched with saturated NH₄Cl solution (5.0 mL). The obtained mixture was extracted with EtOAc (5.0 mL×2). The organic layer was mixed, washed with brine (5.0 mL), dried over MgSO₄ and concentrated under reduced pressure. The residue was purified by mass-triggered preparative-HPLC to obtain chemical compound ALB-210795(B2-24-3) (0.005 g, 26%) as an off-white solid. ¹H NMR (400 MHz, CDCl₃) δ 7.16 (d, J=8.0 Hz, 2H), 7.09 (d, J=8.0 Hz, 2H), 5.77-5.70 (m, 1H), 5.15-5.04 (m, 2H), 4.53 (d, 2H), 3.69 (s, 2H), 3.67 (s, 2H), 3.57 (t, J=12.0 Hz, 4H), 2.76-2.69 (m, 1H), 2.30-2.24 (m, 1H), 1.91-1.87 (m, 2H), 1.70-1.64 (m, 3H), 1.50 (s, 3H), 1.47-1.41 (m, 2H); ESI MS m/z 362 [M+H]⁺.

Synthesis Example 8

Synthesis of Chemical Compound B2-24-4·HCl

A method for the production of chemical compound B2-24-4·HCl (also called ALB-210796) is as follows (also called scheme 8).

[Chemical 54]

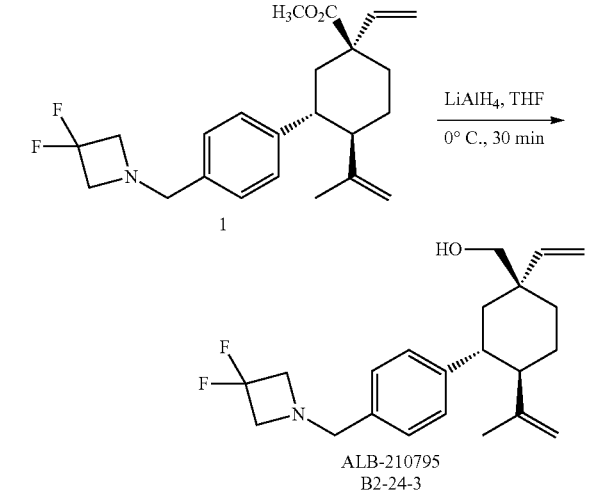
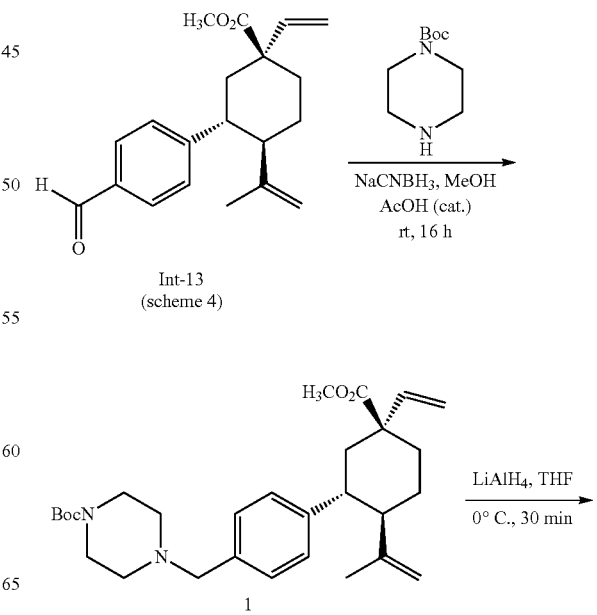

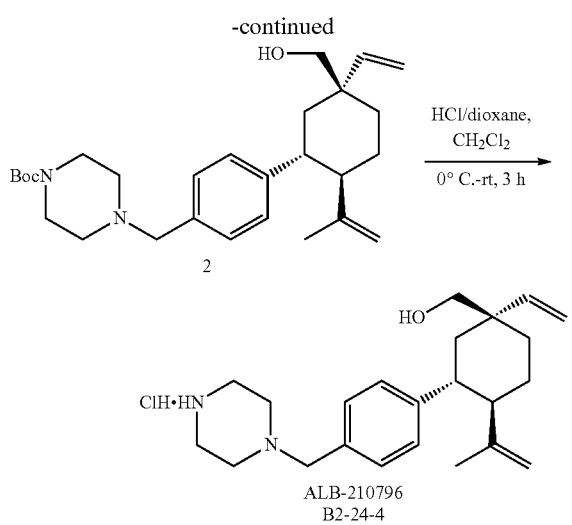

Synthesis Example 9

Synthesis of Chemical Compound B2-13

A method for the production of chemical compound B2-13 (also called ALB-209346) is as follows (also called scheme 9).

[Chemical 55]

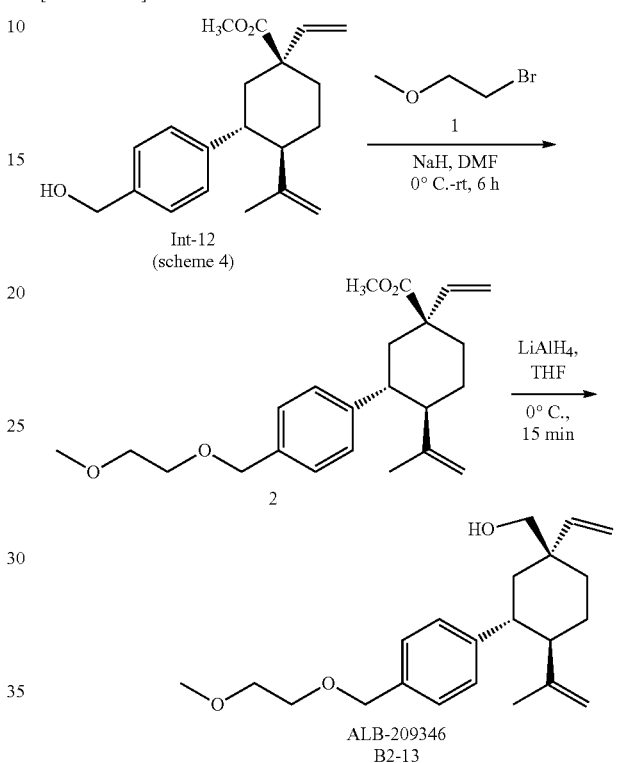

Production of Chemical Compound 1

At room temperature, tert-butyl piperzine-1-carboxylate (0.041 g, 0.22 mmol) and $NaCNBH_3$ (0.022 g, 0.30 mmol) in that order were added to a solution of chemical compound Int-13 (chemical compound 13 in scheme 4) (0.035 g, 0.11 mmol) dissolved in MeOH (5.0 mL) and a small amount of AcOH. The reaction mixture was stirred at room temperature for 16 hours. MeOH in the mixture was evaporated and diluted with $H_2O$. The obtained mixture was extracted with EtOAc (10 mL×2). The organic layer was mixed, washed with brine (5.0 mL), dried over $MgSO_4$ and concentrated under reduced pressure to obtain chemical compound 1 [0.050 g (crude)] as a colorless viscous material. ESI MS m/z 483 $[M+H]^+$.

Production of Chemical Compound 2

At 0° C., $LiAlH_4$ (0.15 mL, 2.0 M in THF, 0.31 mmol) was added to an ice-cold solution of chemical compound 1 (0.050 g, 0.10 mmol) dissolved in THF (4.0 mL). The reaction mixture was stirred at 0° C. for 30 minutes and quenched with saturated $NH_4Cl$ solution (5.0 mL). The obtained mixture was extracted with EtOAc (5.0 mL×2). The organic layer was mixed, washed with brine (5.0 mL), dried over $MgSO_4$ and concentrated under reduced pressure. The residue was purified by mass-triggered preparative-HPLC to obtain chemical compound 2 (0.005 g, 26%) as a colorless viscous material. ESI MS m/z 455 $[M+H]^+$.

Production of Chemical Compound ALB-210796 (B2-24-4·HCl)

At 0° C., dioxane·HCl (4 N, 0.5 mL) was added to an ice-cold solution of chemical compound 2 (0.050 g, 0.10 mmol) dissolved in $CH_2Cl_2$ (5.0 mL). The reaction mixture was stirred at room temperature for 3 hours. The residual solvent was evaporated under reduced pressure. The crude product was washed with 30% $CH_2Cl_2$ dissolved in hexane and purified by mass-triggered preparative HPLC to obtain chemical compound ALB-210796(B2-24-4·HCl) (0.012 g, 27%) as an off-white solid. $^1H$ NMR (400 MHz, DMSO-$d_6$) δ 7.15-7.10 (m, 4H), 5.88-5.81 (m, 1H), 4.94-4.89 (m, 2H), 4.54-4.44 (d, 2H), 3.54 (s, 2H), 3.39 (s, 2H), 2.84 (t, J=4.4 Hz, 4H), 2.78-2.67 (m, 1H), 2.37-2.27 (m, 5H), 1.77-1.51 (m, 4H), 1.49 (s, 3H), 1.41-1.25 (m, 2H); ESI MS m/z 355 $[M+H]^+$.

Production of Chemical Compound 2

At 0° C., chemical compound 1 (0.022 g, 0.15 mmol) was added to a suspension (0° C.) of NaH (0.012 g, 60% in mineral oil, 0.32 mmol) and chemical compound Int-12 (chemical compound 12 of scheme 4) (0.025 g, 0.07 mmol) dissolved in DMF (1.0 mL) to make a reaction mixture. The reaction mixture was heated to room temperature, stirred for 6 h, and quenched by the addition of HCl solution (1 N, 5.0 mL). The obtained mixture was extracted with EtOAc (10 mL×3). The organic layer was mixed, dried over $MgSO_4$ and concentrated under reduced pressure to obtain the residue. It was purified by combiflash column chromatography using 0-30% EtOAc in hexane to obtain chemical compound 2 (0.015 g, 51%) as a colorless oil. ESI MS m/z 390 $[M+NH_4]+$.

Production of Chemical Compound ALB-209346 (B2-13)

At 0° C., $LiAlH_4$ (2.0 M in THF, 0.06 mL, 0.12 mmol) was added to an ice-cold solution of chemical compound 2 (0.015 g, 0.04 mmol) dissolved in THF (5.0 mL). The reaction mixture was stirred at 0° C. for 15 minutes and quenched with saturated $NH_4Cl$ (10 mL). The obtained mixture was extracted with EtOAc (10 mL×2). The organic layer was mixed, washed with brine (5.0 mL), dried over $MgSO_4$ and concentrated under reduced pressure. The residue was purified by combiflash column chromatography using 0-50% EtOAc in hexane to obtain chemical compound ALB-209346(B2-13) (0.0085 g, 43%) as a colorless viscous material. $^1H$ NMR (400 MHz, $CDCl_3$) δ 7.23 (d, J=8.0 Hz, 2H), 7.11 (d, J=8.0 Hz, 2H), 5.77-5.70 (m, 1H), 5.15-5.04

(m, 2H), 4.54 (d, 2H), 4.51 (s, 2H), 3.69 (s, 2H), 3.69-3.57 (m, 4H), 3.38 (s, 3H), 2.77-2.70 (m, 1H), 2.33-2.26 (m, 1H), 1.91-1.84 (m, 2H), 1.70-1.60 (m, 2H), 1.52 (s, 3H), 1.48-1.41 (m, 2H); ESI MS m/z 362 [M+NH₄]⁺.

Synthesis Example 10

Synthesis of Chemical Compound B2-26

The method for the production of chemical compound B2-26 (also called ALB-209873) is as follows (also called scheme 10).

[Chemical 56]

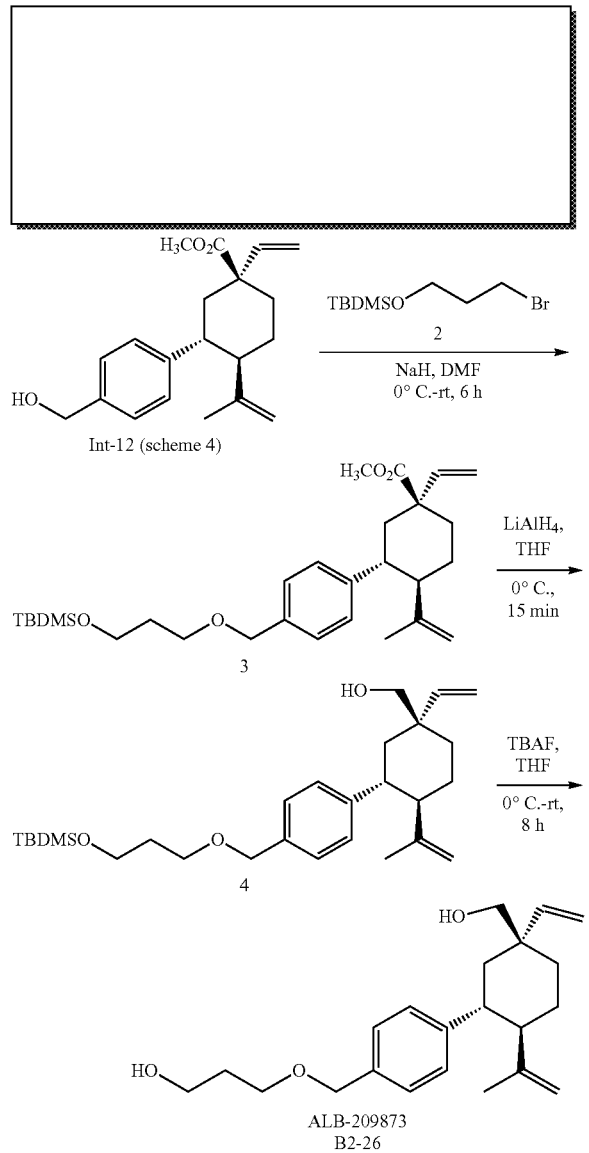

Production of Chemical Compound 2

At 0° C., imidazole (0.53 g, 9.00 mmol) and TBDMSCl (0.65 g, 4.30 mmol) in that order were gradually added to a stirred solution of chemical compound 1 (0.50 g, 3.60 mmol) dissolved in CH₂Cl₂ (10 mL). The reaction mixture was stirred at room temperature for 16 hours, diluted with CH₂Cl₂ (50 mL), washed with saturated NaHCO₃ (50 mL), dried over Na₂SO₄ and concentrated under reduced pressure.

The residue was purified by combiflash column chromatography using 0-20% EtOAc in hexane to obtain chemical compound 2 (0.5 g, 54%) as a colorless oil.

Production of Chemical Compound 3

At 0° C., NaH (0.02 g, 60% in mineral oil, 0.51 mmol) was added to a solution of chemical compound Int-12 (chemical compound 12 of scheme 4) (0.04 g, 0.13 mmol) dissolved in DMF (3.0 mL) and then the solution was stirred for 15 minutes. Chemical compound 2 (0.064 g, 0.25 mmol) was added to the reaction mixture at 0° C. The reaction was carried out at room temperature for 6 hours and quenched by the addition of HCl (2 N, 5.0 mL). The obtained mixture was extracted with EtOAc (10 mL×3), dried over MgSO₄ and concentrated under reduced pressure to obtain the residue. It was purified by combiflash column chromatography with 0-30% EtOAc in hexane to obtain chemical compound 3 (0.025 g, 40%) as a colorless oil. ESI MS m/z 487 [M+H]⁺.

Production of Chemical Compound 4

At 0° C., LiAlH₄ (2.0 M in THF, 0.08 mL, 0.15 mmol) was added to an ice-cold solution of chemical compound 3 (0.025 g, 0.05 mmol) dissolved in THF (3.0 mL). The reaction mixture was stirred at 0° C. for 15 minutes and quenched with saturated NH₄Cl (10 mL). The obtained mixture was extracted with EtOAc (10 mL×2). The organic layer was mixed, washed with brine (5.0 mL), dried over MgSO₄ and concentrated under reduced pressure. The residue was purified by combiflash column chromatography using 0-40% EtOAc in hexane to obtain chemical compound 4 (0.02 g, 85%) as a colorless oil.

Production of Chemical Compound ALB-209873 (B2-26)

At 0° C., TBAF (0.08 mL, 1 M in THF, 0.08 mmol) was added to an ice-cold solution of chemical compound 4 (0.02 g, 0.04 mmol) dissolved in THF (2.0 mL). The reaction mixture was stirred at room temperature for 8 hours and diluted with H₂O (5.0 mL). The obtained mixture was extracted with EtOAc (10 mL×2). The extract was mixed, washed with brine (5.0 mL), dried over MgSO₄ and concentrated under reduced pressure to obtain the residual oil. It was purified by combiflash column chromatography using 0-50% EtOAc in hexane to obtain chemical compound ALB-209873(B2-26) (0.009 g, 60%) as a colorless viscous material. ¹H NMR (400 MHz, CDCl₃) δ 7.21 (d, J=8.0 Hz, 2H), 7.12 (d, J=8.0 Hz, 2H), 5.77-5.70 (m, 1H), 5.15-5.04 (m, 2H), 4.54 (d, 2H), 4.47 (s, 2H), 3.78 (t, J=5.6 Hz, 2H), 3.70 (s, 2H), 3.65 (t, J=6.0 Hz, 2H), 2.75-2.71 (m, 1H), 2.33-2.26 (m, 1H), 1.91-1.83 (m, 4H), 1.70-1.60 (m, 2H), 1.52 (s, 3H), 1.48-1.41 (m, 2H); ESI MS m/z 362 [M+NH₄]⁺.

Synthesis Example 11

Synthesis of Chemical Compound B2-24

The method for the production of chemical compound B2-24 (also called ALB-209348) is as follows (also called scheme 11).

[Chemical 57]

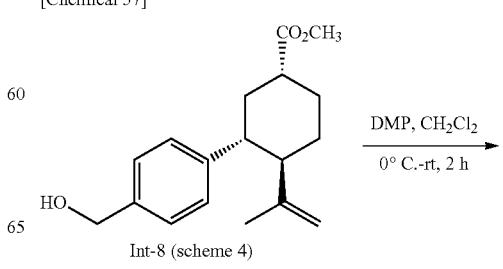

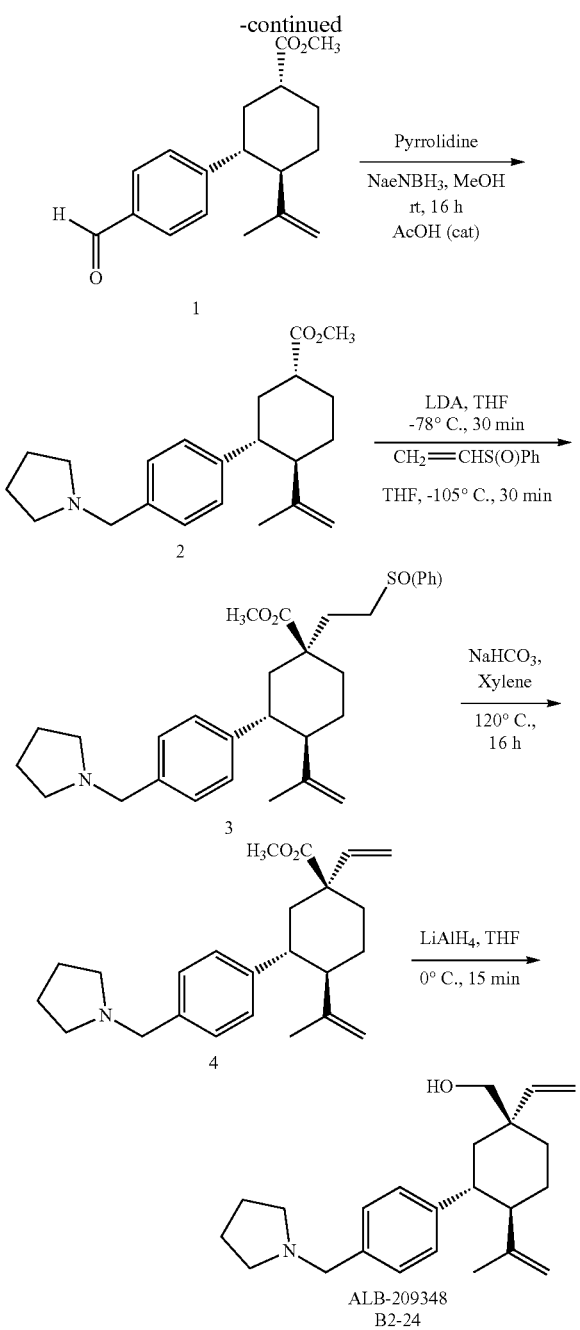

1

2

3

4

ALB-209348
B2-24

Production of Chemical Compound 1

At 0° C., Dess-Martin periodiane (0.82 g, 1.90 mmol) was added to an ice-cold solution of chemical compound Int-8 (chemical compound 8 of scheme 4) (0.28 g, 0.97 mmol) dissolved in $CH_2Cl_2$ (10 mL). The reaction mixture was heated to room temperature and stirred at the same temperature for 2 hours. The reaction mixture was quenched with saturated $Na_2S_2O_3$ solution (5.0 mL), saturated $NaHCO_3$ solution (5.0 mL) and extracted with $CH_2Cl_2$ (10 mL×2). The organic layer was mixed, washed with brine (5.0 mL), dried over $MgSO_4$ and concentrated under reduced pressure to obtain chemical compound 1 (0.2 g, 72%) as a colorless oil. ESI MS m/z 287 $[M+H]^+$.

Production of Chemical Compound 2

At room temperature, pyrrolidine (0.10 mL, 1.30 mmol) and $NaCNBH_3$ (0.13 g, 2.08 mmol) in that order were added to a solution of chemical compound 1 (0.2 g, 0.69 mmol) dissolved in MeOH (5.0 mL) and a small amount of AcOH. The reaction mixture was stirred at room temperature for 16 hours. MeOH in the mixture was evaporated and diluted with $H_2O$. The obtained mixture was extracted with EtOAc (10 mL×2). The organic layer was mixed, washed with brine (10 mL), dried over $MgSO_4$ and concentrated under reduced pressure to obtain the residual oil. It was purified by combiflash column chromatography using 0-90% EtOAc in hexane to obtain chemical compound 2 (0.15 g, 63%) as a colorless viscous material. ESI MS m/z 342 $[M+H]^+$.

Production of Chemical Compound 3

At −78° C., chemical compound 2 (0.15 g, 0.43 mmol) dissolved in THF (4.0 mL) was dropped to a solution of lithium diisopropylamide (0.65 mL, 2.0 M in THF, 1.30 mmol) dissolved in THF (5.0 mL). The solution was stirred at −78° C. for 30 minutes, and then cooled to −105° C. (MeOH, liquid $N_2$), and phenyl vinyl sulfoxide (0.12 mL, 0.87 mmol) was added thereto. The reaction mixture was stirred at −105° C. for 30 minutes and quenched with saturated $NH_4Cl$ solution (15 mL). The obtained mixture was extracted with EtOAc (20 mL×2). The organic layer was mixed, washed with brine (10 mL), dried over $MgSO_4$ and concentrated under reduced pressure to obtain chemical compound 3 [0.2 g (crude)] as a brown oil. ESI MS m/z 494 $[M+H]^+$.

Production of Chemical Compound 4

A solution of $NaHCO_3$ (0.34 g, 4.00 mmol) and chemical compound 3 [0.20 g (crude), 0.40 mmol] dissolved in xylene (5.0 mL) was stirred under reflux for 16 hours and diluted with $H_2O$. The obtained mixture was extracted with EtOAc (30 mL×3). The organic layer was mixed, washed with brine (5.0 mL), dried over $MgSO_4$ and concentrated under reduced pressure to obtain chemical compound 4 [0.10 g (crude)] as a brown liquid. ESI MS m/z 368 $[M+H]^+$.

Production of Chemical Compound ALB-209348 (B2-24)

At 0° C., $LiAlH_4$ (0.18 mL, 2.0 M in THF, 0.36 mmol) was added to an ice-cold solution of chemical compound 4 (0.06 g, 0.12 mmol) dissolved in THF (2.0 mL). The reaction mixture was stirred at 0° C. for 15 minutes and quenched with saturated $NH_4Cl$ solution (5.0 mL). The obtained mixture was extracted with EtOAc (5.0 mL×2). The organic layer was mixed, washed with brine (5.0 mL), dried over $MgSO_4$ and concentrated under reduced pressure. The residue was purified by mass-triggered preparative-HPLC to obtain chemical compound ALB-209348(B2-24) (0.007 g, 8%) as a colorless viscous material. $^1$H NMR (400 MHz, $CDCl_3$) δ 7.31 (d, J=8.0 Hz, 2H), 7.21 (d, J=8.0 Hz, 2H), 5.78-5.71 (m, 1H), 5.17-5.05 (m, 2H), 4.52 (d, 2H), 4.03-3.99 (m, 2H), 3.80-3.63 (m, 3H), 3.09-3.05 (m, 3H), 2.79-2.74 (m, 1H), 2.31-2.25 (m, 1H), 2.08-2.04 (m, 4H), 1.91-1.87 (m, 3H), 1.70-1.64 (m, 2H), 1.51 (s, 3H), 1.48-1.41 (m, 2H); ESI MS m/z 340 $[M+H]^+$.

Synthesis Example 12

Synthesis of Chemical Compound B2-5A-9

A method for the production of chemical compound B2-5A-9 (also called ALB-210799) is as follows (also called scheme 12).

[Chemical 58]

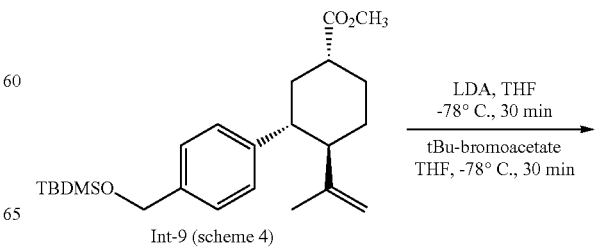

Int-9 (scheme 4)

-continued

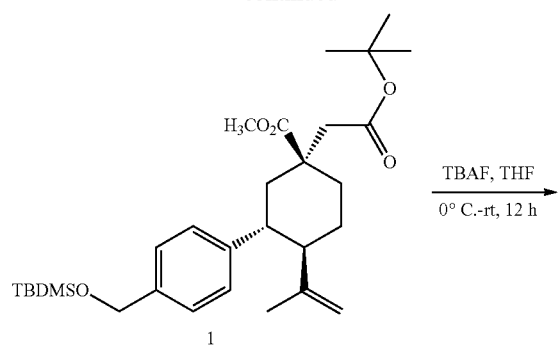

TBAF, THF
0° C.-rt, 12 h

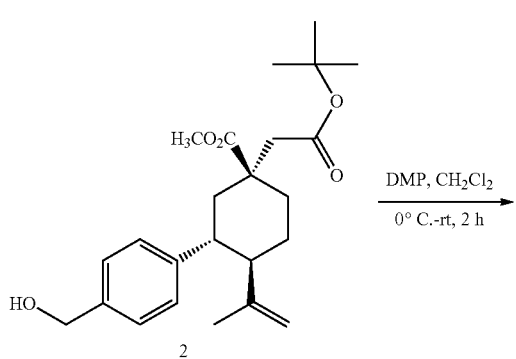

DMP, CH₂Cl₂
0° C.-rt, 2 h

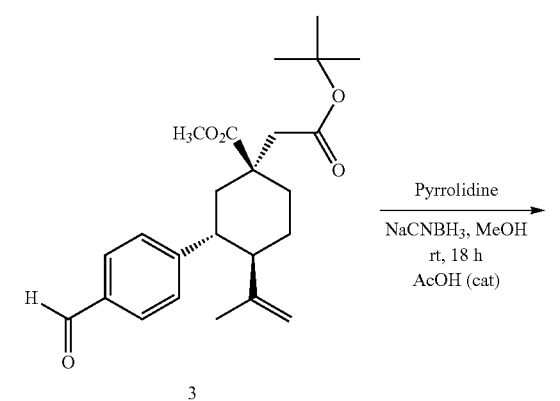

Pyrrolidine
NaCNBH₃, MeOH
rt, 18 h
AcOH (cat)

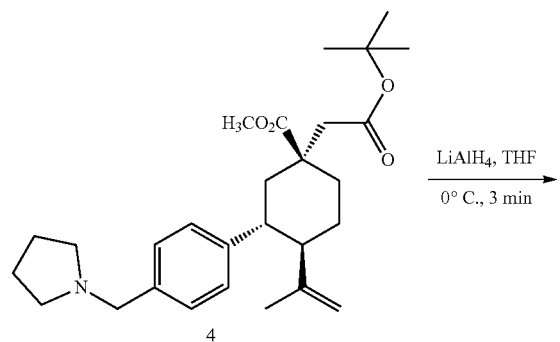

LiAlH₄, THF
0° C., 3 min

-continued

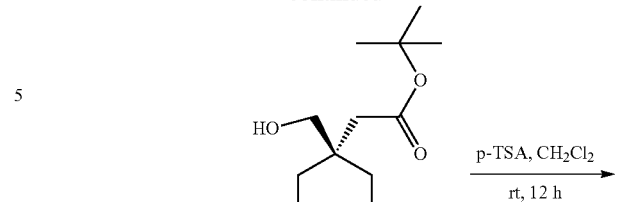

p-TSA, CH₂Cl₂
rt, 12 h

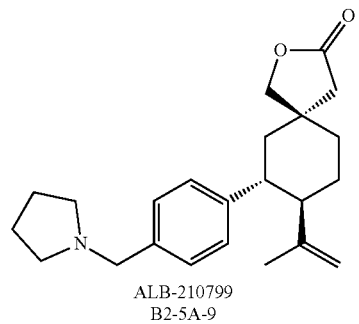

ALB-210799
B2-5A-9

Production of Chemical Compound 1

At −78° C., chemical compound Int-9 (chemical compound 9 in scheme 4) [1.0 g (crude), 2.48 mmol] dissolved in THF (4.0 mL) was dropped to a solution of lithium diisopropylamide (3.73 mL, 2.0 M in THF, 7.40 mmol) dissolved in THF (6.0 mL). The solution was stirred at −78° C. for 30 minutes, and tert-butyl 2-bromoacetate (1.00 mL, 4.90 mmol) was added to the reaction mixture. The reaction mixture was stirred at −78° C. for 30 minutes and quenched with saturated NH₄Cl solution (15 mL). The obtained mixture was extracted with EtOAc (50 mL×2). The organic layer was mixed, washed with brine (25 mL), dried over Na₂SO₄ and concentrated under reduced pressure to obtain chemical compound 1 [0.90 g (crude)] as a brown liquid.

Production of Chemical Compound 2

At 0° C., TBAF (5.20 mL, 1 M in THF, 5.20 mmol) was added to an ice-cold solution of chemical compound 10 (0.90 g, 1.70 mmol) dissolved in THF (15 mL). The reaction mixture was stirred at room temperature for 12 hours and diluted with H₂O. The obtained mixture was extracted with EtOAc (50 mL×2). The organic layer was mixed, washed with brine (25 mL), dried over MgSO₄ and concentrated under reduced pressure to obtain the residual oil. It was purified by combiflash column chromatography using 0-30% EtOAc in hexane to obtain chemical compound 2 (0.40 g, 40%) as a colorless viscous material.

Production of Chemical Compound 3

At 0° C., Dess-Martin periodinane (0.32 g, 0.80 mmol) was added to an ice-cold solution of chemical compound 2 (0.15 g, 0.40 mmol) dissolved in CH₂Cl₂ (5.0 mL). The reaction mixture was stirred at room temperature for 2 hours. The reaction mixture was quenched with saturated Na₂S₂O₃ (10 mL) solution and saturated NaHCO₃ (10 mL) solution and extracted with CH₂Cl₂ (10 mL×2). The organic layer was mixed, washed with brine (10 mL), dried over MgSO₄ and concentrated under reduced pressure to obtain chemical compound 3 [0.15 g (crude)] as a colorless oil.

Production of Chemical Compound 4

At room temperature, pyrrolidine (0.06 g, 7.50 mmol) and NaCNBH$_3$ (0.07 g, 1.13 mmol) in that order were added to a solution of chemical compound 3 (0.15 g, 3.70 mmol) dissolved in MeOH (5.0 mL) and a small amount of AcOH. The reaction mixture was stirred at room temperature for 18 hours. MeOH in the mixture was evaporated and diluted with H$_2$O. The obtained mixture was extracted with EtOAc (10 mL×2). The organic layer was mixed, washed with brine (10 mL), dried over MgSO$_4$ and concentrated under reduced pressure to obtain the colorless oil. It was purified by combiflash column chromatography using 0-90% EtOAc in hexane to obtain chemical compound 4 (0.15 g, 88%) as a colorless viscous material. ESI MS m/z 456 [M+H]$^+$.

Production of Chemical Compound 5

At 0° C., LiAlH$_4$ (2.0 M in THF, 0.90 mL, 0.85 mmol) was added to an ice-cold solution of chemical compound 4 (0.13 g, 0.28 mmol) dissolved in THF (4.0 mL). The reaction mixture was stirred at 0° C. for 3 minutes and quenched with saturated NH$_4$Cl solution (5.0 mL). The obtained mixture was extracted with EtOAc (10 mL×2). The organic layer was mixed, washed with brine (15 mL), dried over MgSO$_4$ and concentrated under reduced pressure to obtain chemical compound 5 [0.08 g (crude)] as a colorless oil. ESI MS m/z 428 [M+H]$^+$.

Production of Chemical Compound ALB-210799 (B2-5A-9)

At room temperature, p-toluenesulfonic acid (0.040 g, 0.37 mmol) was added to a solution of chemical compound 5 (0.08 g, 0.18 mmol) dissolved in CH$_2$Cl$_2$ (5.0 mL). The reaction mixture was stirred at room temperature for 12 hours. The reaction mixture was quenched with saturated NaHCO$_3$ solution (10 mL) and extracted with CH$_2$Cl$_2$ (10 mL×2). The organic layer was mixed, washed with brine (10 mL), dried over MgSO$_4$ and concentrated under reduced pressure. The residue was purified by mass-triggered preparative-HPLC to obtain chemical compound ALB-210799 (B2-5A-9) (0.00775 g, 8%) as an off-white solid. $^1$H NMR (400 MHz, CDCl$_3$) δ 7.22 (d, J=8.0 Hz, 2H), 7.04 (d, J=8.0 Hz, 2H), 4.55 (s, 2H), 4.28 (q, J=8.0 Hz, 2H), 3.58 (s, 2H), 2.56-2.50 (m, 5H), 2.35-2.25 (m, 3H), 1.93-1.89 (m, 2H), 1.82-1.78 (m, 5H), 1.70-1.53 (m, 3H), 1.48 (s, 3H); ESI MS m/z 354 [M+H]$^+$.

Synthesis Example 13

Synthesis of Chemical Compound B2-5A-6

A method for the production of chemical compound B2-5A-6 (also called ALB-211297) is as follows (also called scheme 13).

[Chemical 59]

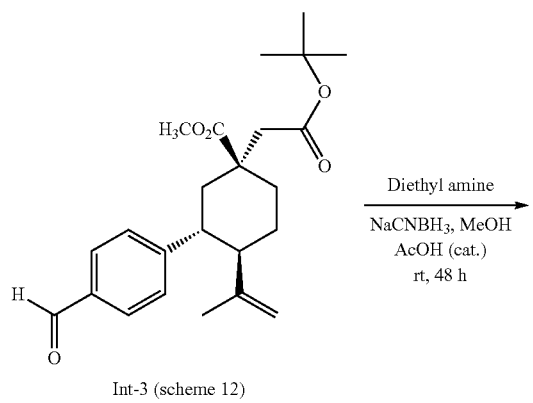

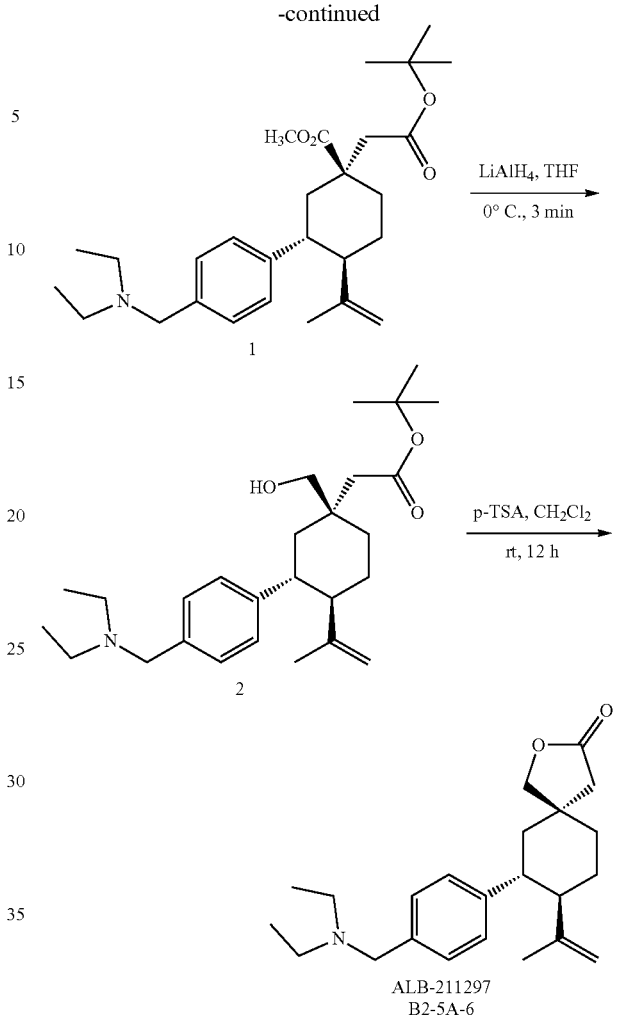

Production of Chemical Compound 1

At room temperature, diethylamine (0.05 g, 0.50 mmol) and NaCNBH$_3$ (0.05 g, 0.75 mmol) in that order were added to a solution of chemical compound Int-3 (chemical compound 3 in scheme 12) (0.10 g, 0.25 mmol) dissolved in MeOH (5.0 mL) and a small amount of AcOH. The reaction mixture was stirred at room temperature for 48 hours. MeOH in the mixture was evaporated and diluted with H$_2$O. The obtained mixture was extracted with EtOAc (10 mL×2). The organic layer was mixed, washed with brine (10 mL), dried over MgSO$_4$ and concentrated under reduced pressure to obtain the colorless oil. It was purified by combiflash column chromatography using 0-90% EtOAc in hexane to obtain chemical compound 1 (0.06 g, 52%) as a colorless viscous material. ESI MS m/z 458 [M+H]$^+$.

Production of Chemical Compound 2

At 0° C., LiAlH$_4$ (2.0 M in THF, 0.39 mL, 0.39 mmol) was added to an ice-cold solution of chemical compound 1 (0.06 g, 0.13 mmol) dissolved in THF (4.0 mL). The reaction mixture was stirred at 0° C. for 3 minutes and quenched with saturated NH$_4$Cl (5.0 mL). The obtained mixture was extracted with EtOAc (10 mL×2). The organic layer was mixed, washed with brine (5.0 mL), dried over MgSO$_4$ and concentrated under reduced pressure to obtain chemical compound 2 [0.05 g (crude)] as a colorless oil. ESI MS m/z 430 [M+H]$^+$.

Production of Chemical Compound ALB-211297 (B2-5A-6)

At room temperature, p-toluenesulfonic acid (0.03 g, 0.23 mmol) was added to a solution of chemical compound 2 (0.05 g, 0.11 mmol) dissolved in $CH_2Cl_2$ (5.0 mL). The reaction mixture was stirred at room temperature for 12 hours. The reaction mixture was quenched with saturated $NaHCO_3$ solution (5.0 mL) and extracted with $CH_2Cl_2$ (10 mL×2). The organic layer was mixed, washed with brine (5.0 mL), dried over $MgSO_4$ and concentrated under reduced pressure. The residue was purified by mass-triggered preparative HPLC to obtain chemical compound ALB-211297 (B2-5A-6) (0.0075 g, 8%) as an off-white solid. $^1$H NMR (400 MHz, $CDCl_3$) δ 7.22-7.20 (d, J=8.0 Hz, 2H), 7.05-7.03 (d, J=8.0 Hz, 2H), 4.55 (s, 2H), 4.28 (q, J=8.0 Hz, 2H), 3.51 (s, 2H), 2.53-2.48 (m, 5H), 2.35-2.25 (m, 3H), 1.93-1.90 (m, 2H), 1.81-1.77 (m, 1H), 1.70-1.53 (m, 3H), 1.49 (s, 3H), 1.03 (t, 6H). ESI MS m/z 356 [M+H]$^+$.

Synthesis Example 14

Synthesis of Chemical Compound B2-5A-4

A method for the production of chemical compound B2-5A-4 (also called ALB-211299) is as follows (also called scheme 14).

[Chemical 60]

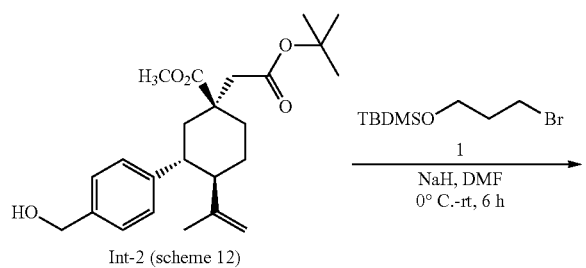

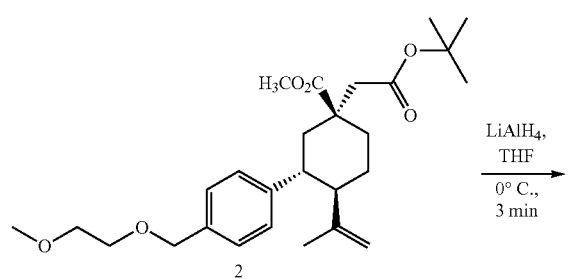

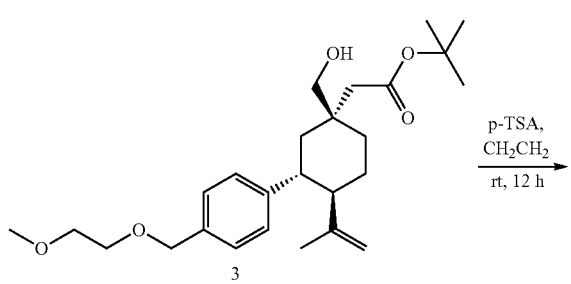

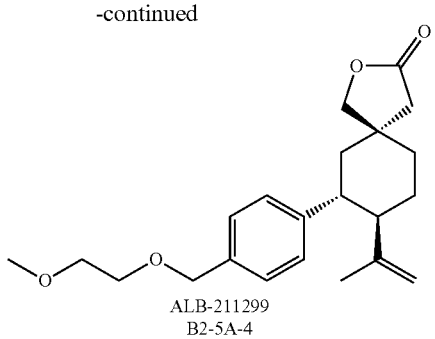

ALB-211299
B2-5A-4

Production of Chemical Compound 2

At 0° C., chemical compound 1 (0.037 g, 0.39 mmol) was added to a suspension of NaH (0.016 g, 60% in mineral oil, 0.39 mmol) and chemical compound Int-2 (chemical compound 2 in scheme 12) (0.08 g, 0.19 mmol) dissolved in DMF (3.0 mL) to form a reaction mixture. The reaction was carried out at room temperature for 6 hours and quenched by the addition of saturated $NH_4Cl$ solution (5.0 mL). The obtained mixture was extracted with EtOAc (10 mL×3). The organic layer was mixed, dried over $MgSO_4$ and concentrated under reduced pressure to obtain the residue. It was purified by combiflash column chromatography using 0-30% EtOAc in hexane to obtain chemical compound 2 (0.04 g, 50%) as a colorless oil. ESI MS m/z 478 [M+NH$_4$]$^+$.

Production of Chemical Compound 3

At 0° C., LiAlH$_4$ (2.0 M in THF, 0.26 mL, 0.26 mmol) was mixed with an ice-cold solution of chemical compound 2 (0.04 g, 0.08 mmol) dissolved in THF (4.0 mL). The reaction mixture was stirred at 0° C. for 3 minutes and quenched with saturated $NH_4Cl$ solution (5.0 mL). The obtained mixture was extracted with EtOAc (10 mL×2). The organic layer was mixed, washed with brine (5.0 mL), dried over $MgSO_4$ and concentrated under reduced pressure to obtain chemical compound 3 (0.018 g, 49%) as a colorless oil. ESI MS m/z 450 [M+NH$_4$]$^+$.

Production of Chemical Compound ALB-211299 (B2-5A-4)

At room temperature, p-toluenesulfonic acid (0.007 g, 0.08 mmol) was added to a solution of chemical compound 3 (0.018 g, 0.04 mmol) dissolved in $CH_2Cl_2$ (5.0 mL). The reaction mixture was stirred at room temperature for 12 hours. The reaction mixture was quenched with saturated $NaHCO_3$ solution (5.0 mL) and extracted with $CH_2Cl_2$ (10 mL×2). The organic layer was mixed, washed with brine (5.0 mL), dried over $MgSO_4$ and concentrated under reduced pressure. The residue was purified by mass-triggered preparative HPLC to obtain chemical compound ALB-211299 (B2-5A-4) (0.012 g, 72%) as an off-white solid. $^1$H NMR (400 MHz, $CDCl_3$) δ 7.27 (d, J=8.0 Hz, 2H), 7.10 (d, J=8.0 Hz, 2H), 4.58 (d, J=4.0 Hz, 2H), 4.54 (s, 2H), 4.31 (q, J=8.0 Hz, 2H), 3.64-3.62 (m, 2H), 3.60-3.58 (m, 2H), 3.41 (s, 3H), 2.60-2.53 (m, 1H), 2.37-2.29 (m, 3H), 1.96-1.89 (m, 2H), 1.84-1.80 (m, 1H), 1.70-1.60 (m, 3H), 1.50 (s, 3H); ESI MS m/z 376 [M+NH$_4$]$^+$.

Synthesis Example 15

Synthesis of Chemical Compound B2-29

A method for the production of chemical compound B2-29 (also called ALB-210364) is as follows (also called scheme 15).

[Chemical 61]

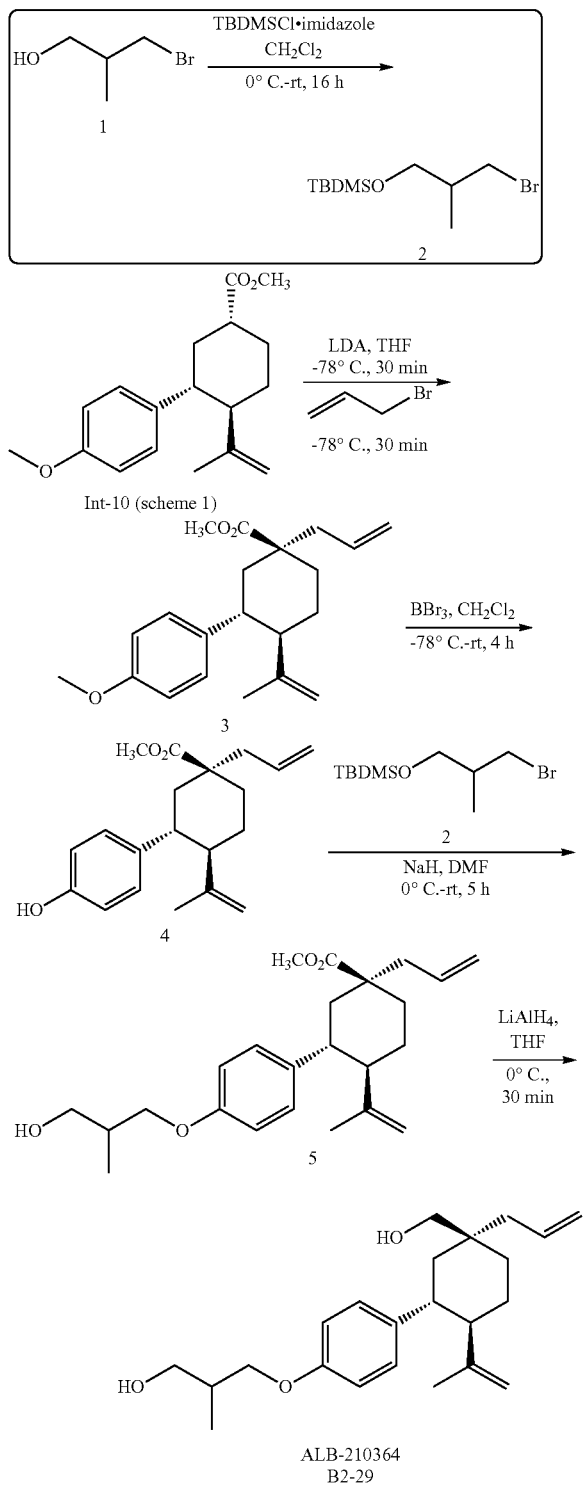

Production of Chemical Compound 2

At 0° C., imidazole (0.55 g, 8.16 mmol) and TBDMSCl (0.59 g, 3.92 mmol) in that order were added to a solution of chemical compound 1 (0.50 g, 3.27 mmol) dissolved in $CH_2Cl_2$ (10 mL). The reaction mixture was stirred at room temperature for 16 hours, diluted with $CH_2Cl_2$ (25 mL), and washed with saturated $NaHCO_3$ (20 mL). The reaction mixture was dried over $Na_2SO_4$ and concentrated under reduced pressure. The residue was purified by combiflash column chromatography using 0-40% EtOAc in hexane to obtain chemical compound 2 (0.50 g, 57%) as a colorless liquid.

Production of Chemical Compound 3

At −78° C., LDA (1.04 mL, 2.0 M in THF, 2.08 mmol) was dropped to an ice-cold solution of chemical compound Int-10 (chemical compound 10 in scheme 1) (0.20 g, 0.69 mmol) dissolved in THF (5.0 mL). The solution was stirred at −78° C. for 30 minutes. Allyl bromide (0.18 g, 1.39 mmol) was added to the reaction mixture. The mixture was stirred at −78° C. for 30 minutes. The reaction mixture was quenched with saturated $NH_4Cl$ solution (10 mL). The obtained mixture was extracted with EtOAc (20 mL×3). The organic layer was mixed, washed with brine (10 mL), dried over $MgSO_4$ and concentrated. The residue was purified by combiflash column chromatography using 0-20% EtOAc in hexane to obtain chemical compound 3 (0.18 g, 79%) as a pale yellow liquid.

Production of Chemical Compound 4

At −78° C., $BBr_3$ (1 M in $CH_2Cl_2$) (1.60 mL, 1.64 mmol) was added to a stirred solution of chemical compound 3 (0.18 g, 0.55 mmol) dissolved in $CH_2Cl_2$ (5.0 mL). The reaction mixture was gradually heated from −78° C. to room temperature over 4 hours. The reaction mixture was concentrated under reduced pressure to obtain the residue. It was purified by combiflash column chromatography using 0-60% EtOAc in hexane to obtain chemical compound 4 (0.035 g, 20%) as a colorless oil.

Production of Chemical Compound 5

At 0° C., NaH (0.01 g, 60% in mineral oil, 0.28 mmol) was added to a stirred solution of chemical compound 4 (0.035 g, 0.11 mmol) dissolved in DMF (3.0 mL) and the solution was stirred for 5 minutes. After 5 minutes, chemical compound 2 (0.04 g, 0.14 mmol) was added to the reaction mixture. The mixture was stirred at room temperature for 5 hours and diluted with cold $H_2O$ (20 mL). The obtained mixture was extracted with EtOAc (30 mL×2). The extract was mixed, washed with brine (20 mL), dried over $Na_2SO_4$ and concentrated under reduced pressure. The residue was purified by combiflash column chromatography using 0-40% EtOAc in hexane to obtain chemical compound 5 (0.02 g, 46%) as a colorless liquid.

Production of Chemical Compound ALB-210364 (B2-29)

At 0° C., $LiAlH_4$ (0.07 mL, 2.0 M in THF, 0.16 mmol) was added to an ice-cold solution of chemical compound 5 (0.02 g, 0.05 mmol) dissolved in THF (4.0 mL). The reaction mixture was stirred at 0° C. for 30 minutes and diluted with $H_2O$ and $Na_2SO_4 \cdot 10H_2O$. The obtained mixture was extracted with EtOAc (10 mL×3). The extract was mixed, washed with brine (5.0 mL), dried with $Na_2SO_4$ and concentrated under reduced pressure. The residue was purified by combiflash column chromatography using 0-60% EtOAc in hexane to obtain chemical compound ALB-210364(B2-29) (0.0039 g, 21%) as a colorless viscous material. $^1H$ NMR (400 MHz, $CDCl_3$) δ 7.03 (d, J=8.4 Hz, 2H), 6.79 (d, J=8.8 Hz, 2H), 5.93-5.83 (m, 1H), 5.09-5.04 (m, 2H), 4.53 (d, J=5.6 Hz, 2H), 3.95-3.85 (m, 2H), 3.68 (t, J=4.4 Hz, 4H), 2.66-2.59 (m, 1H), 2.23-2.14 (m, 2H), 2.07-1.99 (m, 2H), 1.76 (d, J=13.6 Hz, 2H), 1.62-1.58 (m, 5H), 1.49 (s, 3H), 1.38-1.28 (m, 2H), 1.01 (d, J=7.6 Hz, 3H). ESI MS m/z 359 [M+H]$^+$.

Synthesis Example 16

Synthesis of Chemical Compound B2-28

A method for the production of chemical compound B2-28 (also called ALB-210359) is as follows (also called scheme 16).

[Chemical 62]

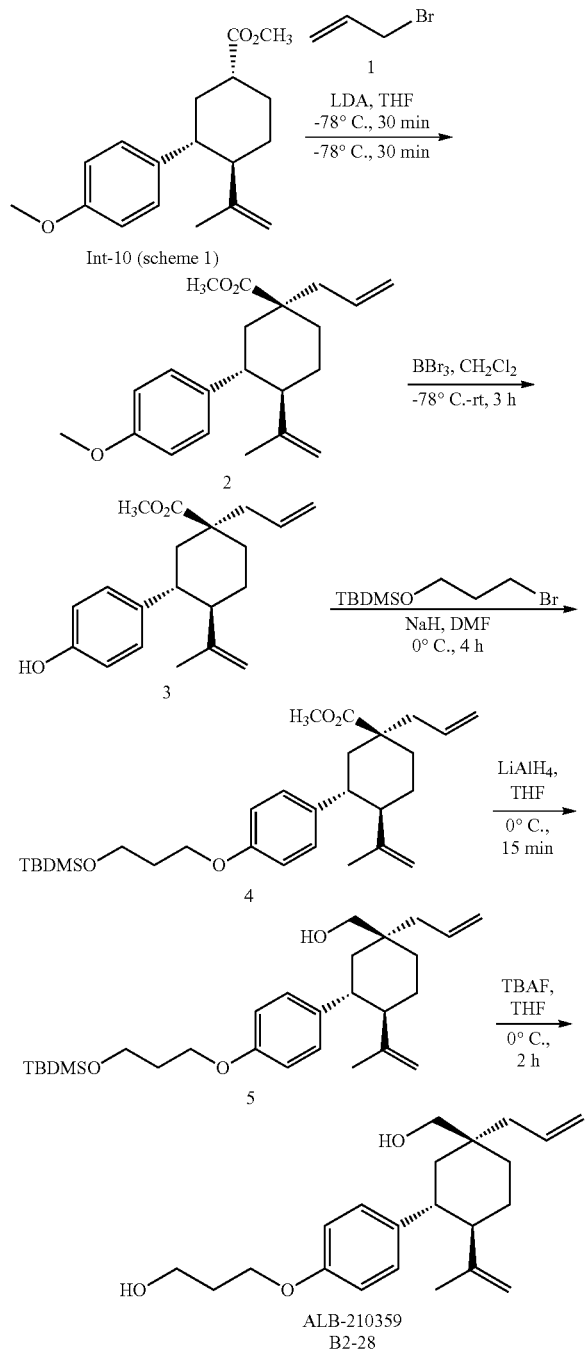

Production of Chemical Compound 2

At −78° C., chemical compound Int-10 (chemical compound 10 in scheme 1) (0.20 g, 0.69 mmol) was dropped to a solution of lithium diisopropylamide (1.04 mL, 2.0 M in THF, 2.08 mmol) dissolved in THF (5.0 mL). The solution was stirred at −78° C. for 30 minutes. Chemical compound 1 (0.09 mL, 1.04 mmol) was added to the reaction mixture at −78° C. The reaction mixture was stirred at −78° C. for 30 minutes and quenched with saturated NH$_4$Cl solution (10 mL). The obtained mixture was extracted with EtOAc (20 mL×3). The organic layer was mixed, washed with brine (10 mL), dried over MgSO$_4$ and concentrated under reduced pressure. The residue was purified by combiflash column chromatography using 0-20% EtOAc in hexane to obtain chemical compound 2 (0.18 g, 79%) as a pale yellow liquid. $^1$H NMR (400 MHz, CDCl$_3$) δ 7.06 (d, J=8.8 Hz, 2H), 6.79 (d, J=8.4 Hz, 2H), 5.71-5.63 (m, 1H), 5.02-4.96 (m, 2H), 4.53 (m, 2H), 3.77 (s, 3H), 3.74 (s, 3H), 2.62-2.57 (m, 1H), 2.32-2.19 (m, 4H), 1.73-1.69 (m, 1H), 1.53-1.50 (m 1H), 1.46 (s, 3H), 1.33-1.25 (m, 2H).

Production of Chemical Compound 3

At −78° C., BBr$_3$ (0.82 mL, 0.82 mmol) dissolved in CH$_2$Cl$_2$ was added to a solution of chemical compound 2 (0.09 g, 0.27 mmol) dissolved in CH$_2$Cl$_2$ (5.0 mL). The reaction mixture was heated to room temperature, stirred for 3 hours, and quenched by the addition of HCl (1 N, 2.0 mL). The obtained mixture was extracted with EtOAc (30 mL×3), dried over MgSO$_4$ and concentrated under reduced pressure to obtain the residue. It was purified by combiflash column chromatography with 0-30% EtOAc in hexane to obtain chemical compound 3 (0.03 g, 35%) as a colorless oil. $^1$H NMR (400 MHz, CDCl$_3$) δ 7.00 (d, J=8.4 Hz, 2H), 6.72 (d, J=8.4 Hz, 2H), 5.71-5.65 (m, 1H), 5.02-4.97 (m, 2H), 4.52 (m, 2H), 3.74 (s, 3H), 2.62-2.55 (m, 1H), 2.32-2.19 (m, 5H), 1.72-1.68 (m, 1H), 1.45 (s, 4H), 1.33-1.23 (m, 4H).

Production of Chemical Compound 4

At 0° C., NaH (0.005 g, 0.13 mmol) was added to an ice-cold solution of chemical compound 3 (0.02 g, 0.06 mmol) dissolved in DMF (1.0 mL). After 30 minutes, (3-bromopropoxy)(tert-butyl)dimethylsilane (0.032 g, 0.13 mmol) was added to the reaction mixture. The reaction mixture was stirred at 0° C. for 4 hours and diluted with H$_2$O. The obtained mixture was extracted with EtOAc (10 mL×3). The organic layer was mixed, washed with brine (10 mL), dried with Na$_2$SO$_4$ and concentrated under reduced pressure. The residue was purified by combiflash column chromatography using 0-10% EtOAc in hexane to obtain chemical compound 4 (0.03 g, 97%) as a colorless oil. ESI MS m/z 387 C$_{29}$H$_{46}$O$_4$Si+H]$^+$.

Production of Chemical Compound 5

At 0° C., LiAlH$_4$ (0.18 mL, 1.0 M in THF, 0.18 mmol) was added to an ice-cold solution of chemical compound 4 (0.03 g, 0.06 mmol) dissolved in THF (1.0 mL). The mixture was stirred at 0° C. for 15 minutes and diluted with H$_2$O and Na$_2$SO$_4$·10H$_2$O. The obtained mixture was extracted with EtOAc (10 mL×3). The organic layer was mixed, washed with brine (5.0 mL), dried with Na$_2$SO$_4$ and concentrated under reduced pressure. The residue was purified by combiflash column chromatography using 0-30% EtOAc in hexane to obtain chemical compound 5 (0.015 g, 68%) as a colorless oil. $^1$H NMR (400 MHz, CDCl$_3$) δ 6.95 (d, J=8.8 Hz, 2H), 6.71 (d, J=8.8 Hz, 2H), 5.85-5.79 (m, 1H), 5.02-4.97 (m, 2H), 4.46 (m, 2H), 4.06-3.94 (m, 2H), 3.72-3.49 (m, 6H), 2.58-2.49 (m, 1H), 2.18-2.11 (m, 1H), 1.89-1.68 (m, 6H), 1.48 (s, 4H), 0.81 (m, 9H), 0.00 (m, 6H).

Production of Chemical Compound ALB-210359(B2-28)

At 0° C., TBAF (0.12 mL, 1.0 M in THF, 0.12 mmol) was added to an ice-cold solution of chemical compound 5

(0.015 g, 0.041 mmol) dissolved in THF (1.0 mL). The reaction mixture was stirred at 0° C. for 2 hours and diluted with $H_2O$. The obtained mixture was extracted with EtOAc (5.0 mL×3). The organic layer was mixed, washed with brine (5.0 mL), dried with $Na_2SO_4$ and concentrated under reduced pressure. The residue was purified by combiflash column chromatography using 0-60% EtOAc in hexane to obtain chemical compound ALB-210359(B2-28) (0.0065 g, 45%) as a colorless viscous material. $^1$H NMR (400 MHz, $CDCl_3$) δ 7.03 (d, J=8.4 Hz, 2H), 6.79 (d, J=8.8 Hz, 2H), 5.93-5.83 (m, 1H), 5.09-5.04 (m, 2H), 4.53 (m, 2H), 4.08 (t, J=6.0 Hz, 2H), 3.84 (t, J=6.0 Hz, 2H), 3.70 (m, 2H), 2.66-2.59 (m, 1H), 2.33-2.19 (m, 1H), 2.04-2.00 (m, 4H), 1.78-1.58 (m, 6H), 1.49 (s, 4H). ESI MS m/z 345 $C_{22}H_{32}O_3$+H]$^+$.

Synthesis Example 17

Synthesis of Chemical Compounds B2-27 and B2-21

A method for the production of chemical compounds B2-27 (also called ALB-209872) and B2-21 (also called ALB-208788) is as follows (also called scheme 17).

[Chemical 63]

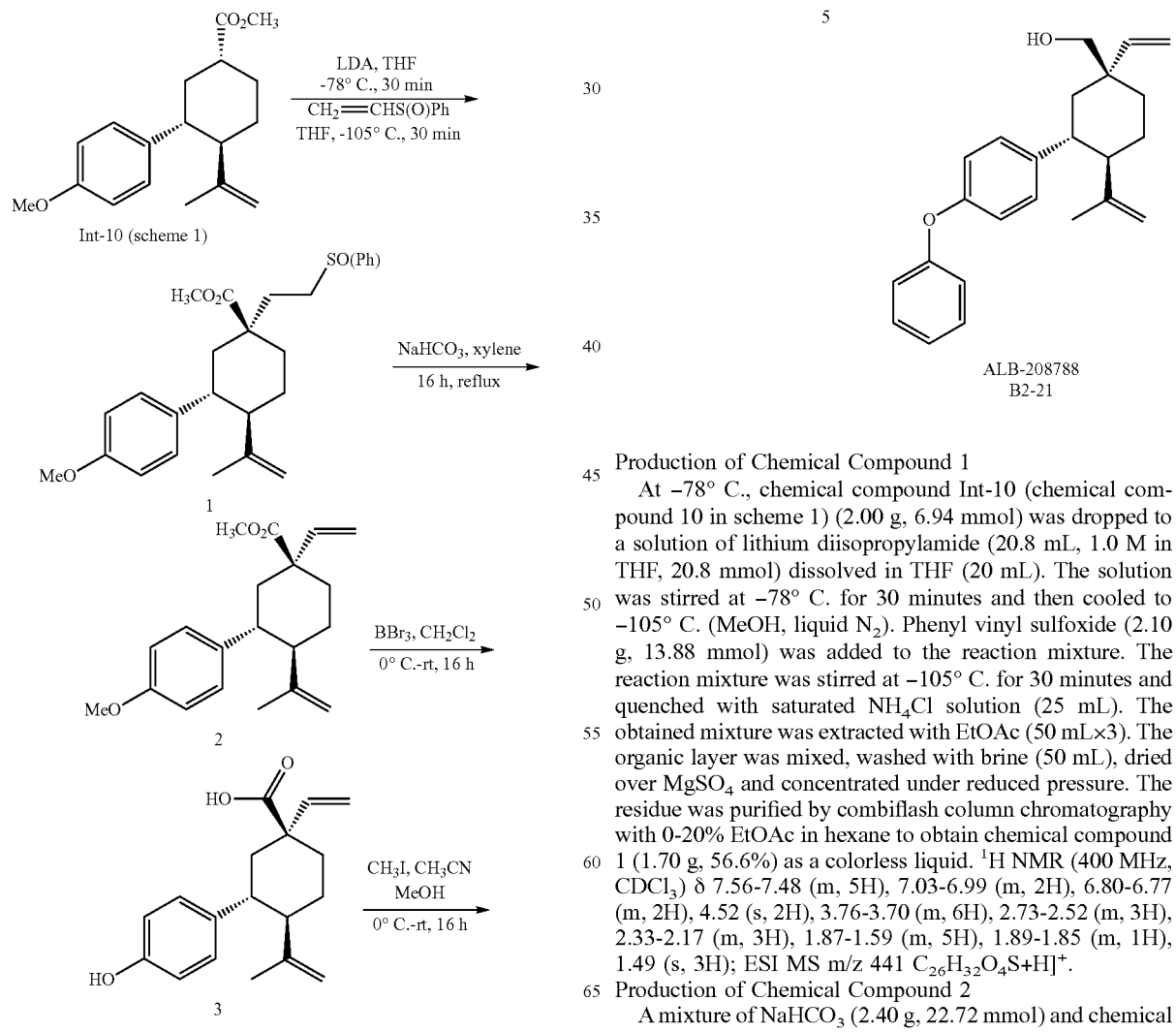

Production of Chemical Compound 1

At −78° C., chemical compound Int-10 (chemical compound 10 in scheme 1) (2.00 g, 6.94 mmol) was dropped to a solution of lithium diisopropylamide (20.8 mL, 1.0 M in THF, 20.8 mmol) dissolved in THF (20 mL). The solution was stirred at −78° C. for 30 minutes and then cooled to −105° C. (MeOH, liquid $N_2$). Phenyl vinyl sulfoxide (2.10 g, 13.88 mmol) was added to the reaction mixture. The reaction mixture was stirred at −105° C. for 30 minutes and quenched with saturated $NH_4Cl$ solution (25 mL). The obtained mixture was extracted with EtOAc (50 mL×3). The organic layer was mixed, washed with brine (50 mL), dried over $MgSO_4$ and concentrated under reduced pressure. The residue was purified by combiflash column chromatography with 0-20% EtOAc in hexane to obtain chemical compound 1 (1.70 g, 56.6%) as a colorless liquid. $^1$H NMR (400 MHz, $CDCl_3$) δ 7.56-7.48 (m, 5H), 7.03-6.99 (m, 2H), 6.80-6.77 (m, 2H), 4.52 (s, 2H), 3.76-3.70 (m, 6H), 2.73-2.52 (m, 3H), 2.33-2.17 (m, 3H), 1.87-1.59 (m, 5H), 1.89-1.85 (m, 1H), 1.49 (s, 3H); ESI MS m/z 441 $C_{26}H_{32}O_4S$+H]$^+$.

Production of Chemical Compound 2

A mixture of $NaHCO_3$ (2.40 g, 22.72 mmol) and chemical compound 11 (1.00 g, 2.27 mmol) dissolved in xylene (20 mL) was stirred under reflux for 16 hours and diluted with H$_2$O. The obtained mixture was extracted with EtOAc (30 mL×3). The organic layer was mixed, washed with brine (25 mL), dried over MgSO$_4$ and concentrated under reduced pressure to obtain the residual oil. It was purified by combiflash column chromatography using 0-20% EtOAc in hexane to obtain chemical compound 2 (0.30 g, 42%) as a pale yellow liquid. $^1$H NMR (400 MHz, CDCl$_3$) δ 7.07 (d, J=8.8 Hz, 2H), 6.80 (d, J=8.4 Hz, 2H), 5.85-5.78 (m, 1H), 5.09-5.03 (m, 2H), 4.54 (m, 2H), 3.77 (s, 6H) 2.66-2.60 (m, 1H), 2.58-2.28 (m, 4H), 1.78-1.74 (m, 1H), 1.47 (s, 4H).

Production of Chemical Compound 3

At 0° C., BBr$_3$ (0.95 mL, 0.95 mmol) dissolved in CH$_2$Cl$_2$ was added to a solution of chemical compound 2 (0.15 g, 0.48 mmol) dissolved in CH$_2$Cl$_2$ (5.0 mL). The reaction mixture was heated to room temperature, stirred for 16 hours and quenched by the addition of HCl solution (1 N, 5.0 mL). The obtained mixture was extracted with EtOAc (10 mL×3), dried over Na$_2$SO$_4$ and concentrated under reduced pressure to obtain the residue. It was purified by combiflash column chromatography using 0-60% EtOAc in hexane to obtain chemical compound 3 (0.07 g, 51%) as a colorless liquid. $^1$H NMR (400 MHz, CDCl$_3$) δ 7.03 (d, J=8.4 Hz, 2H), 6.73 (d, J=8.4 Hz, 2H), 5.91-5.84 (m, 1H), 5.20-5.11 (m, 2H), 4.56 (m, 2H), 2.72-2.65 (m, 1H), 2.46-2.40 (m, 3H), 2.29-2.23 (m, 1H), 1.81-1.56 (m, 4H), 1.49 (s, 3H).

Production of Chemical Compound ALB-209872 (B2-27)

At 0° C., K$_2$CO$_3$ (0.03 g, 0.21 mmol) and MeI (0.02 g, 0.16 mmol) were dropped to an ice-cold solution of chemical compound 13 (0.03 g, 0.10 mmol) dissolved in CH$_3$CN (1.0 mL). The reaction mixture was stirred at room temperature for 16 hours. The obtained mixture was extracted with EtOAc (5.0 mL×3). The organic layer was mixed, washed with brine (5.0 mL), dried over Na$_2$SO$_4$ and concentrated under reduced pressure. The residue was purified by combiflash column chromatography using 0-30% EtOAc in hexane to obtain chemical compound ALB-209872(B2-27) (0.012 g, 50%) as a pale yellow oil. $^1$H NMR (400 MHz, CDCl$_3$) δ 7.04 (d, J=8.4 Hz, 2H), 6.75 (d, J=8.4 Hz, 2H), 5.87-5.80 (m, 1H), 5.12-5.06 (m, 2H), 4.59-4.50 (m, 2H), 3.79 (s, 2H), 2.65-2.42 (m, 3H), 2.28-2.22 (m, 1H), 1.80-1.76 (m, 1H), 1.49 (s, 4H), 1.43-1.38 (m, 2H); ESI MS m/z 301 C$_{19}$H$_{24}$O$_3$+H]$^+$.

Production of Chemical Compound 5

At room temperature, chemical compound 4 (0.24 g, 0.20 mmol), Cu(OAc)$_2$ (0.036 g, 0.20 mmol) and pyridine (0.015 g, 0.20 mmol) were dropped to a mixture of chemical compound ALB-209872(B2-27) (0.03 g, 0.10 mmol) dissolved in CH$_2$Cl$_2$ (1.0 mL). The reaction mixture was stirred for 48 hours. The obtained mixture was extracted with EtOAc (5.0 mL×3). The organic layer was mixed, washed with brine (5.0 mL), dried over Na$_2$SO$_4$ and concentrated under reduced pressure. The residue was purified by combiflash column chromatography using 0-20% EtOAc in hexane to obtain chemical compound 5 (0.02 g, 54%) as a colorless oil. $^1$H NMR (400 MHz, CDCl$_3$) δ 7.31 (t, J=7.6 Hz, 2H), 7.07 (t, J=7.6 Hz, 3H), 6.98 (d, J=7.6 Hz, 2H), 6.90 (d, J=8.4 Hz, 2H), 5.86-5.79 (m, 1H), 5.11-5.05 (m, 2H), 4.55 (s, 2H), 3.77 (s, 3H), 2.68-2.61 (m, 1H), 2.47-2.44 (m, 2H), 2.28-2.23 (m, 1H), 1.79-1.75 (m, 1H), 1.48 (s, 4H), 1.43-1.40 (m, 1H); ESI MS m/z 315 C$_{20}$H$_{26}$O$_3$+H]$^+$. ESI MS m/z 376 [M+H]$^+$.

Production of Chemical Compound ALB-208788 (B2-21)

At 0° C., LiAlH$_4$ (0.08 mL, 2.0 M in THF, 0.16 mmol) was added to an ice-cold solution of chemical compound 5 (0.02 g, 0.05 mmol) dissolved in THF (1.0 mL). The reaction mixture was stirred at 0° C. for 15 minutes and diluted with H$_2$O and Na$_2$SO$_4$·10H$_2$O. The obtained mixture was extracted with EtOAc (5.0 mL×3). The organic layer was mixed, washed with brine (5.0 mL), dried with Na$_2$SO$_4$ and concentrated under reduced pressure. The residue was purified by combiflash column chromatography using 0-30% EtOAc in hexane to obtain chemical compound ALB-208788 (B2-21) (0.0095 g, 55%) as a colorless viscous material. $^1$H NMR (400 MHz, CDCl$_3$) δ 7.33-7.29 (m, 2H), 7.11-7.05 (m, 3H), 6.99, 6.96 (dd, J=1.2, 8.8 Hz, 2H), 6.89 (d, J=8.8 Hz, 2H), 5.78-5.71 (m, 1H), 5.17-5.06 (m, 2H), 4.56 (m, 2H), 3.70 (d, J=6.4 Hz, 2H), 2.76-2.69 (m, 1H), 2.28-2.21 (m, 1H), 1.92-1.88 (m, 2H), 1.70-1.64 (m, 2H), 1.49 (s, 4H), 1.48-1.43 (m, 2H); ESI MS m/z 349 C$_{24}$H$_{28}$O$_2$+H]$^+$.

Synthesis Example 18

Synthesis of Chemical Compound B2-19

A method for the production of chemical compound B2-19 (also called ALB-209870) is as follows (also called scheme 19).

[Chemical 64]

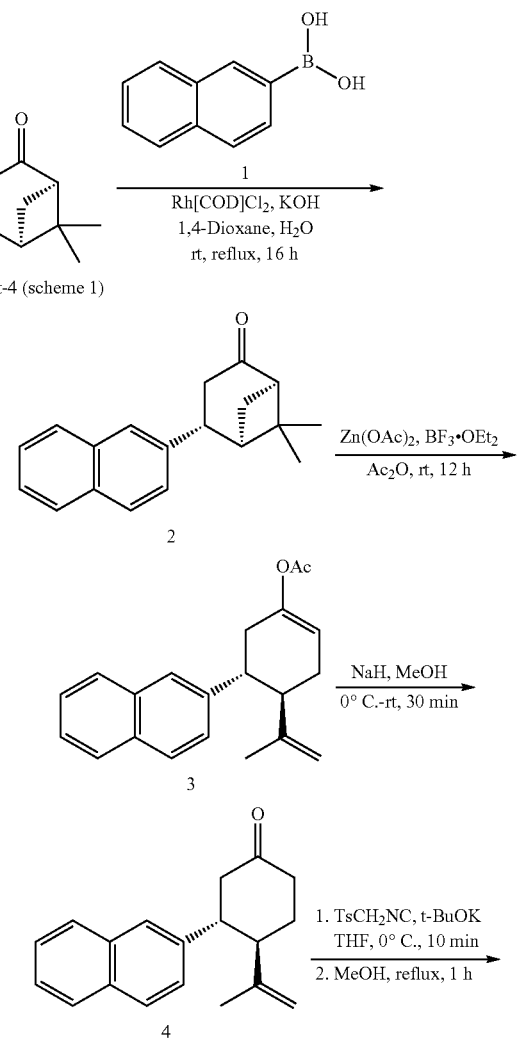

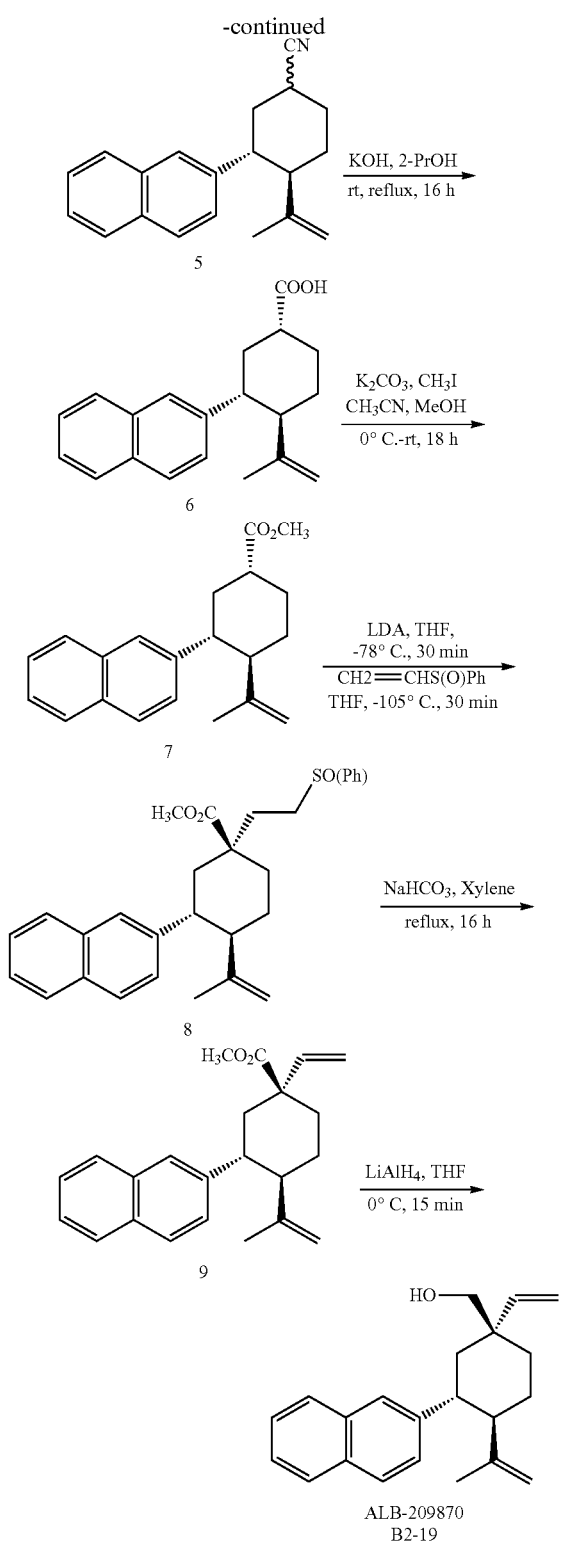

Production of Chemical Compound 2

At room temperature, a solution of chemical compound Int-4 (chemical compound 4 in scheme 1) (5.00 g, 36.76 mmol) dissolved in 1,4-dioxane:water (40 mL: 10 mL) was added to a mixture of chemical compound 1 (7.58 g, 44.11 mmol) and KOH (4.10 g, 73.52 mmol). The reaction mixture was degassed with argon for 15 minutes and [Rh(COD)Cl]$_2$ (0.54 g, 1.10 mmol) was added thereto. The reaction mixture was stirred under reflux for 16 hours. The reaction mixture was quenched with saturated NaHCO$_3$ (30 mL) and extracted with EtOAc (20 mL×2). The organic layer was mixed, washed with brine (20 mL), dried over anhydrous Na$_2$SO$_4$, filtered, and concentrated under reduced pressure. The crude product was purified by combiflash column chromatography using 0-20% EtOAc in hexane to obtain chemical compound 2 (2.00 g, quantitative) as a brown semisolid. $^1$H NMR (400 MHz, CDCl$_3$) δ 7.80 (t, J=8.0 Hz, 2H), 7.65 (s, 1H), 7.49-7.36 (m, 3H), 3.58 (t, J=8.0 Hz, 1H), 2.91-2.77 (m, 2H), 2.68-2.52 (m, 3H), 1.43 (s, 3H), 1.03 (m, 3H).

Production of Chemical Compound 3

Zn(OAc)$_2$ (1.10 g, 6.06 mmol) and BF$_3$·OEt$_2$ (0.54 mL, 3.03 mmol) were added to a solution of chemical compound 2 (1.60 g, 6.06 mmol) dissolved in Ac$_2$O (10 mL), and the solution was stirred at room temperature for 12 hours. The reaction mixture was diluted with H$_2$O (20 mL). The obtained mixture was extracted with EtOAc (20 mL×3). The organic layer was mixed, washed with saturated NaHCO$_3$ (250 mL) and brine (50 mL), dried over Na$_2$SO$_4$ and concentrated under reduced pressure. The product was purified by combiflash column chromatography using 0-10% EtOAc in hexane to obtain chemical compound 3 (1.80 g, 78%) as an off-white solid. $^1$H NMR (400 MHz, CDCl$_3$) δ 7.79-7.74 (m, 3H), 7.61 (s, 1H), 7.45-7.38 (m, 2H), 7.35-7.32 (m, 1H), 5.50-5.48 (m, 1H), 4.71-4.54 (m, 2H), 3.19-3.12 (m, 1H), 2.88-2.81 (m, 1H), 2.56-2.49 (m, 2H), 2.40-2.25 (m, 2H), 2.10 (s, 3H), 1.51 (s, 3H).

Production of Chemical Compound 4

NaH (0.078 g, 60% in mineral oil, 1.96 mmol) was added to a solution of chemical compound 3 (1.20 g, 3.92 mmol) dissolved in MeOH (10 mL) (0° C.), and the solution was stirred at room temperature for 30 minutes. The reaction mixture was diluted with saturated NH$_4$Cl (10 mL). The obtained mixture was extracted with EtOAc (50 mL×3). The organic layer was mixed, washed with brine (50 mL), dried over Na$_2$SO$_4$ and concentrated to obtain the residual oil. It was purified by combiflash column chromatography using 0-20% EtOAc in hexane to obtain chemical compound 4 (1.20 g, 77%) as an off-white solid. $^1$H NMR (400 MHz, CDCl$_3$) δ 7.80-7.76 (m, 3H), 7.57 (s, 1H), 7.46-7.43 (m, 2H), 7.35-7.32 (m, 1H), 4.69-4.56 (m, 2H), 3.17-3.13 (m, 1H), 2.93-2.87 (m, 1H), 2.69-2.55 (m, 4H), 2.17-2.12 (m, 4H), 1.98-1.91 (m, 1H), 1.53 (s, 3H).

Production of Chemical Compound 5

Chemical compound 4 (0.50 g, 1.89 mmol) dissolved in THF (5.0 mL) was added to an ice-cold solution of t-BuOK (0.85 g, 7.57 mmol) and p-toluenesulfonylmethylisocyanide (0.74 g, 3.79 mmol) dissolved in THF (5.0 mL). After stirring the solution for 10 minutes at 0° C., MeOH (10 mL) was added thereto. The obtained mixture was stirred under reflux for 1 hours and concentrated under reduced pressure. The crude product was purified by combiflash column chromatography using 0-20% EtOAc in hexane to obtain chemical compound 5 (0.25 g, 48%) as a colorless liquid. $^1$H NMR (400 MHz, CDCl$_3$) δ 7.80-7.75 (m, 3H), 7.60 (s, 1H), 7.45-7.42 (m, 2H), 7.31-7.28 (m, 1H), 4.61 (m, J=11.2 Hz, 1H), 4.51 (m, 1H), 3.14-3.10 (m, 1H), 2.75-2.63 (m, 2H), 2.51-2.14 (m, 2H), 1.96-1.74 (m, 4H), 1.49 (s, 3H).

Production of Chemical Compound 6

At room temperature, KOH (0.51 g, 9.09 mmol) was added to a solution of chemical compound 5 (0.25 g, 0.91 mmol) dissolved in 2-propanol (5.0 mL). The reaction mixture was stirred under reflux for 16 hours and quenched by the addition of HCl solution (2 N). The obtained mixture was extracted with EtOAc (10 mL×3). The organic layer was mixed, washed with brine (20 mL), dried over Na₂SO₄ and concentrated under reduced pressure to obtain chemical compound 6 (0.20 g, 75%) as an off-white solid. ¹H NMR (400 MHz, CDCl₃) δ 7.78-7.73 (m, 3H), 7.56 (s, 1H), 7.44-7.37 (m, 2H), 7.32, 7.29 (dd, J=1.6 Hz, 8.4 Hz, 1H), 4.58-4.49 (m, 2H), 2.76-2.60 (m, 1H), 2.59-2.40 (m, 2H), 2.23-2.10 (m, 2H), 1.96-1.92 (m, 1H), 1.78-1.66 (m, 2H), 1.51 (s, 3H).

Production of Chemical Compound 7

At 0° C., K₂CO₃ (0.19 g, 1.36 mmol) and CH₃I (0.15 g, 1.02 mmol) were dropped to an ice-cold solution of chemical compound 6 (0.20 g, 0.68 mmol) dissolved in CH₃CN: MeOH (3.0 mL: 1.0 mL). The reaction mixture was stirred at room temperature for 18 hours and then concentrated under reduced pressure. The residue was purified by combiflash column chromatography using 0-20% EtOAc in hexane to obtain chemical compound 7 (0.15 g, 71%) as an off-white solid. ¹H NMR (400 MHz, CDCl₃) δ 7.78-7.73 (m, 3H), 7.56 (s, 1H), 7.44-7.37 (m, 2H), 7.32, 7.29 (dd, J=1.6 Hz, 8.4 Hz, 1H), 4.58-4.48 (m, 2H), 3.67 (s, 3H), 2.78-2.72 (m, 1H), 2.57-2.42 (m, 2H), 1.95-1.91 (m, 2H), 1.76-1.64 (m, 2H), 1.51 (s, 3H).

Production of Chemical Compound 8

At −78° C., chemical compound 7 (0.15 g, 0.49 mmol) was dropped to a solution of lithium diisopropylamide (0.73 mL, 2.0 M in THF, 1.46 mmol) dissolved in THF (1.0 mL). The solution was stirred at −78° C. for 30 minutes, then cooled to −105° C. (MeOH, liquid N₂), and phenyl vinyl sulfoxide (0.13 mL, 0.97 mmol) was added to the reaction mixture. The reaction mixture was stirred at −105° C. for 30 minutes and quenched with saturated NH₄Cl solution (5.0 mL). The obtained mixture was extracted with EtOAc (10 mL×3). The organic layer was mixed, washed with brine (10 mL), dried over Na₂SO₄ and concentrated under reduced pressure. The residue was purified by combiflash column chromatography using 0-20% EtOAc in hexane to obtain chemical compound 8 (0.07 g, 31%) as a pale yellow liquid.

Production of Chemical Compound 9

A mixture of NaHCO₃ (0.16 g, 1.52 mmol) and chemical compound 8 (0.07 g, 0.15 mmol) dissolved in xylene (2.0 mL) was stirred under reflux for 16 hours and diluted with H₂O. The obtained mixture was extracted with EtOAc (10 mL×3). The organic layer was mixed, washed with brine (5.0 mL), dried with Na₂SO₄ and concentrated under reduced pressure to obtain the residual oil. It was purified by combiflash column chromatography using 0-20% EtOAc in hexane to obtain chemical compound 9 (0.015 g, 30%) as a colorless liquid. ¹H NMR (400 MHz, CDCl₃) δ 7.79-7.74 (m, 3H), 7.58 (s, 1H), 7.43-7.31 (m, 3H), 5.87-5.80 (m, 1H), 5.10-5.05 (m, 2H), 4.58-4.48 (m, 2H), 3.81 (s, 3H), 2.88-2.82 (m, 1H), 2.52-2.44 (m, 3H), 1.83-1.80 (m, 1H), 1.49 (s, 4H).

Production of Chemical Compound ALB-209870 (B2-19)

At 0° C., LiAlH₄ (0.13 mL, 2.0 M in THF, 0.13 mmol) was added to an ice-cold solution of chemical compound 9 (0.015 g, 0.04 mmol) dissolved in THF (1.0 mL). The reaction mixture was stirred at 0° C. for 15 minutes and diluted with H₂O and Na₂SO₄·10H₂O. The obtained mixture was extracted with EtOAc (5.0 mL×3). The organic layer was mixed, washed with brine (5.0 mL), dried with Na₂SO₄ and concentrated under reduced pressure. The residue was purified by combiflash column chromatography using 0-30% EtOAc in hexane to obtain chemical compound ALB-209870(B2-19) (0.005 g, 30%) as a colorless viscous material. ¹H NMR (400 MHz, CDCl₃) δ 7.71-7.66 (m, 3H), 7.50 (s, 1H), 7.37-7.32 (m, 2H), 7.26, 7.24 (dd, J=1.6 Hz, 8.8 Hz, 1H), 5.72-5.65 (m, 2H), 5.09-4.98 (m, 2H), 4.47 (m, 2H), 3.67 (d, J=4.8 Hz, 2H), 2.88-2.82 (m, 1H), 2.41-2.34 (m, 1H), 1.90-1.83 (m, 2H), 1.68-1.62 (m, 2H), 1.46 (s, 3H), 1.30-1.29 (m, 2H); ESI MS m/z 307 C₂₂H₂₆O+H]⁺.

Synthesis Example 19

Synthesis of Chemical Compound B2-18

A method for the production of chemical compound B2-18 (also called ALB-208789) is as follows (also called scheme 20).

[Chemical 65]

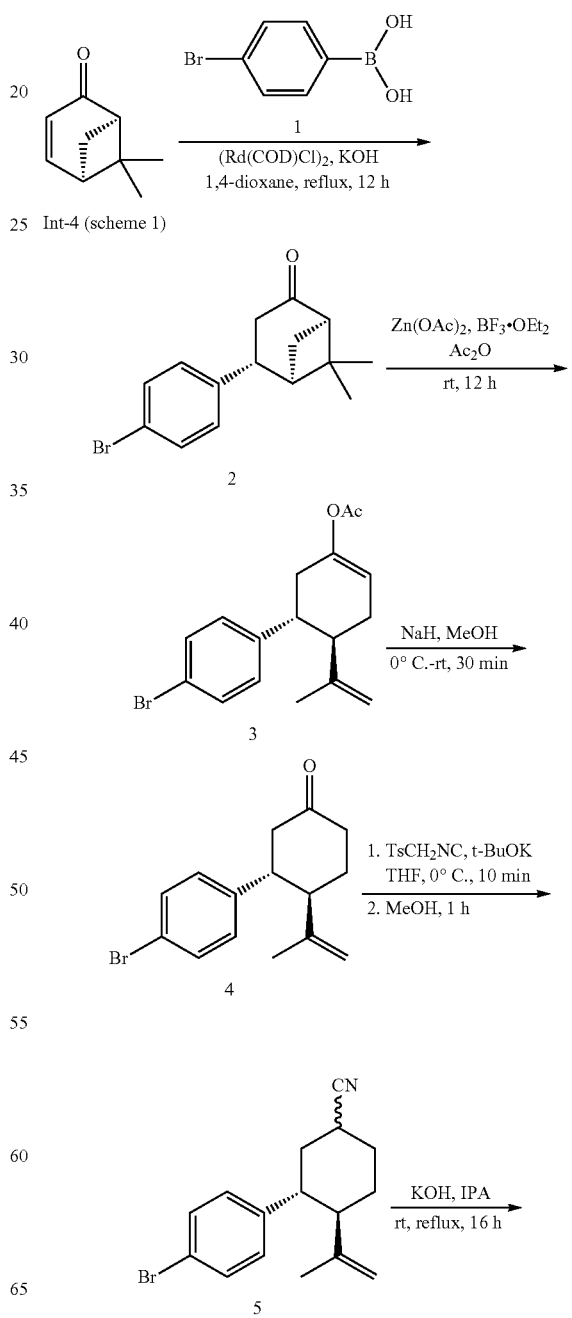

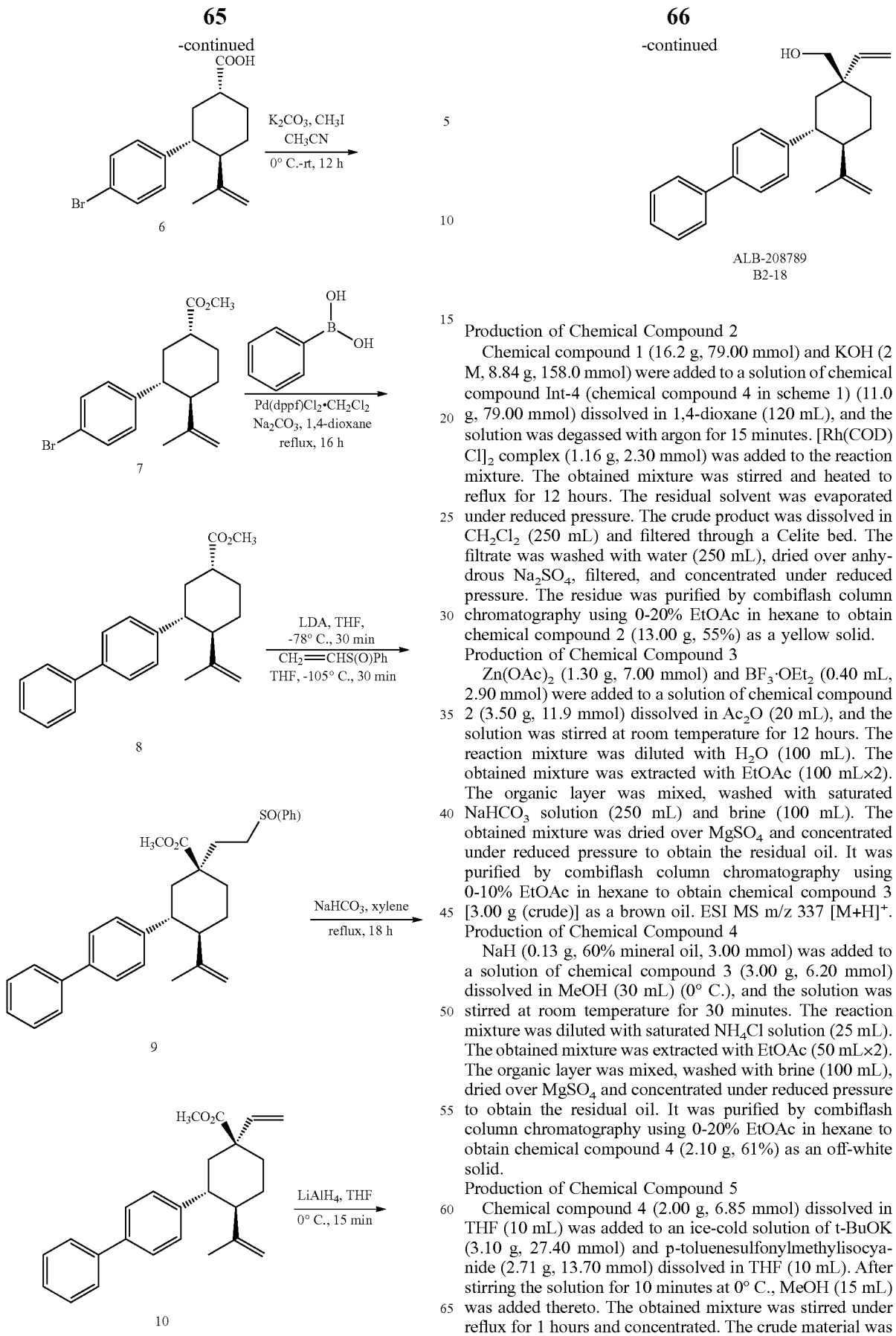

Production of Chemical Compound 2

Chemical compound 1 (16.2 g, 79.00 mmol) and KOH (2 M, 8.84 g, 158.0 mmol) were added to a solution of chemical compound Int-4 (chemical compound 4 in scheme 1) (11.0 g, 79.00 mmol) dissolved in 1,4-dioxane (120 mL), and the solution was degassed with argon for 15 minutes. [Rh(COD)Cl]$_2$ complex (1.16 g, 2.30 mmol) was added to the reaction mixture. The obtained mixture was stirred and heated to reflux for 12 hours. The residual solvent was evaporated under reduced pressure. The crude product was dissolved in CH$_2$Cl$_2$ (250 mL) and filtered through a Celite bed. The filtrate was washed with water (250 mL), dried over anhydrous Na$_2$SO$_4$, filtered, and concentrated under reduced pressure. The residue was purified by combiflash column chromatography using 0-20% EtOAc in hexane to obtain chemical compound 2 (13.00 g, 55%) as a yellow solid.

Production of Chemical Compound 3

Zn(OAc)$_2$ (1.30 g, 7.00 mmol) and BF$_3$·OEt$_2$ (0.40 mL, 2.90 mmol) were added to a solution of chemical compound 2 (3.50 g, 11.9 mmol) dissolved in Ac$_2$O (20 mL), and the solution was stirred at room temperature for 12 hours. The reaction mixture was diluted with H$_2$O (100 mL). The obtained mixture was extracted with EtOAc (100 mL×2). The organic layer was mixed, washed with saturated NaHCO$_3$ solution (250 mL) and brine (100 mL). The obtained mixture was dried over MgSO$_4$ and concentrated under reduced pressure to obtain the residual oil. It was purified by combiflash column chromatography using 0-10% EtOAc in hexane to obtain chemical compound 3 [3.00 g (crude)] as a brown oil. ESI MS m/z 337 [M+H]$^+$.

Production of Chemical Compound 4

NaH (0.13 g, 60% mineral oil, 3.00 mmol) was added to a solution of chemical compound 3 (3.00 g, 6.20 mmol) dissolved in MeOH (30 mL) (0° C.), and the solution was stirred at room temperature for 30 minutes. The reaction mixture was diluted with saturated NH$_4$Cl solution (25 mL). The obtained mixture was extracted with EtOAc (50 mL×2). The organic layer was mixed, washed with brine (100 mL), dried over MgSO$_4$ and concentrated under reduced pressure to obtain the residual oil. It was purified by combiflash column chromatography using 0-20% EtOAc in hexane to obtain chemical compound 4 (2.10 g, 61%) as an off-white solid.

Production of Chemical Compound 5

Chemical compound 4 (2.00 g, 6.85 mmol) dissolved in THF (10 mL) was added to an ice-cold solution of t-BuOK (3.10 g, 27.40 mmol) and p-toluenesulfonylmethylisocyanide (2.71 g, 13.70 mmol) dissolved in THF (10 mL). After stirring the solution for 10 minutes at 0° C., MeOH (15 mL) was added thereto. The obtained mixture was stirred under reflux for 1 hours and concentrated. The crude material was purified by combiflash column chromatography using 0-10% EtOAc in hexane to obtain chemical compound 5 (1.20 g, 60%) as a pale yellow oil. $^1$H NMR (400 MHz, CDCl$_3$) δ 7.05 (d, J=8.4 Hz, 2H), 6.82 (d, J=8.8 Hz, 2H), 4.64 (d, J=10.4 Hz, 2H), 3.78 (s, 3H), 2.96-2.89 (m, 1H), 2.74-2.68 (m, 1H), 2.53-2.49 (m, 4H), 2.11-2.07 (m, 1H), 1.91-1.55 (m, 1H), 1.51 (s, 3H).

Production of Chemical Compound 6

At room temperature, KOH (0.89 g, 15.70 mmol) was added to a solution of chemical compound 5 (0.48 g, 1.57 mmol) dissolved in 2-propanol (10 mL). The reaction mixture was stirred under reflux for 16 hours and quenched by the addition of HCl solution (2 N, 10 mL). The obtained mixture was extracted with EtOAc (10 mL×3). The organic layer was mixed, washed with brine (25 mL), dried over MgSO$_4$ and concentrated under reduced pressure to obtain chemical compound 6 [0.50 g (crude)] as an off-white solid. ESI MS m/z 323 [M+H]$^+$.

Production of Chemical Compound 7

At 0° C., K$_2$CO$_3$ (0.51 g, 3.72 mmol) and CH$_3$I (0.23 mL, 3.72 mmol) were dropped to an ice-cold solution of chemical compound 6 (0.40 g, 1.24 mmol) dissolved in CH$_3$CN (5.0 mL). The reaction mixture was heated to room temperature and stirred for 12 hours. The obtained mixture was extracted with EtOAc (10 mL×2). The organic layer was mixed, washed with brine (10 mL), dried over MgSO$_4$ and concentrated under reduced pressure. The residue was purified by column chromatography using 0-20% EtOAc in hexane to obtain chemical compound 7 (0.30 g, 72%) as a colorless oil. $^1$H NMR (400 MHz, CDCl$_3$) δ 7.04 (d, J=8.8 Hz, 2H), 6.79 (d, J=8.4 Hz, 2H), 4.55 (m, 2H), 3.76 (s, 3H), 3.65 (s, 3H), 2.54-2.45 (m, 2H), 2.30-2.24 (m, 1H), 2.10-2.06 (m, 2H), 1.89-1.85 (m, 1H), 1.62-1.58 (m, 3H), 1.49 (s, 3H).

Production of Chemical Compound 8

Phenylboronic acid (0.06 g, 0.47 mmol) and Na$_2$CO$_3$ (0.063 g, 2 M, 0.59 mmol) were added to a solution of chemical compound 7 (0.08 g, 0.24 mmol) dissolved in 1,4-dioxane (10 mL), and the solution was degassed with argon for 15 minutes. Pd(dppf)Cl$_2$·CH$_2$Cl$_2$ complex solution (0.019 g, 0.02 mmol) was added to the reaction mixture. The obtained mixture was stirred and heated to reflux for 16 hours. The residual solvent was evaporated. The crude product was dissolved in CH$_2$Cl$_2$ (10 mL) and filtered through a Celite bed. The filtrate was washed with water (10 mL), dried over anhydrous Na$_2$SO$_4$, filtered, and concentrated under reduced pressure. The residue was purified by column chromatography using 0-10% EtOAc in hexane to obtain chemical compound 8 (0.08 g, 69%) as an off-white solid. ESI MS m/z 352 [M+NH$_4$]$^+$.

Production of Chemical Compound 9

At −78° C., chemical compound 8 (0.10 g, 0.30 mmol) dissolved in THF (3.0 mL) was dropped to a solution of lithium diisopropylamide (0.50 mL, 2.0 M in THF, 0.89 mmol) dissolved in THF (3.0 mL). The solution was stirred at −78° C. for 30 minutes, then cooled to −105° C. (MeOH, liquid N$_2$), and phenyl vinyl sulfoxide (0.091 g, 0.60 mmol) was added to the reaction mixture. The reaction mixture was stirred at −105° C. for 30 minutes and quenched with saturated NH$_4$Cl solution (5.0 mL). The obtained mixture was extracted with EtOAc (10 mL×2). The organic layer was mixed, washed with brine (5.0 mL), dried over MgSO$_4$ and concentrated under reduced pressure. The residue was purified by column chromatography using 0-10% EtOAc in hexane to obtain chemical compound 9 (0.06 g, 41%) as a brown liquid. ESI MS m/z 487 [M+H]$^+$.

Production of Chemical Compound 10

A mixture of NaHCO$_3$ (0.10 g, 1.23 mmol) and chemical compound 9 (0.06 g, 0.12 mmol) dissolved in xylene (3.0 mL) was stirred under reflux for 18 hours and diluted with H$_2$O. The obtained mixture was extracted with EtOAc (10 mL×2). The organic layer was mixed, washed with brine (5.0 mL), dried over MgSO$_4$ and concentrated under reduced pressure to obtain the residual oil. It was purified by column chromatography using 0-20% EtOAc in hexane to obtain chemical compound 10 (0.03 g, 68%) as a colored oil. ESI MS m/z 361 [M+H]$^+$.

Production of Chemical Compound ALB-208789 (B2-18)

At 0° C., LiAlH$_4$ (0.12 mL, 2.0 M in THF, 0.24 mmol) was added to an ice-cold solution of chemical compound 10 (0.03 g, 0.08 mmol) dissolved in THF (3.0 mL). The reaction mixture was stirred at 0° C. for 15 minutes and diluted with H$_2$O and Na$_2$SO$_4$·10H$_2$O. The obtained mixture was extracted with EtOAc (5.0 mL×2). The organic layer was mixed, washed with brine (5.0 mL), dried with Na$_2$SO$_4$ and concentrated under reduced pressure. The residue was purified by column chromatography using 0-30% EtOAc in hexane to obtain chemical compound ALB-208789(B2-18) (0.005 g, 19%) as an off-white solid. $^1$H NMR (400 MHz, CDCl$_3$) δ 7.51 (d, J=7.2 Hz, 1H), 7.42 (d, J=8.0 Hz, 1H), 7.36-7.24 (m, 5H), 7.15 (d, J=8.4 Hz, 1H), 6.97 (d, J=8.0 Hz, 1H), 5.70-5.63 (m, 1H), 5.09-4.97 (m, 2H), 4.52 (d, 2H), 4.48 (s, 1H), 3.66-3.61 (m, 2H), 2.75-2.61 (m, 1H), 2.28-2.13 (m, 2H), 1.85-1.80 (m, 2H), 1.66-1.60 (m, 3H), 1.44 (s, 3H), 1.41-1.25 (m, 3H).

Synthesis Example 20

Synthesis of Chemical Compound B2-23

The method for the production of chemical compound B2-23 (also called ALB-208790) (also called scheme 21) is as follows.

[Chemical 66]

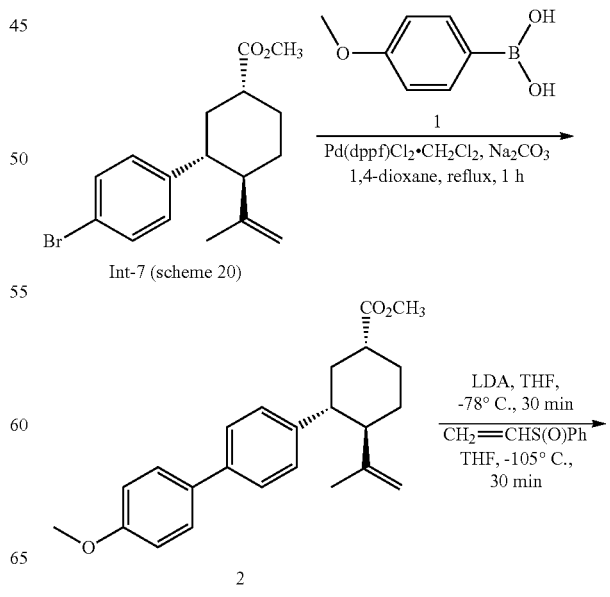

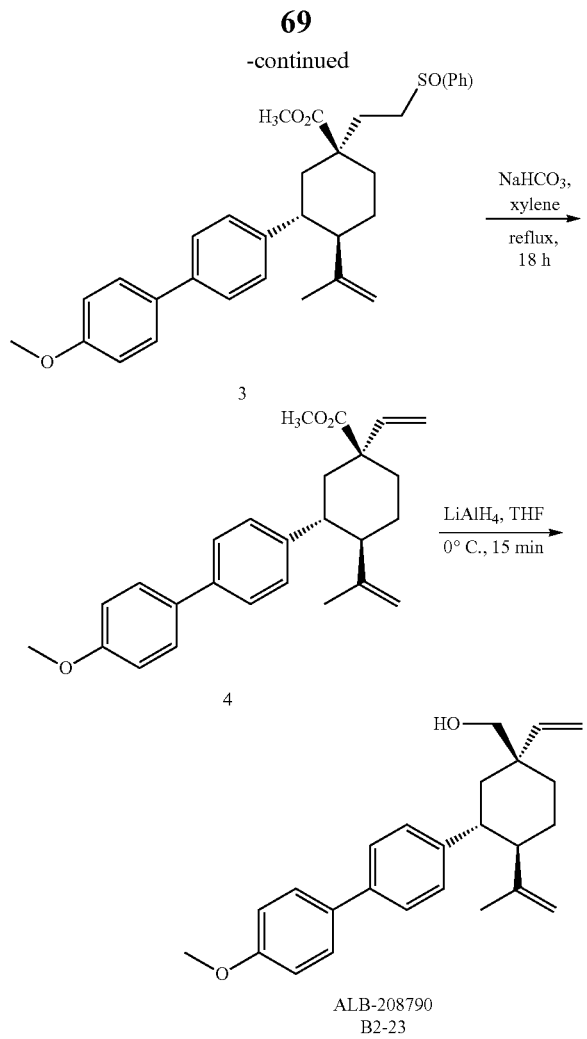

3

4

ALB-208790
B2-23

Production of Chemical Compound 2

Chemical compound 1 (0.27 g, 1.78 mmol) and $Na_2CO_3$ (2 M, 0.19 g, 1.79 mmol) were added to a solution of chemical compound Int-7 (chemical compound 7 in scheme 20) (0.30 g, 0.89 mmol) dissolved in 1,4-dioxane (3.0 mL), and the solution was degassed with argon for 15 minutes. Pd(dppf)$Cl_2 \cdot CH_2Cl_2$ complex (0.07 g, 0.09 mmol) was added to the reaction mixture. The obtained mixture was stirred and refluxed under microwave irradiation for 1 hour. The residual solvent was evaporated. The crude product was dissolved in $CH_2Cl_2$ (10 mL) and filtered through a Celite bed. The filtrate was washed with water (10 mL), dried over anhydrous $Na_2SO_4$, filtered, and concentrated under reduced pressure. The residue was purified by column chromatography using 0-20% EtOAc in hexane to obtain chemical compound 2 (0.26 g, 80%) as an off-white solid.

Production of Chemical Compound 3

At $-78°$ C., chemical compound 2 (0.29 g, 0.79 mmol) dissolved in THF (3.0 mL) was dropped to a solution of lithium diisopropylamide (1.20 mL, 2.0 M in THF, 2.38 mmol) dissolved in THF (5.0 mL). The solution was stirred at $-78°$ C. for 30 minutes, then cooled to $-105°$ C. (MeOH, liquid $N_2$), and phenyl vinyl sulfoxide (0.24 g, 1.59 mmol) was added to the reaction mixture. The reaction mixture was stirred at $-105°$ C. for 30 minutes and quenched with saturated $NH_4Cl$ solution (5.0 mL). The obtained mixture was extracted with EtOAc (10 mL×2). The organic layer was mixed, washed with brine (5.0 mL), dried over $MgSO_4$ and concentrated under reduced pressure. The residue was purified by column chromatography using 0-20% EtOAc in hexane to obtain chemical compound 3 (0.16 g, 40%) as a brown liquid.

Production of Chemical Compound 4

A mixture of $NaHCO_3$ (0.328 g, 3.10 mmol) and chemical compound 3 (0.16 g, 0.31 mmol) dissolved in xylene (3.0 mL) was stirred under reflux for 18 hours and diluted with $H_2O$. The obtained mixture was extracted with EtOAc (10 mL×2). The organic layer was mixed, washed with brine (5.0 mL), dried over $MgSO_4$ and concentrated to obtain the residual oil. It was purified by column chromatography using 0-20% EtOAc in hexane to obtain chemical compound 4 (0.04 g, 33%) as a colored oil. ESI MS m/z 391 [M+H]$^+$.

Production of Chemical Compound ALB-208790 (B2-23)

At 0° C., LiAlH$_4$ (0.2 mL, 2.0 M in THF, 0.30 mmol) was added to an ice-cold solution of chemical compound 4 (0.04 g, 0.10 mmol) dissolved in THF (4.0 mL). The reaction mixture was stirred at 0° C. for 15 minutes and diluted with $H_2O$ and $Na_2SO_4 \cdot 10H_2O$. The obtained mixture was extracted with EtOAc (5.0 mL×3). The organic layer was mixed, washed with brine (5.0 mL), dried with $Na_2SO_4$ and concentrated under reduced pressure. The residue was purified by column chromatography using 0-30% EtOAc in hexane to obtain chemical compound ALB-208790(B2-23) (0.015 g, 40%) as an off-white solid. $^1$H NMR (400 MHz, CDCl$_3$) δ 7.51 (d, J=8.8 Hz, 2H), 7.45 (d, J=8.0 Hz, 2H), 7.19 (d, J=8.0 Hz, 2H), 6.95 (d, J=8.8 Hz, 2H), 5.79-5.71 (m, 1H), 5.17-5.06 (m, 2H), 4.58 (d, 2H), 3.82 (s, 3H), 2.81-2.75 (m, 1H), 2.37-2.30 (m, 2H), 1.94-1.88 (m, 2H), 1.73-1.66 (m, 2H), 1.50-1.43 (m, 5H); ESI MS m/z 363 [M+H]$^+$.

Synthesis Example 21

Synthesis of Chemical Compound B2-5B

A method for the production of chemical compound B2-5B (also called ALB-210363) is as follows (also called scheme 22).

[Chemical 67]

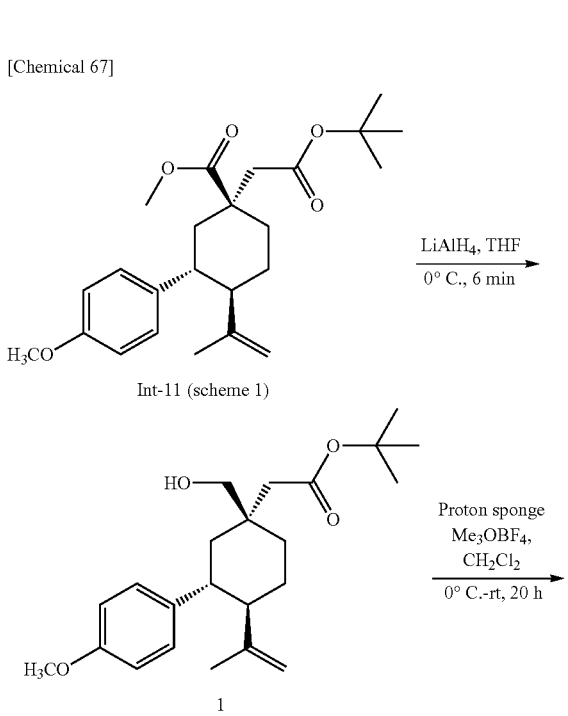

Int-11 (scheme 1)

1

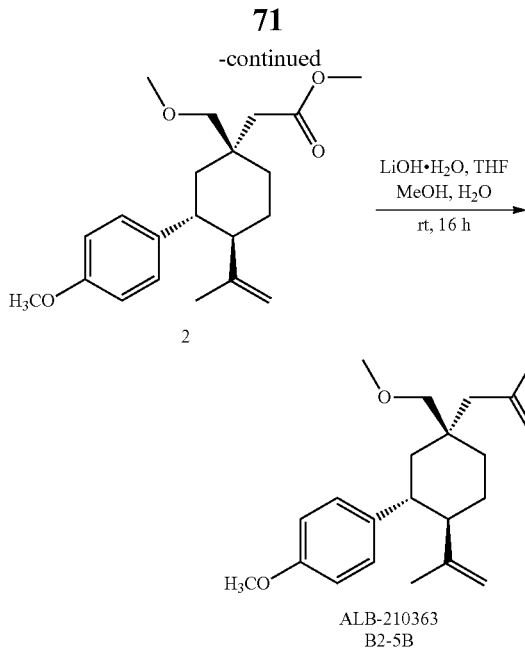

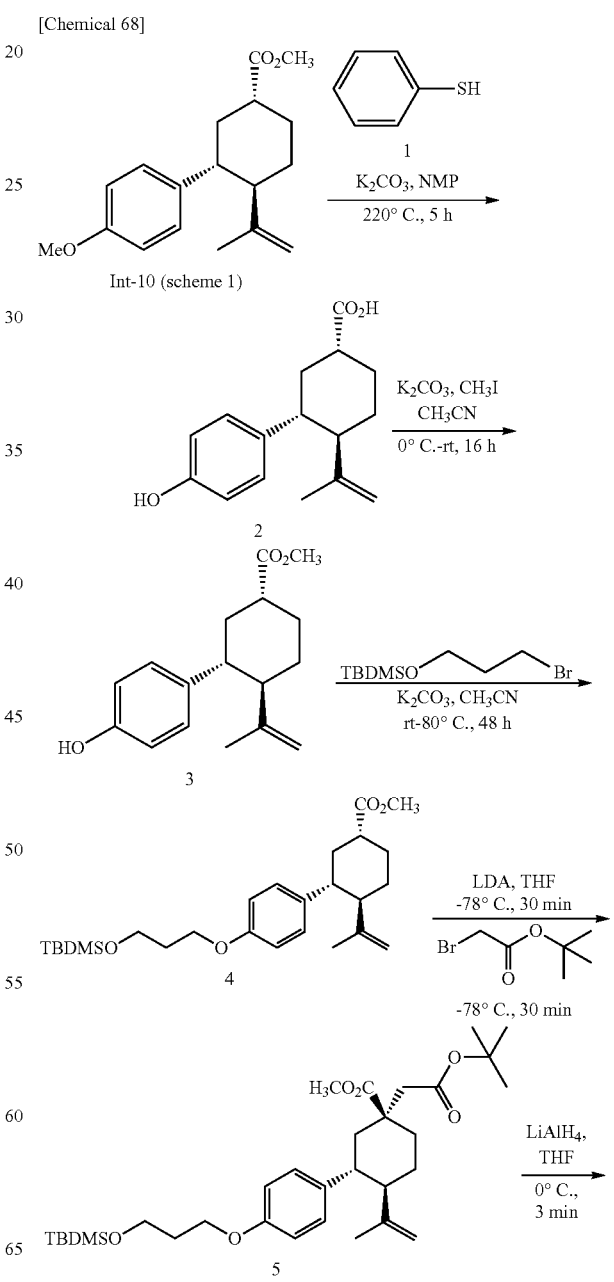

1H), 2.388 (s, 2H), 2.31-2.18 (m, 2H), 1.91 (t, 14.8 Hz, 2H), 1.51 (m, 1H), 1.50 (s, 3H), 1.49-1.37 (m, 3H); ESI MS m/z 331.2 $C_{20}H_{28}O_4$—H]$^+$.

Preparative HPLC Conditions:
 Column: Gemini NX-C18 10 μm; 150×30 mm
 Mobile phase A: 0.05% formic acid solution;
  B: Acetonitrile
 Gradient (T/% B): 0/10, 2/30, 10/75, 15/95, 15.5/98, 17.5/98, 18/20, 20/10
 Diluent: MeOH+THF Synthesis Example 22

Synthesis of Chemical Compound B2-5A-7

A method for the production of chemical compound B2-5A-7 (also called ALB-211303) is as follows (also called scheme 23).

[Chemical 68]

Production of Chemical Compound 1

At 0° C., LiAlH$_4$ (0.37 mL, 2.0 M in THF, 0.746 mmol) was added to an ice-cold solution of chemical compound Int-11 (chemical compound 11 in scheme 1) (0.15 g, 0.373 mmol, IN-BSC-J-51) dissolved in THF (5.0 mL). The reaction mixture was stirred at 0° C. for 6 minutes. The progress of the reaction was monitored by TLC, and the mixture was quenched with Na$_2$SO$_4$.10H$_2$O and concentrated under reduced pressure. The residue was purified by column chromatography using 0-30% EtOAc in hexane to obtain chemical compound 1 (0.045 g, 32%) as a colorless viscous material. ESI MS m/z 375 $C_{23}H_{24}O_4$+H]$^+$.

Production of Chemical Compound 2

At 0° C., Proton Sponge® (Sigma-Aldrich) (0.0859 g, 0.40 mmol) and Me$_3$OBF$_4$ (0.059 g, 0.40 mmol) in that order were added to an ice-cold solution of chemical compound 1 (0.03 g, 0.080 mmol) dissolved in CH$_2$Cl$_2$ (10 mL). The reaction mixture was stirred at room temperature for 20 hours. The reaction mixture was diluted with water (25 mL) and extracted with CH$_2$Cl$_2$ (25 mL×2). The organic layer was mixed, dried over anhydrous Na$_2$SO$_4$, filtered, and concentrated under reduced pressure to obtain the crude product. The crude product was purified by column chromatography using 0-6% EtOAc in hexane to obtain chemical compound 2 (0.022 g, 79%) as a colorless viscous material.

Production of Chemical Compound ALB-210363 (B2-5B)

LiOH·H$_2$O (0.013 g, 0.317 mmol) was added to a stirred solution of chemical compound 2 (0.022 g, 0.0635 mmol) dissolved in water (0.5 mL), THF (2.0 mL) and MeOH (1.0 mL). The reaction was stirred at room temperature for 16 hours and concentrated under reduced pressure. The residue was diluted with water (25 mL), acidified with HCl solution (2N, 3.0 mL), and extracted with EtOAc (25 mL×2). The organic layer was mixed, dried over anhydrous Na$_2$SO$_4$, filtered, and concentrated under reduced pressure to obtain the crude product. The crude product was purified by preparative-HPLC column chromatography and the fraction was evaporated by lyophilization to obtain chemical compound ALB-210363(B2-5B) (0.006 g, 28%) as an off-white solid. $^1$H NMR (400 MHz, CDCl$_3$) δ 7.01 (d, J=8.4 Hz, 2H), 6.77 (d, J=8.4 Hz, 2H), 4.55 (s, 2H), 3.75 (s, 3H), 3.63 (d, 9.2 Hz, 1H), 3.56 (d, 9.2 Hz, 1H), 3.44 (s, 3H), 2.67-2.57 (m,

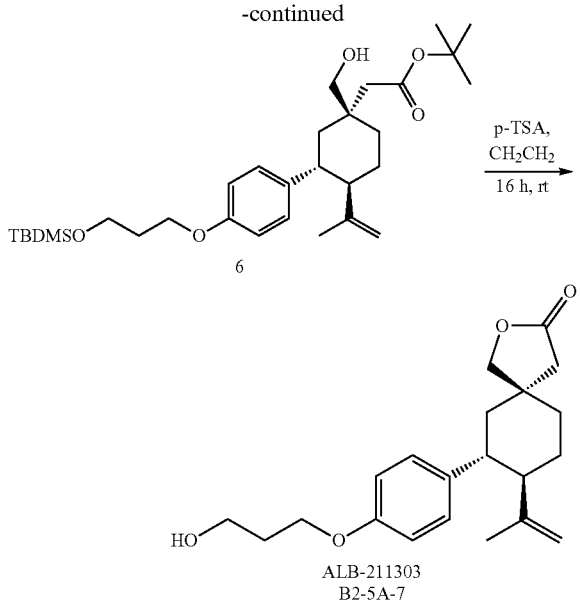

Production of Chemical Compound 2

At room temperature, chemical compound 1 (1.1 mL, 10.4 mmol) was added to a suspension of $K_2CO_3$ (0.718 g, 5.202 mmol) and chemical compound Int-10 (chemical compound 10 of scheme 1) (0.75 g, 2.60 mmol) dissolved in NMP (8.0 mL). The reaction was carried out in a sealed tube at 220° C. for 5 hours and quenched by the addition of HCl solution (2N, 40 mL). The obtained mixture was extracted with MTBE (60 mL×3), dried over $Na_2SO_4$ and concentrated under reduced pressure to obtain the residue. It was purified by combiflash column chromatography using 0-80% EtOAc in hexane to obtain chemical compound 2 (0.38 g, 56%) as a pale yellow solid. ESI MS m/z 259 $[C_{16}H_{20}O_3-H]^+$.

Production of Chemical Compound 3

At 0° C., $K_2CO_3$ (0.604 g, 4.38 mmol) and methyl iodide (0.415 g, 2.92 mmol) in that order were added to a stirred solution of chemical compound 2 (0.38 g, 1.46 mmol) dissolved in acetonitrile (20 mL). The reaction was carried out at room temperature for 16 hours, filtered, and concentrated under reduced pressure to obtain the residue. It was purified by combiflash column chromatography using 0-50% EtOAc in hexane to obtain chemical compound 3 (0.33 g, 82%) as a colorless viscous liquid.

Production of Chemical Compound 4

At room temperature, $K_2CO_3$ (0.603 g, 4.374 mmol) and (3-bromopropoxy)(tert-butyl)dimethylsilane (0.44 g, 1.74 mmol) in that order were added to a stirred solution of chemical compound 3 (0.4 g, 1.458 mmol) dissolved in acetonitrile (20 mL). The reaction was carried out at 80° C. for 48 hours, filtered, and concentrated under reduced pressure to obtain the residue. It was purified by combiflash column chromatography using 0-20% EtOAc in hexane to obtain chemical compound 4 (0.52 g, 79.8%) as a colorless liquid.

Production of Chemical Compound 5

At −78° C., lithium diisopropylamide (1.74 mL, 2.0 M in THF, 3.492 mmol) was dropped to a stirred solution of chemical compound 4 (0.52 g, 1.164 mmol) dissolved in THF (8.0 mL). The solution was stirred at −78° C. for 30 minutes, then tert-butyl 2-bromoacetate (0.454 g, 2.32 mmol) was added to the reaction mixture. The reaction mixture was stirred at −78° C. for 30 minutes and quenched with saturated $NH_4Cl$ solution (10 mL). The obtained mixture was extracted with EtOAc (50 mL×2). The organic layer was mixed, washed with brine (20 mL), dried over $Na_2SO_4$ and concentrated under reduced pressure. The residue was purified by combiflash column chromatography using 0-10% EtOAc in hexane to obtain chemical compound 5 (0.36 g, 55%) as a colorless viscous liquid.

Production of Chemical Compound 6

At 0° C., $LiAlH_4$ (2.0 M in THF, 0.5 mL, 0.962 mmol) was added to an ice-cold solution of chemical compound 5 (0.18 g, 0.328 mmol) dissolved in THF (6.0 mL). The reaction mixture was stirred at 0° C. for 3 minutes and quenched with saturated $NH_4Cl$ (5.0 mL). The obtained mixture was extracted with EtOAc (30 mL×2). The organic layer was mixed, washed with brine (10 mL), dried over $Na_2SO_4$ and concentrated under reduced pressure to obtain the residue. It was purified by combiflash column chromatography using 0-30% EtOAc in hexane to obtain chemical compound 6 (0.065 g, 38%) as a colorless liquid.

Production of Chemical Compound ALB-211303 (B2-5A-7)

At room temperature, p-toluenesulfonic acid monohydrate (0.696 g, 0.365 mmol) was added to a stirred solution of chemical compound 6 (0.065 g, 0.1219 mmol) dissolved in $CH_2Cl_2$ (5.0 mL). The reaction mixture was stirred at room temperature for 16 hours. The reaction mixture was diluted with $CH_2Cl_2$ (50 mL) and washed with saturated $NaHCO_3$ solution (30 mL) and brine (20 mL). The organic layer was dried with $Na_2SO_4$ and concentrated under reduced pressure. The residue was purified by combiflash column chromatography using 0-30% EtOAc in hexane on silica gel to obtain chemical compound ALB-211303(B2-5A-7) (0.014 g, 33%) as a colorless viscous material. $^1$H NMR (400 MHz, $CDCl_3$) δ 7.01 (d, J=8.8 Hz, 2H), 6.80 (d, J=8.8 Hz, 2H), 4.57 (d, J=1.2 Hz, 2H), 4.30-4.25 (q, 2H), 4.09 (t, J=6.0 Hz, 2H), 3.85 (d, J=4.4 Hz, 2H), 2.56-2.45 (m, 1H), 2.34 (d, J=3.2 Hz, 2H), 2.29-2.22 (m, 1H), 2.08-2.00 (m, 2H), 1.93-1.86 (m, 2H), 1.81-1.77 (m, 2H), 1.66-1.52 (m, 3H), 1.49 (s, 3H); ESI MS m/z 345 $C_{21}H_{28}O_4+H]^+$.

Synthesis Example 23

Synthesis of Chemical Compound B2-5A-7-1

A method for the production of chemical compound B2-5A-7-1 (also called ALB-211355) is as follows (also called scheme 24).

[Chemical 69]

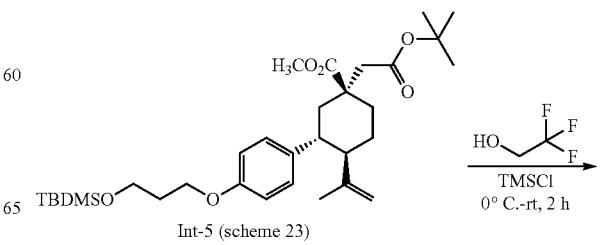

Int-5 (scheme 23)

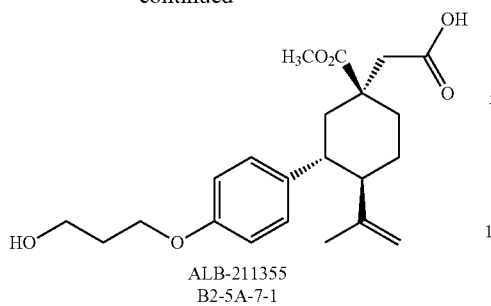

ALB-211355
B2-5A-7-1

At 0° C., TMSCl (0.075 mL) was added to an ice-cold solution of chemical compound Int-5 (chemical compound 5 in scheme 23) (0.05 g, 0.0891 mmol) dissolved in 2,2,2-trifluoroethanol (0.25 mL). The reaction mixture was then heated to room temperature and stirred for 2 hours. The progress of the reaction was monitored by TLC. The reaction mixture was concentrated under reduced pressure to obtain a crude product. The crude product was purified by preparative-HPLC column chromatography and the fraction was evaporated by lyophilization to obtain chemical compound ALB-211355(B2-5A-7-1) (0.01 g, 28.7%) as a colorless viscous material. $^1$H NMR (400 MHz, CDCl$_3$) δ 7.04 (d, J=8.8 Hz, 2H), 6.79 (d, J=8.4 Hz, 2H), 4.53 (d, J=1.2 Hz, 2H), 4.08 (t, J=5.8 Hz, 2H), 3.85 (t, J=5.8 Hz, 2H), 3.759 (s, 3H), 2.86-2.75 (m, 1H), 2.63 (d, J=15.2 Hz, 1H), 2.49 (d, J=15.2 Hz, 1H), 2.39-2.19 (m, 4H), 2.08-1.98 (m, 2H), 1.75-1.60 (m, 2H), 1.47 (s. 3H), 1.47-1.3 (m, 2H); ESI MS m/z 391 C$_{22}$H$_{30}$O$_6$+H]$^+$.

Preparative HPLC Conditions.

Column: Gemini NX-C18 10 μm; 150×30 mm

Mobile phase: B: acetonitrile;

A: 0.05% formic acid solution

Gradient (min/% B): 0/10, 2/30, 10/55, 15/85, 15.5/98, 18.5/98, 19/10, 20/10

Diluent: MeOH

Column flow rate: 30 mL/min

Synthesis Example 24

Synthesis of Chemical Compound B2-5A-1

A method for the production of chemical compound B2-5A-1 (also called ALB-210360) is as follows (also called scheme 25).

[Chemical 70]

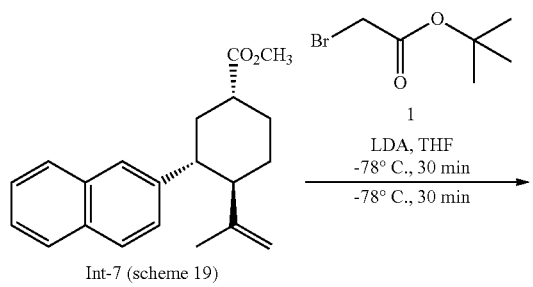

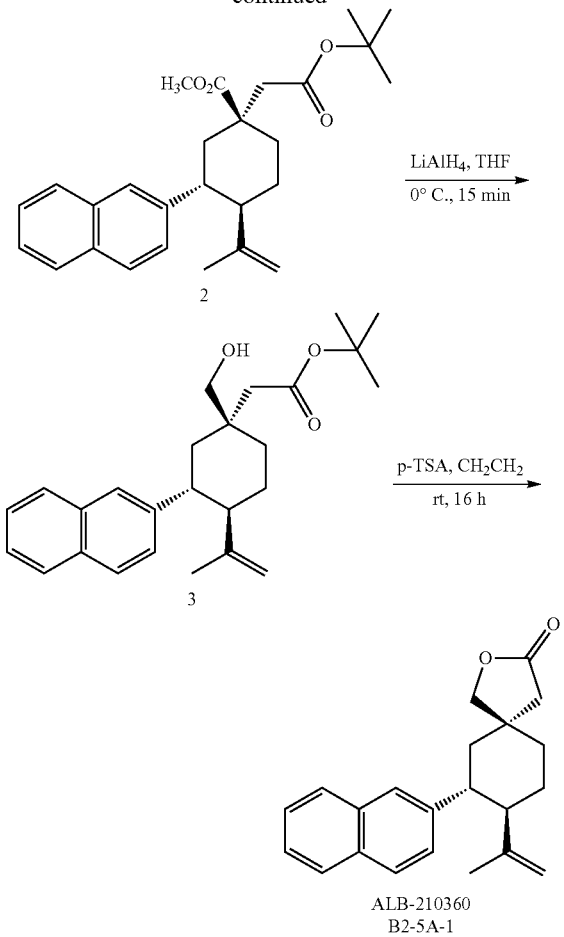

Production of Chemical Compound 2

At −78° C., chemical compound Int-7 (chemical compound 7 in scheme 19) (0.05 g, 0.162 mmol) was dropped to a solution of lithium diisopropylamide (0.24 mL, 2.0 M in THF, 0.41 mmol) dissolved in THF (2.0 mL). The solution was stirred at −78° C. for 30 minutes, then chemical compound 1 (0.04 mg, 0.19 mmol) was added thereto. The reaction mixture was stirred at −78° C. for 30 minutes and quenched with saturated NH$_4$Cl solution (5.0 mL). The obtained mixture was extracted with EtOAc (10 mL×3). The organic layer was mixed, washed with brine (5.0 mL), dried over Na$_2$SO$_4$ and concentrated. The residue was purified by combiflash column chromatography using 0-10% EtOAc in hexane to obtain chemical compound 2 (0.03 g, 44%) as a colorless liquid. $^1$H NMR (400 MHz, CDCl$_3$) δ 7.74 (d, J=8.4 Hz, 2H), 7.57 (s, 1H), 7.45-7.30 (m, 3H), 4.58-4.47 (m, 2H), 3.81 (s, 3H), 3.05-2.98 (m, 1H), 2.59-2.43 (m, 9H), 1.75-1.70 (m, 2H), 1.68-1.67 (m, 1H), 1.45 (s, 3H), 1.39 (s, 9H).

Production of Chemical Compound 3

At 0° C., LiAlH$_4$ (0.14 mL, 1.0 M in THF, 0.14 mmol) was added to an ice-cold solution of chemical compound 2 (0.03 g, 0.07 mmol) dissolved in THF (3.0 mL). The reaction mixture was stirred at 0° C. for 15 minutes and diluted with H$_2$O and Na$_2$SO$_4$·10H$_2$O. The obtained mixture was extracted with EtOAc (5.0 mL×3). The organic layer was mixed, washed with brine (5.0 mL), dried with Na$_2$SO$_4$ and concentrated under reduced pressure. The residue was purified by combiflash column chromatography using 0-30%

EtOAc in hexane to obtain chemical compound 3 (0.01 g, 36%) as a colorless oil. $^1$H NMR (400 MHz, CDCl$_3$) δ 7.74-7.71 (m, 3H), 7.55 (s, 1H), 7.43-7.36 (m, 2H), 7.31, 7.28 (dd, J=1.6, 8.4 Hz, 2H), 4.57-4.46 (m, 2H), 3.82 (t, J=6.0 Hz, 2H), 3.07-2.85 (m, 1H), 2.44-2.35 (m, 2H), 2.22 (s, 2H), 1.96-1.87 (m, 3H), 1.69-1.65 (m, 3H), 1.49 (s, 4H), 1.41 (s, 9H).

Production of Chemical Compound ALB-210360 (B2-5A-1)

At room temperature, p-TSA (0.009 g, 0.05 mmol) was added to an ice-cold solution of chemical compound 3 (0.01 g, 0.025 mmol) dissolved in CH$_2$Cl$_2$ (1.0 mL). The reaction mixture was stirred at room temperature for 16 hours and diluted with H$_2$O. The obtained mixture was extracted with EtOAc (5.0 mL×3). The organic layer was mixed, washed with brine (5.0 mL), dried with Na$_2$SO$_4$ and concentrated under reduced pressure. The residue was purified by combiflash column chromatography using 0-20% EtOAc in hexane and preparative HPLC to obtain chemical compound ALB-210360(B2-5A-1) (0.0008 g) as an off-white solid. $^1$H NMR (400 MHz, CDCl$_3$) δ 7.77-7.72 (m, 3H), 7.52 (s, 1H), 7.42-7.39 (m, 3H), 4.58-4.50 (m, 2H), 4.31 (s, 2H), 2.74-2.67 (m, 1H), 2.46-2.39 (m, 1H), 2.34 (d, J=3.6 Hz, 2H), 1.96-1.72 (m, 3H), 1.66-1.60 (m, 2H), 1.49 (s, 3H); ESI MS m/z 321 C$_{22}$H$_{24}$O$_2$+H]$^+$.

Synthesis Example 25

Synthesis of Chemical Compounds B2-2A and B2-3A

A method for the production of chemical compounds B2-2A (also called ALB-210365) and B2-3A (also called ALB-210797) is as follows (also called scheme 26).

[Chemical 71]

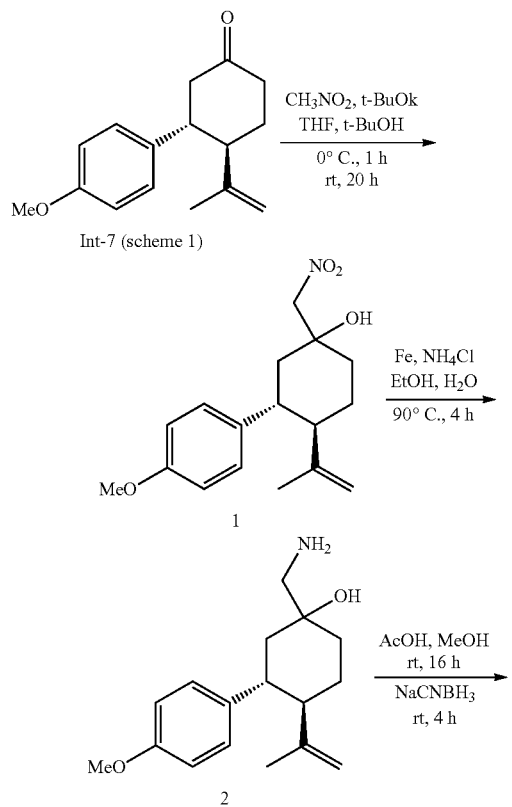

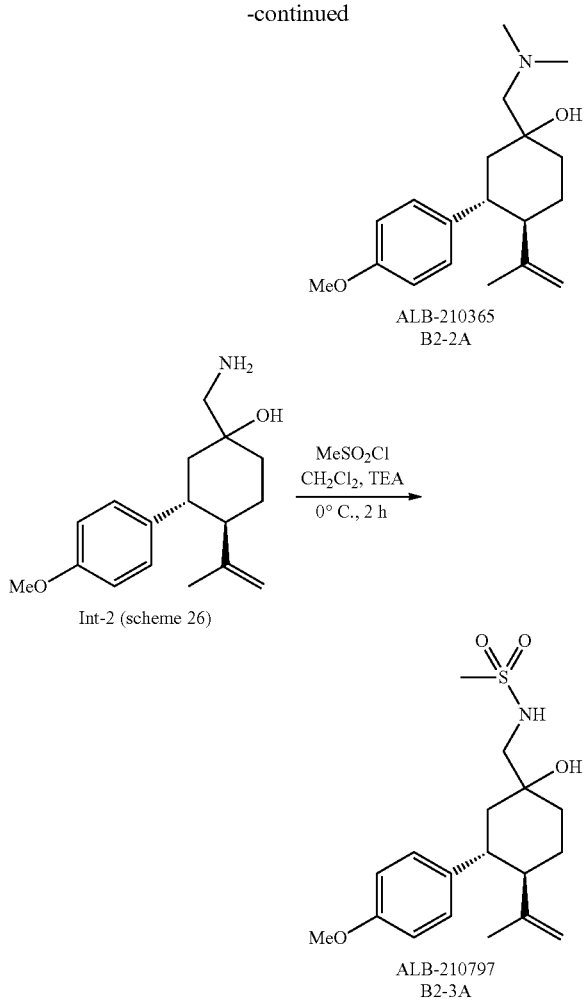

Production of Chemical Compound 1 t-BuOK (0.0137 g, 0.122 mmol) and CH$_3$NO$_2$ (0.01 g, 0.1639) in that order were added to a solution (0° C.) of chemical compound Int-7 (chemical compound 7 in scheme 1) (0.02 g, 0.081 mmol) dissolved in t-BuOH (2.0 mL) and THF (3.0 mL), and the mixture was stirred at 0° C. for 1 hour. The reaction mixture was then stirred at room temperature for 20 hours. The reaction mixture was diluted with saturated NH$_4$Cl (20 mL), extracted with MTBE (2×20 mL), dried over anhydrous Na$_2$SO$_4$, filtered and concentrated to obtain a crude product. The crude product was purified by column chromatography using 0-20% EtOAc in hexane to obtain chemical compound 1 (0.005 g, 20%) as a colorless liquid. ESI MS m/z 306 C$_{17}$H$_{23}$NO$_4$+H]$^+$.

Production of Chemical Compound 2

Fe (0.036 g, 0.655 mmol) and NH$_4$Cl (0.034 g, 0.655 mmol) in that order were added to a stirred solution of chemical compound 1 (0.05 g, 0.163 mmol) dissolved in H$_2$O (2.0 mL) and EtOH (5.0 mL), and the solution was stirred at 90° C. for 4 hours. The reaction mixture was filtered through celite, diluted with water (40 mL) and extracted with CH$_2$Cl$_2$ (50 mL×2). The organic layer was washed with brine (10 mL), dried over anhydrous Na$_2$SO$_4$, filtered, and concentrated under reduced pressure to obtain chemical compound 2 [0.055 g (crude)] as a brown liquid. The crude product was used in the next step without purification.

Production of Chemical Compound ALB-210365 (B2-2A)

At room temperature, formaldehyde (1.0 mL) was added to a stirred solution of chemical compound 2 (0.045 g, 0.163 mmol) dissolved in MeOH (5.0 mL) followed by in AcOH (0.02 mL) and the solution was stirred for 16 hours at room temperature. NaCNBH$_3$ (0.030 g, 0.490 mmol) was added to the reaction mixture at 0° C. The reaction mixture was then stirred at room temperature for 4 hours. The reaction mixture was diluted with saturated NaHCO$_3$ (40 mL) and extracted with CH$_2$Cl$_2$ (50 mL×2). The organic layer was mixed, dried with anhydrous Na$_2$SO$_4$, filtered, and concentrated under reduced pressure to obtain the crude product. The crude product was purified by preparative-HPLC column chromatography and the fraction was evaporated by lyophilization to obtain chemical compound ALB-210365(B2-2A) (0.02 g, 40%) as a colorless viscous liquid. $^1$H NMR (400 MHz, CDCl$_3$) δ 7.09 (d, J=8.8 Hz, 2H), 6.80 (d, J=8.7 Hz, 2H), 4.58 (d, J=15.2 Hz, 2H), 3.78 (s, 3H), 3.15-3.02 (m, 1H), 2.86-2.74 (m, 1H), 2.73 (s, 6H), 2.72-2.62 (m, 1H), 2.45-2.35 (m, 1H), 2.12-1.98 (m, 3H), 1.71-1.61 (m, 1H), 1.55 (s, 3H), 1.48-1.35 (m, 3H); ESI MS m/z 304 C$_{19}$H$_{29}$NO$_2$+H]$^+$.

Preparative HPLC Conditions.
   Column: Gemini NX-C18 10 μm; 150×30 mm
   Mobile phase: A: acetonitrile;
     B: 10 mm ammonium formate solution
   Gradient (min/% A): 0/10, 2/20, 10/40, 15/60, 15.5/98, 18/98, 18.2/10, 20/10
   Diluent: MeOH+THF Production of Chemical Compound ALB-210797 (B2-3A)

At 0° C., triethylamine (0.007 g, 0.072 mmol) and mesyl-chloride (0.004 g, 0.036) in that order were added to a stirred solution of chemical compound Int-2 (chemical compound 2 in scheme 26) (0.01 g, 0.036 mmol) dissolved in CH$_2$Cl$_2$ (5.0 mL). The reaction mixture was then stirred at 0° C. for 2 hours. The reaction mixture was diluted with water (20 mL) and extracted with CH$_2$Cl$_2$ (30 mL×2). The organic layer was mixed, dried with anhydrous Na$_2$SO$_4$, filtered, and concentrated under reduced pressure to obtain the crude product. The crude product was purified by preparative HPLC column chromatography and the fraction was evaporated by lyophilization to obtain chemical compound ALB-210797 (B2-3A) (0.004 g, 31%) as an off-white solid. $^1$H NMR (400 MHz, CDCl$_3$) δ 7.04 (d, J=8.8 Hz, 2H), 6.79 (d, J=8.4 Hz, 2H), 4.74 (t, J=6.4 Hz, 1H), 4.56 (d, J=8.4 Hz, 2H), 3.76 (s, 3H), 3.15-3.02 (m, 2H), 2.97 (s, 3H), 2.96-2.84 (m, 1H), 2.32-2.20 (m, 1H), 1.98 (brs, 1H), 1.92-1.83 (m, 3H), 1.72-1.65 (m, 1H), 1.52 (s, 3H), 1.51-1.38 (m, 2H); ESI MS m/z 352 C$_{18}$H$_{27}$NO$_4$S–H]$^+$.

Preparative HPLC Conditions.
   Column: Gemini NX-C18 10 μm; 150×30 mm
   Mobile phase: A: acetonitrile;
     B: 0.05% formic acid solution
   Gradient (min/% A): 0/10, 2/30, 10/60, 15/80, 15.2/98, 18/98, 18.2/10, 20/10
   Diluent: MeOH+THF Example 2: Evaluation of TLR7 Activation Inhibition in Each Derivative Mouse TLR7-expressing reporter cells (Ba/F3 cells) were used to evaluate inhibition of TLR7 activation in each derivative and CB-7. These cells were provided by Professor Kensuke Miyake (Department of Infection Genetics, Institute of Medical Science, University of Tokyo). These cells have been transfected with a reporter gene that connects GFP gene downstream of the promoter region of NF-κB. Therefore, the expression of GFP is enhanced by the addition of a ligand for TLR7 expressed by the cells. The fluorescence intensity of GFP was attenuated by the addition of each derivative, and the inhibition of TLR7 activation by each derivative was evaluated as an indicator.

Loxoribine (Alexis Biochemicals) was used as the ligand for mouse TLR7. Gardiquimod (Invivogen) was used as the ligand for human TLR7.

Ba/F3 cells cultured in RPMI 1640 medium containing 10% (v/v) fetal calf serum (FCS), 50 U/mL penicillin, 50 μg/mL streptomycin, 2 mM L-glutamine, 50 M 2-mercaptoethanol, 1 ng/mL interleukin-3 were aliquoted into 96-well plates so that the number of cells per well was 1.0×10$^5$ cells/100 μL. 50 μL of each derivative or CB-7, prepared to final concentrations of 1, 5, 10, 25, 50, and 100 M, was added to each well. 96-well plates were incubated at 37° C. for 30 minutes in the presence of 5% CO$_2$. Next, 250 μg/mL Roxoribin was added to each well and incubated for 18 hours. At the end of incubation, cells were washed with PBS (FACS buffer) containing 2.5% (v/v) FCS and suspended in 200 μL of FACS buffer containing 25 μg/mL 7-actinomycin D for each cell. GFP fluorescence intensities of the cells were analyzed by flow cytometry. Flow cytometry measurement was performed on a FACSCanto™ II (Becton Dickinson) and data were analyzed with FlowJo software (Tree Star). The MFI (%) upon stimulation with roxoribin in the presence of 1-100 M derivatives or CB-7 was calculated using the MFI upon stimulation with roxoribin alone as 100%, and then IC$_{50}$ (chemical compound concentration that inhibits activity by 50%) was calculated by logistic regression analysis.

The IC$_{50}$ of each derivative is shown in Table 3. IC$_{50}$ of CB-7 was 3.12 μM.

TABLE 3

IC$_{50}$ of CB-7 derivatives with modified Areas a and b

| I-7(Intermediate) | B2-2A | B2-3A | B2-5A |
|---|---|---|---|
| >100 μM | >100 μM | >10 μM | 2.43 μM |
| B2-5B | B2-6 | B2-6A | B2-6-7 |
| >100 μM | >100 μM | >100 μM | 9.36 μM |
| B2-13 | B2-18 | B2-19 | B2-21 |
| 0.91 μM | >50 μM | >100 μM | >50 μM |
| B2-22 | B2-23 | B2-24 | B2-26 |
| 0.31 μM | >100 μM | 0.44 μM | 1.26 μM |
| B2-27 | B2-28 | B2-29 | B2-24-1 |
| >100 μM | 1.66 μM | 1.74 μM | 1.05 μM |
| B2-24-2 | B2-24-3 | B2-24-4·HCl | B2-5A-1 |
| 0.71 μM | 1.26 μM | 0.087 μM | >100 μM |
| B2-5A-7-1 | B2-5A-4 | B2-5A-6 | B2-5A-7 |
| >10 μM | 2.57 μM | 0.21 μM | 2.50 μM |
| B2-5A-9 | | | |
| 0.3 μM | | | |

As shown in Table 3, the derivatives that had higher TLR7 activation inhibitory activity than CB-7 were B2-5A, B2-13, B2-22, B2-24, B2-26, B2-28, B2-29, B2-24-1, B2-24-2, B2-24-3, B2-24-4·HCl, B2-5A-4, B2-5A-6, B2-5A-7 and B2-5A-9. Among these derivatives, those that had more than 2-fold higher TLR7 activation inhibitory activity than CB-7 were B2-13, B2-22, B2-24, B2-26, B2-24-1, B2-24-2, B2-24-3, B2-24-4·HCl, B2-5A-6 and B2-5A-9. B2-24-4·HCl had the highest TLR7 activation inhibitory activity compared to the other derivatives.

In addition, it was suggested that the introduction of an N atom into Area b was important for the development of high activity. Replacement of Area a with a lactone ring did not affect TLR7 activation inhibitory activity.

Example 3: Analysis of Metabolic Stability (Cytochrome P450 (CYP)) of B2-24 and B2-5A Using Mouse Liver Microsomes For CB-7, B2-24, and B2-5A, 10 mg/mL DMSO solution was used. Each chemical compound was diluted with acetonitrile to 0.1 mg/mL, which was used as the analytical standard. Mouse liver microsomal fractions were rapidly thawed in a warm bath at 37° C. and kept on ice. Reaction buffer containing CYP cofactor was prepared on ice and mixed with the microsomal fractions. The reaction solution was preincubated at 37° C. for 5 minutes, and then the test substance solution was added and mixed well by pipetting. The volume of the reaction solution was 200 μL and the final concentration of the test substance was 0.1 mg/mL. The reaction solution was incubated at 37° C. for 30 minutes or 2 hours, and the reaction was stopped by adding 3 times the volume of acetonitrile and vortexing. After the reaction was stopped, the samples were centrifuged, and each supernatant was separated and dried in an evaporator. 50 μL of 50% acetonitrile solution was added to each solidified sample, and each sample was re-dissolved by vortexing for 5 minutes. Each redissolved solution was centrifuged, and each supernatant was subjected to HPLC analysis using a HITACHI Lachrom ELITE (HITACHI) as a HPLC system and COSMOSIL 5$C_{18}$-MS-II, 4.6 mmI.D.×150 mm (nacalai tesque Co.) as a column. Results are shown in Table 4.

The number of peaks detected by HPLC in CB-7 was 7. On the other hand, the number of peaks detected by HPLC in B2-24 and B2-5A was 4, which was less than that of CB-7. Therefore, B2-24 and B2-5A improved drug metabolism mainly by CYPs compared to CB-7. Based on these results, it was predicted that the hybrid derivatives of B2-24 and B2-5A would have higher TLR7 inhibitory activity and still improve metabolic stability.

Example 4: Synthesis of Hybrid Derivative (B2-24-4-5A) of B2-24-4·HCl and B2-5A We commissioned Albany Molecular Research Inc. (USA) to prepare a hybrid derivative (B2-24-4-5A) of B2-24-4·HCl (a derivative with a similar structure to B2-24 and the highest TLR7 inhibitory activity) and B2-5A shown below. The structure is represented by the following formula (X).

[Chemical 72]

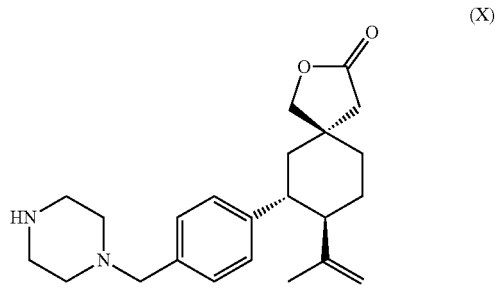

(X)

TABLE 4

| | Name | | |
|---|---|---|---|
| | CB-7 | B2-24 | B2-5A |
| Chemical structure | (structure shown) | (structure shown) | (structure shown) |
| Number of peaks detected by HPLC | 7 | 4 | 4 |
| Predicted metabolic modifications (CYP) | +O<br>+2O<br>+2OH | +O<br>+2OH | +O |

The structure of B2-24-4-5A·HCOOH is represented by the following formula (XIV).
[Chemical 73]
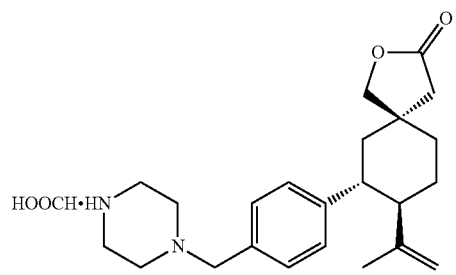
(XIV)
Synthesis Example 26
Synthesis of Chemical Compounds B2-24-4-5A and B2-24-4-5A·HCOOH
A method for the production of chemical compounds B2-24-4-5A and B2-24-4-5A·HCOOH is as follows (also called scheme 27).
[Chemical 74]
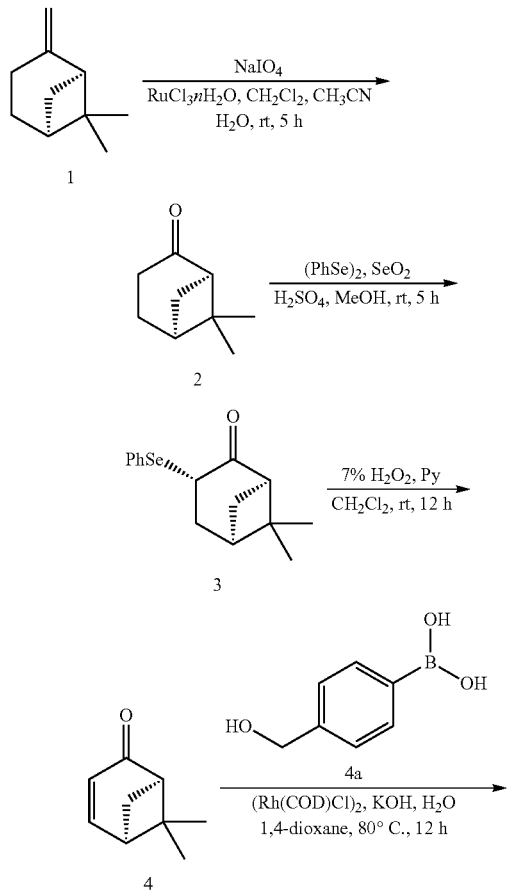
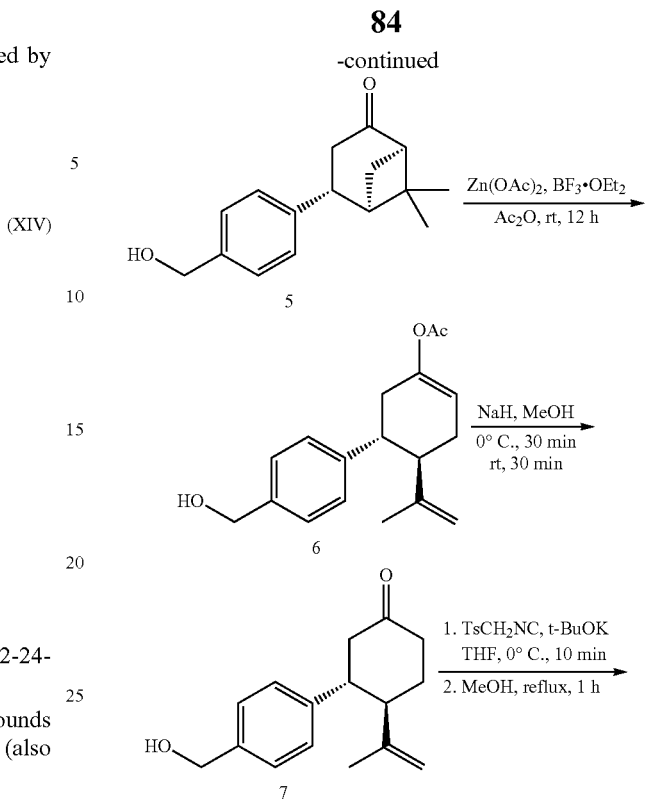

-continued

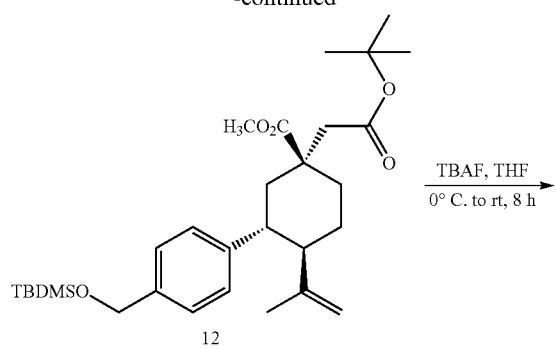

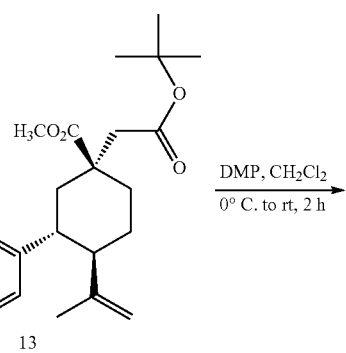

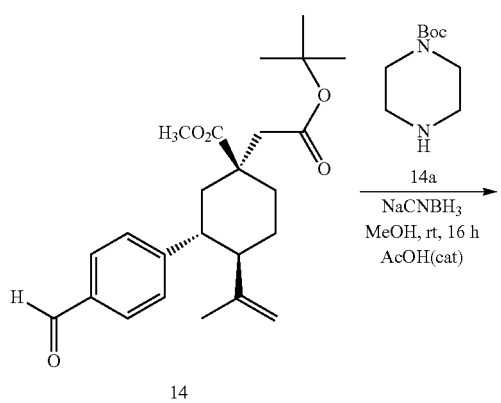

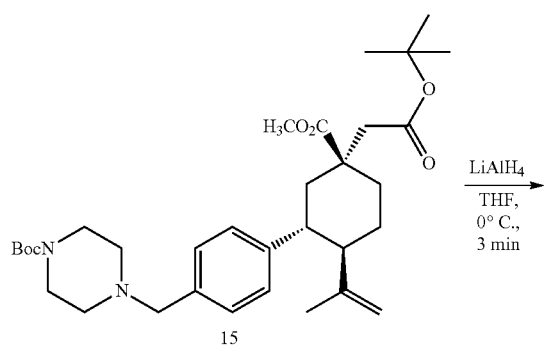

-continued

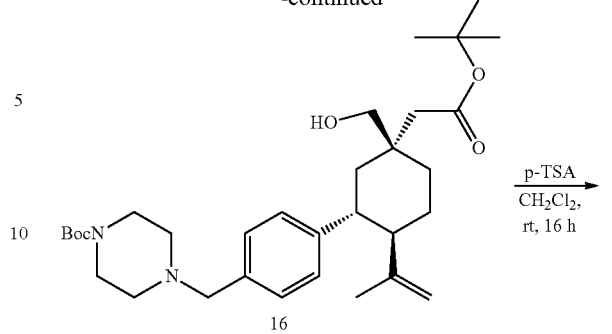

Production of Chemical Compound 2

NaIO$_4$ (626.4 g, 2.94 mol) and RuCl$_3$·nH$_2$O (4.56 g, 22.0 mmol) were added to a solution (0° C.) of (−)-β-pinene (100.0 g, 0.735 mol) dissolved in water (1.50 L), CH$_3$CN (1.0 L) and CH$_2$Cl$_2$ (1.0 L). The reaction mixture was stirred at room temperature for 5 hours. The reaction mixture was diluted with EtOAc (1.0 L) and washed with water (1.0 L) and brine (500 mL). The mixture was dried over anhydrous Na$_2$SO$_4$, filtered, and concentrated under reduced pressure to obtain chemical compound 2 [96.0 g (crude), quantitative] as a brown liquid. $^1$H NMR (400 MHz, CDCl$_3$) δ 2.58-2.51 (m, 3H), 2.38-2.30 (m, 1H), 2.25-2.21 (m, 1H), 2.08-2.01 (m, 1H), 1.98-1.90 (m, 1H), 1.57 (s, 1H), 1.35 (s, 3H), 0.84 (s, 3H).

Production of Chemical Compound 3

A mixture of H$_2$SO$_4$ (25.9 mL, 486.0 mol), SeO$_2$ (91.2 g, 834.0 mol), (PhSe)$_2$ (108.0 g, 347.0 mol) and chemical compound 2 (96.0 g, 695.0 mol) dissolved in methanol (1.0 L) was stirred at room temperature for 5 hours. The reaction mixture was quenched with water (1.0 L) and extracted with EtOAc (1.0 L×2). The organic extract was washed with brine (500 mL), dried over anhydrous Na$_2$SO$_4$, filtered, and concentrated under reduced pressure. The residue was purified by silica gel (60-120 mesh) column chromatography with 5% EtOAc in hexane to obtain chemical compound 3 (80.0 g, 39%) as a greenish brown liquid. $^1$H NMR (400 MHz, CDCl$_3$) δ 7.61-7.58 (m, 2H), 7.32-7.25 (m, 1H), 3.87 (dd, J=1.6 Hz, 8.0 Hz, 1H), 2.71-2.68 (m, 1H), 2.61-2.52 (m, 2H), 2.24-2.20 (m, 2H), 1.88 (s, 1H), 1.35 (s, 3H), 0.84 (m, 3H).

Production of Chemical Compound 4

At 0° C., 7% H$_2$O$_2$ (140.0 mL, 408.0 mol) and pyridine (43.8 mL, 544.0 mol) in that order were added to a solution of chemical compound 3 (80.0 g, 272.0 mol) dissolved in CH$_2$Cl$_2$ (800 mL) and the solution was stirred at room temperature for 12 hours. The reaction mixture was diluted with CH$_2$Cl$_2$ (1.0 L) and washed with water (1.0 L) and brine (500 mL). The obtained mixture was dried over anhydrous Na$_2$SO$_4$, filtered, and concentrated under reduced pressure. The crude product was purified by silica gel (60-120 mesh) column chromatography using 0-5% EtOAc in hexane to obtain chemical compound 4 (30.0 g, 81%) as an oily liquid. $^1$H NMR (400 MHz, CDCl$_3$) δ 7.54-7.50 (m, 1H), 5.95 (d, J=8.8 Hz, 3H), 2.86-2.83 (m, 1H), 2.73-2.57 (m, 2H), 2.13 (s, 1H), 1.51 (s, 3H), 1.04 (m, 3H).

Production of Chemical Compound 5

Chemical compound 4a (chemical compound 1 in scheme 4) (14.5 g, 95.5 mmol) and KOH (8.20 g, 147.0 mmol) were added to a solution of chemical compound 4 (10.0 g, 73.5 mmol) dissolved in water (20.0 mL) and 1,4-dioxane (100 mL), and the solution was degassed for 15 minutes. [Rh(COD)Cl]$_2$ complex (2.17 g, 4.40 mmol) was added to the reaction mixture, stirred, and heated at 80° C. for 12 hours. The residual solvent was evaporated under reduced pressure. The crude product was dissolved in CH$_2$Cl$_2$ (500 mL) and filtered through a celite bed. The filtrate was washed with water (500 mL), dried over anhydrous Na$_2$SO$_4$, filtered, and concentrated under reduced pressure. The residue was purified by combiflash chromatography on silica gel using 0-40% EtOAc in eluent hexane to obtain chemical compound 5 (6.15 g, 34%) as a colorless oil. ESI MS m/z 227 [M-NH$_4$]$^+$.

Production of Chemical Compound 6

Zn(OAc)$_2$ (5.07 g, 27.7 mmol) and BF$_3$·OEt$_2$ (3.42 mL, 27.7 mmol) were added to a solution of chemical compound 5 (6.15 g, 25.0 mmol) dissolved in Ac$_2$O (60 mL) and the solution was stirred at room temperature for 12 hours. The reaction mixture was neutralized with saturated NaHCO$_3$ (500 mL). The obtained mixture was extracted with EtOAc (2×250 mL). The organic layer was mixed, washed with brine (250 mL), dried over anhydrous MgSO$_4$ and concentrated under reduced pressure to obtain the residual oil. It was purified by combiflash chromatography on silica gel using 0-30% EtOAc in eluent hexane to obtain chemical compound 6 (5.00 g, 69%) as an off-white solid. ESI MS m/z 269 [M-NH$_4$]$^+$.

Production of Chemical Compound 7

At 0° C., NaH (0.70 g, 60% in mineral oil, 17.4 mmol) was gradually added to a solution of chemical compound 6 (5.00 g, 17.4 mmol) dissolved in methanol (50 mL) over 30 minutes. The reaction mixture was stirred at room temperature for 30 minutes. The reaction mixture was quenched with saturated NH$_4$Cl solution (25 mL) at 0° C. The methanol in the mixture was evaporated under reduced pressure. The residual suspension was filtered and washed with water (100 mL) and then hexane (100 mL) to obtain chemical compound 7 (4.50 g, crude) as an off-white solid. ESI MS m/z 227 [M-NH$_4$]$^+$.

Production of Chemical Compound 8

Chemical compound 7 (1.00 g, 4.00 mmol) dissolved in THF (15.0 mL) was added to an ice-cold solution of t-BuOK (1.83 g, 16.3 mmol) and p-toluenesulfonylmethylisocyanide (1.59 g, 8.2 mmol) dissolved in THF (15 mL), and the solution was stirred at 0° C. for 10 minutes. Methanol (25 mL) was added thereto. The obtained mixture was stirred under reflux for 1 hour and concentrated under reduced pressure. The residue was purified by combiflash chromatography on silica gel using 0-50% EtOAc in eluent hexane to obtain chemical compound 8 (0.80 g, 77%) as a pale yellow liquid. This step was performed multiple times to obtain chemical compound 8 at 77%.

Production of Chemical Compound 9

At room temperature, KOH (8.70 g, 156.0 mmol) was added to a solution of chemical compound 8 (4.00 g, 15.0 mmol) dissolved in 2-propanol (40 mL). The reaction mixture was heated to 100° C. and stirred under reflux for 48 hours. The residual solvent was evaporated under reduced pressure. The crude product was dissolved in EtOAc (100 mL) and washed with water (50 mL). The aqueous layer was neutralized with 2N HCl solution and extracted with EtOAc (2×100 mL). The organic layer was mixed, washed with brine (50 mL), dried over MgSO$_4$ and concentrated under reduced pressure to obtain chemical compound 9 (2.50 g, crude) as a brown viscous material. ESI MS m/z 273 [M−H]$^+$.

Production of Chemical Compound 10

At 0° C., K$_2$CO$_3$ (3.80 g, 27.3 mmol) and MeI (3.84 mL, 27.3 mmol) were dropped to a solution of chemical compound 9 (2.50 g, 9.12 mmol) dissolved in acetonitrile:methanol (15:5 mL). The reaction mixture was heated to room temperature and stirred for 16 hours. The reaction mixture was diluted with water (100 mL) and extracted with EtOAc (2×50 mL). The organic layer was mixed, washed with brine (50 mL), dried over MgSO$_4$ and concentrated under reduced pressure. The residue was purified by combiflash chromatography on silica gel using 0-30% EtOAc in eluent hexane to obtain chemical compound 10 (1.25 g, 48%) as an oily viscous material. ESI MS m/z 271 [M-NH$_4$]$^+$.

Production of Chemical Compound 11

At 0° C., imidazole (0.63 g, 10.8 mmol) and TBDMSCl (0.78 g, 5.20 mmol) in that order were gradually added to a stirred solution of chemical compound 10 (1.25 g, 4.30 mol) dissolved in CH$_2$Cl$_2$ (15 mL). The reaction mixture was stirred at room temperature for 16 hours, diluted with CH$_2$Cl$_2$ (100 mL), and washed with saturated NaHCO$_3$ solution (50 mL). The obtained reaction mixture was dried over anhydrous Na$_2$SO$_4$ and concentrated under reduced pressure. The residue was purified by combiflash chromatography on silica gel using 0-10% EtOAc in eluent hexane to obtain chemical compound 11 (1.25 g, 72%) as a pale yellow oil.

Production of Chemical Compound 12

At −78° C., chemical compound 11 (1.55 g, 3.80 mmol) was dropped to a solution of lithium diisopropylamide (5.78 mL, 2.0 M in THF, 11.5 mmol) dissolved in THF (8.0 mL). The solution was stirred at −78° C. for 30 minutes, and tert-butyl 2-bromoacetate (1.60 mL, 7.70 mmol) was added to the reaction mixture. The reaction mixture was stirred at −78° C. for 30 minutes and quenched with saturated NH$_4$Cl solution (15 mL). The obtained mixture was extracted with EtOAc (2×50 mL). The organic layer was mixed, washed with brine (25 mL), dried over anhydrous Na$_2$SO$_4$ and concentrated under reduced pressure. The residue was purified by combiflash chromatography on silica gel using 0-10% EtOAc in eluent hexane to obtain chemical compound 12 (2.1 g, crude) as a pale yellow oil.

Production of Chemical Compound 13

At 0° C., TBAF (8.10 mL, 1 M in THF, 8.13 mmol) was added to an ice-cold solution of chemical compound 12 (2.10 g, 4.06 mmol) dissolved in THF (20 mL). The reaction mixture was stirred at room temperature for 8 hours and diluted with water (50 mL). The obtained mixture was extracted with EtOAc (2×50 mL). The organic layer was mixed, washed with brine (25 mL), dried over MgSO$_4$ and concentrated under reduced pressure to obtain the residual oil. It was purified by combiflash chromatography on silica gel using 0-30% EtOAc in eluent hexane to obtain chemical compound 13 (1.48 g, 90%) as a colorless viscous material.

Production of Chemical Compound 14

At 0° C., Dess-Martin periodinane (3.12 g, 7.36 mmol) was added to an ice-cold solution of chemical compound 13 (1.48 g, 3.60 mmol) dissolved in CH$_2$Cl$_2$ (15 mL). The reaction mixture was stirred at room temperature for 2 hours.

The reaction mixture was quenched with saturated $Na_2S_2O_3$ solution (20 mL) and saturated $NaHCO_3$ solution (20 mL) at 0° C., filtered through a celite bed and extracted with $CH_2Cl_2$ (2×50 mL). The organic layer was mixed, washed with brine (50 mL), dried over $MgSO_4$ and concentrated under reduced pressure to obtain chemical compound 14 [1.50 g (crude)] as a colorless oil. ESI MS m/z 401 [M+H]$^+$.
Production of Chemical Compound 15

At room temperature, chemical compound 14a (1.39 g, 7.50 mmol) and $NaCNBH_3$ (0.71 g, 11.20 mmol) in that order were added to a solution of chemical compound 14 (1.50 g, 3.75 mmol) dissolved in methanol (5.0 mL) and a small amount of AcOH (0.06 ml, 1.10 mmol). The reaction mixture was stirred at room temperature for 16 hours. The methanol in the mixture was evaporated and diluted with water (50 mL). The obtained mixture was extracted with EtOAc (2×50 mL). The organic layer was mixed, washed with brine (25 mL), dried over $MgSO_4$ and concentrated under reduced pressure. The residue was purified by combiflash chromatography on silica gel using 0-40% EtOAc in eluent hexane to obtain chemical compound 15 (1.60 g, 75%) as a colorless viscous material. ESI MS m/z 571 [M+H]$^+$.
Production of Chemical Compound 16

At 0° C., $LiAlH_4$ (2.0 M in THF, 0.87 mL, 1.70 mmol) was added to an ice-cold solution of chemical compound 15 (0.10 g, 0.17 mmol) dissolved in THF (10.0 mL). The reaction mixture was stirred at 0° C. for 3 minutes and quenched with saturated $NH_4Cl$ solution (5.0 mL). The obtained mixture was extracted with EtOAc (2×10 mL). The organic layer was mixed, washed with brine (5 mL), dried over $MgSO_4$ and concentrated under reduced pressure. The residue was purified by combiflash chromatography on silica gel using 0-60% EtOAc in eluent hexane to obtain chemical compound 16 (0.034 g) as a colorless oil. These steps were performed multiple times to obtain chemical compound 16 at 36%. ESI MS m/z 543 [M+H]$^+$.
Production of Chemical Compound B2-24-4-5A·HCOOH At room temperature, p-toluenesulfonic acid (0.74 g, 3.90 mmol) was added to chemical compound 16 (0.53 g, 0.97 mmol) dissolved in $CH_2Cl_2$ (10.0 mL). The reaction mixture was quenched with saturated $NaHCO_3$ solution (10 mL) and extracted with $CH_2Cl_2$ (2×25 mL). The organic layer was mixed, washed with brine (25 mL), dried over $MgSO_4$ and concentrated. The residue was purified by mass-triggered preparative HPLC to obtain chemical compound B2-24-4-5A·HCOOH (0.208 g, 51%) as an off-white solid. $^1$H NMR (400 MHz, $CDCl_3$) δ 8.46 (s, 1H), 7.18 (d, J 8.0 Hz, 2H), 7.06 (d, J=8.0 Hz, 2H), 4.55 (s, 2H), 4.28 (s, 2H), 3.49 (s, 2H), 3.09-3.03 (m, 4H), 2.60-2.50 (m, 5H), 2.39-2.25 (m, 3H), 1.92-1.88 (m, 2H), 1.82-1.78 (m, 1H), 1.68-1.52 (m, 3H) 1.46 (s, 3H). ESI MS m/z 369 [M+H]$^+$.
Production of Chemical Compound B2-24-4-5A Chemical compound B2-24-4-5A·HCOOH (100 mg) dissolved in water (5 mL) was extracted with 10% methanol (10 mL×8) dissolved in $CH_2Cl_2$. The organic layer was mixed, dried over anhydrous $MgSO_4$, filtered, and concentrated under reduced pressure to obtain chemical compound B2-24-4-5A (45 mg). $^1$H NMR (400 MHz, $CDCl_3$) δ 7.19 (d, J 8.0 Hz, 2H), 7.04 (d, J=8.0 Hz, 2H), 4.55 (s, 2H), 4.28 (s, 2H), 3.45 (s, 2H), 2.94 (t, 4H), 2.57-2.42 (m, 5H), 2.35-2.25 (m, 3H), 1.92-1.75 (m, 3H), 1.68-1.52 (m, 4H) 1.48 (s, 3H). ESI MS m/z 369 [M+H]$^+$.

Example 5: Evaluation of TLR7 Activation Inhibition in B2-24-4-5A·HCOOH

The evaluation of the TLR7 activation inhibition by B2-24-4-5A·HCOOH was performed by the method described in Example 2. CB-7 and B2-24-4·HCl were used as controls. $IC_{50}$ of CB-7 and each derivative are shown in Table 5.

TABLE 5

|  | $IC_{50}$ (μM) |
|---|---|
| CB-7 | 7.6600 |
| B2-24-4·HCl | 0.1669 |
| B2-24-4-5A·HCOOH | 0.1673 |

As shown in Table 5, B2-24-4-5A·HCOOH and B2-24-4·HCl were almost equivalent in terms of mouse TLR7 inhibition.

Example 6: Confirmation of TLR7 Inhibitory Effect of B2-24-4-5A·HCOOH on Mouse Bone Marrow-Derived Macrophages (BMDM)

Figure 2:
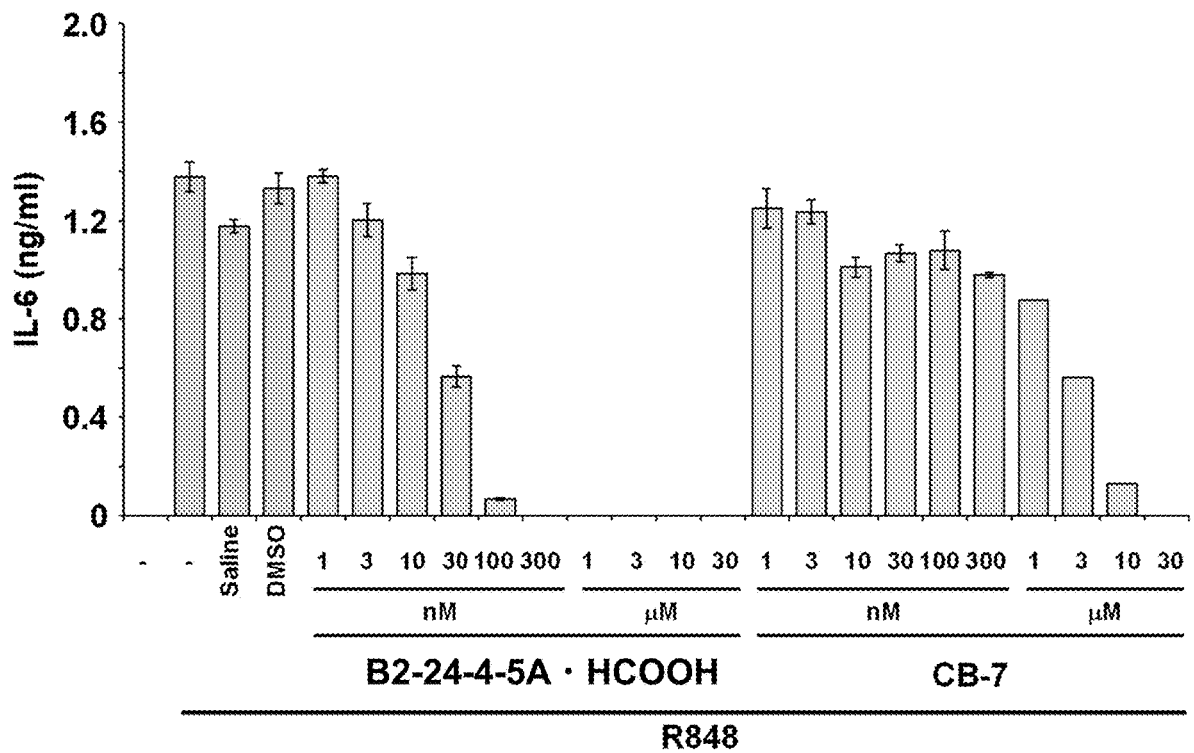
FIG. 2 shows the TLR7 inhibitory activity (suppression of IL-6 expression) of CB-7 or B2-24-4-5A·HCOOH in mouse bone marrow-derived macrophages (BMDM).

The inhibitory effect of B2-24-4-5A·HCOOH on TLR7 in mouse BMDM was studied. Mouse bone marrow cells were cultured in RPMI 1640 medium containing 10 μg/ml M-CSF, 10% (v/v) fetal calf serum (FCS), penicillin, streptomycin, L-glutamic acid, and 2-mercaptoethanol in the presence of 5% (v/v) $CO_2$ for 7 days at 37° C. Mouse BMDMs induced to differentiate by culture were spread into each well of a 96-well plate at $1.0×10^5/100$ μL. 50 μL of CB-7 or B2-24-4-5A·HCOOH was added to each well and incubated for 30 minutes. B2-24-4-5A·HCOOH and CB-7 were 10 mg/mL saline and DMSO solution, respectively. Next, the TLR7 ligand, R848 (Invivogen), was added thereto at a final concentration of 10 ng/mL and incubated for 24 hours. After incubation, all culture media were collected and the concentration of IL-6 in each culture medium was quantified using ELISA (used kit: Mouse IL-6 DuoSet ELISA (trade name), manufactured by R&D Systems). The results are shown in FIG. 2.

IL-6 production induced by R848 stimulation was attenuated by pretreatment with B2-24-4-5A·HCOOH. TLR7 inhibitory activity of B2-24-4-5A·HCOOH was about 100-fold stronger than that of CB-7.

Example 7: Confirmation of TLR7 Selectivity of B2-24-4-5A·HCOOH in Mouse BMDM

Figure 3:
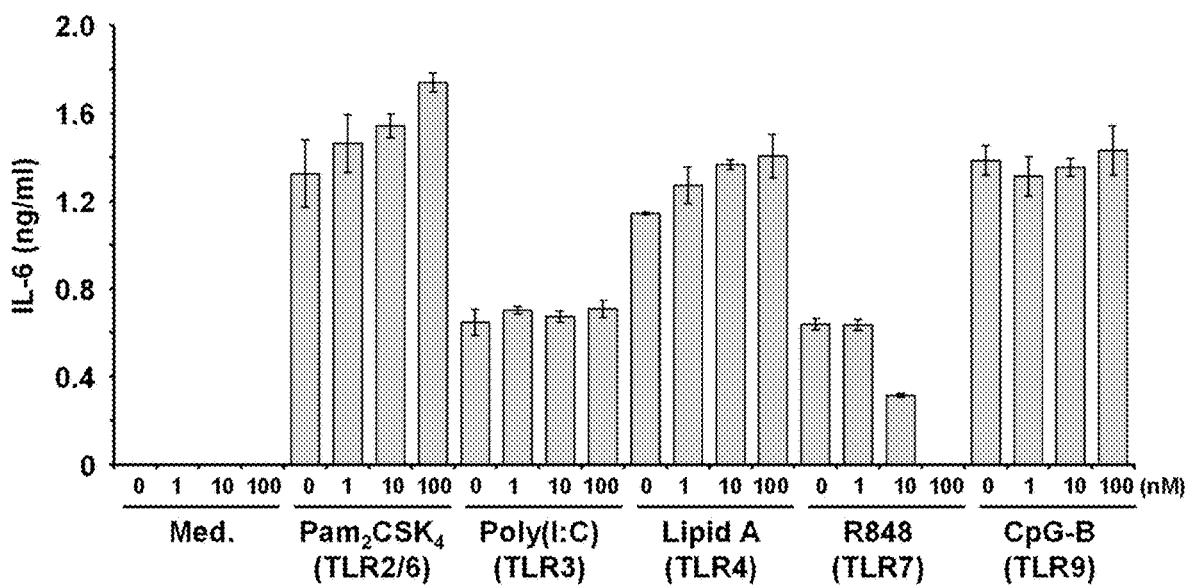
FIG. 3 shows that B2-24-4-5A·HCOOH in mouse BMDM is TLR7 selective.

The TLR7 selectivity of B2-24-4-5A·HCOOH in mouse BMDM was studied. Mouse bone marrow cells were cultured in RPMI 1640 medium containing 10 μg/ml M-CSF, 10% (v/v) fetal calf serum (FCS), penicillin, streptomycin, L-glutamic acid, and 2-mercaptoethanol in the presence of 5% (v/v) $CO_2$ for 7 days at 37° C. Mouse BMDMs induced to differentiate by culture were spread into each well of a 96-well plate at $1.0×10^5/100$ μL. 50 μL of B2-24-4-5A·HCOOH was added to each well to achieve a final concentration of 1 nM, 10 nM or 100 nM and incubated for 30 minutes. The TLR ligands Pam2CSK4 (Invivogen), Poly (I:C) (Invivogen), Lipid A (Sigma-Aldrich), R848 (Invivogen) or CpG-B (Invivogen) were added to each well for 24 hours. Cultures were incubated for 24 hours. After incubation, all culture media were collected and the concentration of IL-6 in the culture medium was quantified using ELISA (used kit: Mouse IL-6 DuoSet ELISA (trade name), manufactured by R&D Systems). The results are shown in FIG. 3.

B2-24-4-5A·HCOOH inhibited the production of IL-6 by stimulation of the TLR7 ligand R848, but not by stimulation of other TLR ligands. Thus, B2-24-4-5A·HCOOH was shown to be a selective inhibitor of TLR7.

Figure 4:
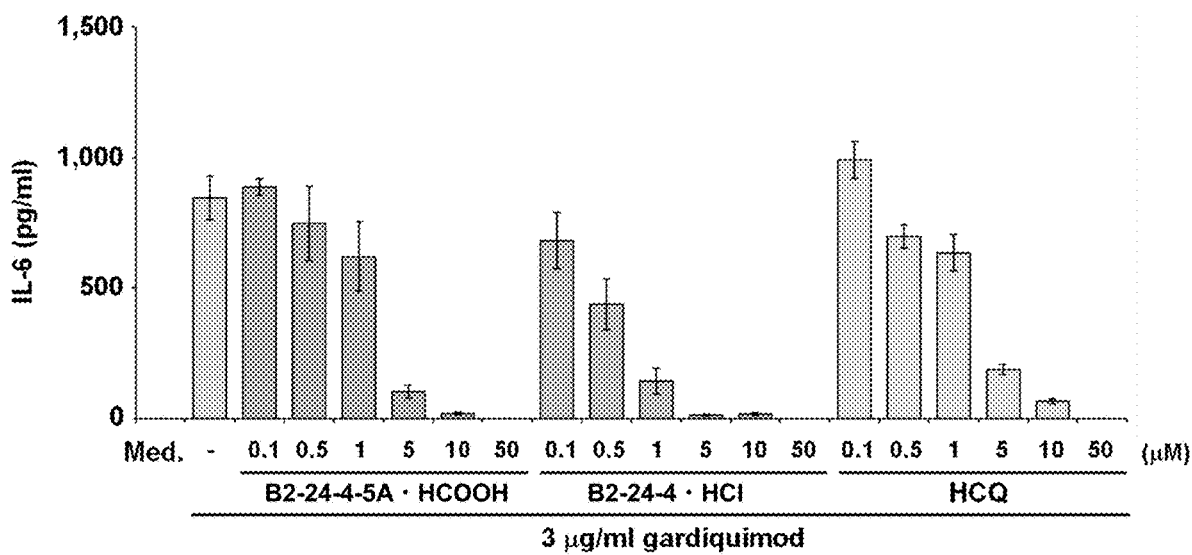
FIG. 4 shows the TLR7 inhibitory activity (suppression of IL-6 expression) of B2-24-4-5A·HCOOH, B2-24-4·HCl, or hydroxychloroquine sulfate (HCQ) in peripheral blood mononuclear cells (PBMCs) from patients with systemic lupus erythematosus.

Example 8: Confirmation of TLR7 Inhibitory Effect of B2-24-4-5A·HCOOH Using Peripheral Blood Mononuclear Cells (PBMCs) Derived from Patients with Systemic Lupus Erythematosus The TLR7 inhibitory effect of B2-24-4-5A·HCOOH on PBMCs derived from patients with systemic lupus erythematosus was studied. PBMCs were isolated from 7 mL of blood collected from patients with systemic lupus erythematosus. Isolated PBMCs were spread into each well of a 96-well plate containing RPMI 1640 medium containing 10% (v/v) fetal calf serum (FCS), penicillin, streptomycin, L-glutamic acid, and 2-mercaptoethanol at $0.5\times10^5/100$ μL and incubated at 37° C. in the presence of 5% (v/v) $CO_2$. 50 μL of B2-24-4-5A·HCOOH, B2-24-4·HCl or the comparative drug hydroxychloroquine sulfate (HCQ) was added to each well to achieve a final concentration of 0.1 μM, 0.5 μM, 1 μM, 5 μM, 10 μM or 50 μM and incubated for 30 minutes. The TLR7 ligand, Gardiquimod (Invivogen), was added at a final concentration of 3 μg/mL and incubated for 24 hours. After incubation, all culture media were collected and the concentration of IL-6 in the culture medium was quantified using ELISA (used kit: human IL-6 DuoSet ELISA (trade name), manufactured by R&D Systems). The results are shown in FIG. 4.

IL-6 production induced by gardiquimod stimulation was attenuated by pretreatment with all chemical compounds, and the effect was stronger for B2-24-4·HCl, B2-24-4-5A·HCOOH, and HCQ, in that order.

Example 9: Analysis of Metabolic Stability (CYP) of CB-7 and B2-24-4-5A·HCOOH Using Mouse Liver Microsomes Metabolic stability analysis of CB-7 and B2-24-4-5A·HCOOH was performed by the method of Example 5. The results for CB-7 are shown in Table 6 and the results for B2-24-4-5A·HCOOH are shown in Table 7.

The number of peaks detected by HPLC in CB-7 was 9 (Table 6 shows 7 peaks of the 9 peaks). On the other hand, the number of peaks detected by HPLC in B2-24-4-5A·HCOOH was 6, which was fewer than CB-7. The peak area (Area) of CB-7 after 2 hours was 41.6%, while the peak area (Area) of B2-24-4-5A·HCOOH after 2 hours was 88.4%. Thus, B2-24-4-5A·HCOOH significantly improved drug metabolism, mainly by CYPs, compared to CB-7.

Figure 5:
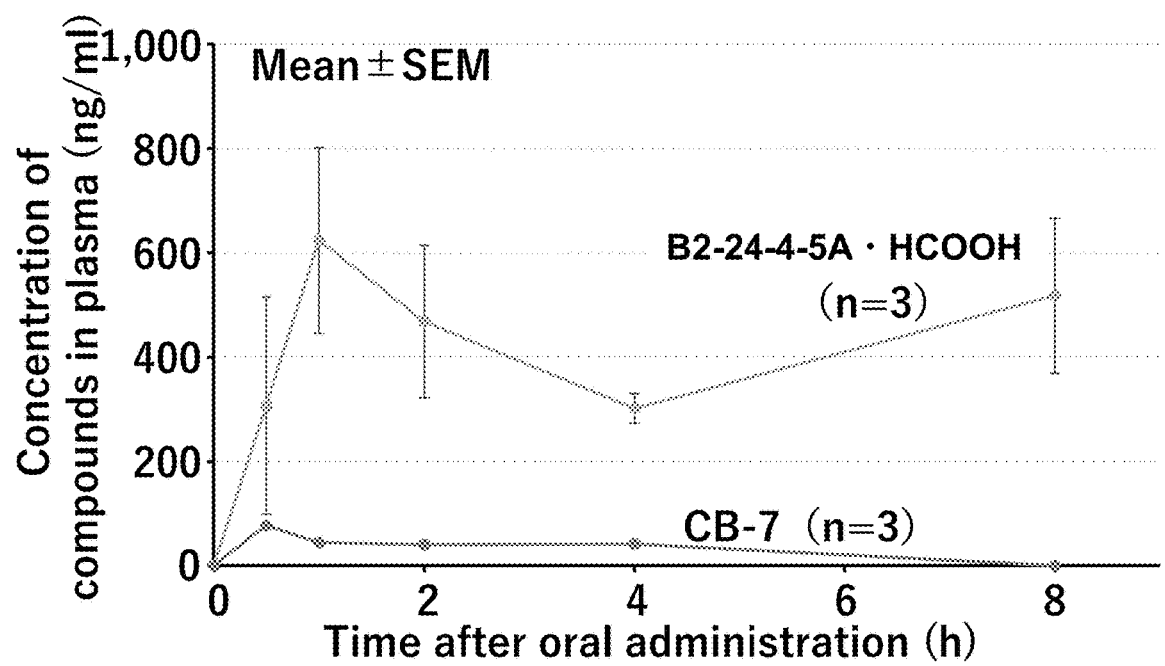
FIG. 5 shows the plasma concentration of CB-7 or B2-24-4-5A·HCOOH in mice after oral administration.

Example 10: Plasma Levels of CB-7 or B2-24-4-5A·HCOOH in Mice after Oral Administration Plasma concentrations of CB-7 or B2-24-4-5A·HCOOH were measured in normal mice (C57BL/6N, 11 weeks old, female) after oral administration. 1 mg of CB-7 or B2-24-4-5A·HCOOH was administered orally to mice C57BL/6N. After 0.5, 1, 2, 4, or 8 hours, blood was collected from mice C57BL/6N to prepare plasma. The concentration of CB-7 or B2-24-4-5A·HCOOH in the plasma was measured by LC/MS/MS. The results are shown in FIG. 5.

CB-7 could not be detected in plasma after 8 hours, while B2-24-4-5A·HCOOH was present in plasma at about 500 ng/ml after 8 hours, indicating that B2-24-4-5A·HCOOH remains in plasma for a longer time than CB-7.

Figure 6:
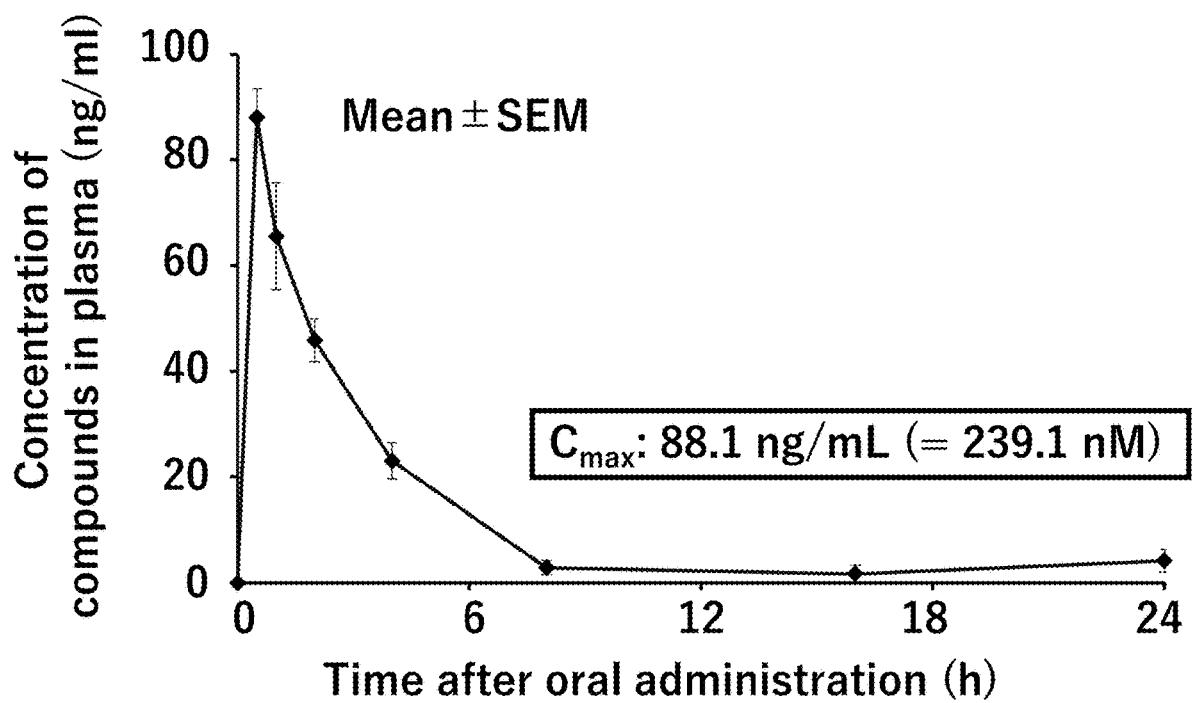
FIG. 6 shows the plasma concentration of B2-24-4-5A·HCOOH in a mouse model of systemic lupus erythematosus after oral administration.

Example 11: Plasma Concentration of B2-24-4-5A·HCOOH in Mice after Oral Administration Plasma concentrations of B2-24-4-5A·HCOOH were determined after oral administration of B2-24-4-5A·HCOOH in a mouse model of systemic lupus erythematosus (NZBWF1, 20 weeks old, female). 5 mg/kg of B2-24-4-5A·HCOOH was administered orally to NZBWF1 mice. After 0.5, 1, 2, 4, 8, 16, or 24 hours, blood was collected from NZBWF1 mice to prepare plasma. The concentration of B2-24-4-5A·HCOOH in the plasma was determined by LC/MS/MS. The results are shown in FIG. 6.

B2-24-4-5A·HCOOH was present in plasma at 0.5 hours at 88.1 ng/ml. After that, it disappeared, reaching a near-bottom level after 8 hours.

TABLE 6

| Peak name | | C-P3 | C-P4 | C-P5 | C-P6 | C-P7 | C-P8 | C-P9 | CB-7 | Total |
|---|---|---|---|---|---|---|---|---|---|---|
| RT (min) | | 5.5 | 5.7 | 6.4 | 6.6 | 7.3 | 7.4 | 7.9 | 8.6 | 100 |
| Area (%) | 2.0 h | 3.8 | 4.8 | 6.2 | 4.5 | 7.0 | 15.4 | 17.1 | 41.2 | 100 |
| | 0.5 h | 1.5 | 1.7 | 3.6 | 3.5 | 4.6 | 10.6 | 9.3 | 65.3 | 100 |
| | 0 h | N.D. | N.D. | N.D. | N.D. | N.D. | N.D. | N.D. | 100 | 100 |

N.D.: undetectable by LC-UV (220 nm)

TABLE 7

| Peak name | | 5A-P1 | 5A-P2 | 5A-P3 | 5A-P4 | 5A-P5 | 5A-P6 | B2-24-4-5A ·HCOOH | Total |
|---|---|---|---|---|---|---|---|---|---|
| RT (min) | | 7.9 | 8.2 | 8.5 | 11.6 | 11.8 | 14.3 | 12.3 | 100 |
| Area (%) | 2.0 h | 0.7 | 0.7 | 9.6 | N.D. | N.D. | 0.6 | 88.4 | 100 |
| | 0.5 h | 0.3 | 0.3 | 3.8 | N.D. | N.D. | 0.2 | 95.4 | 100 |
| | 0 h | N.D. | N.D. | N.D. | N.D. | N.D. | N.D. | 100 | 100 |

N.D.: undetectable by LC-UV (220 nm)

Figure 7:
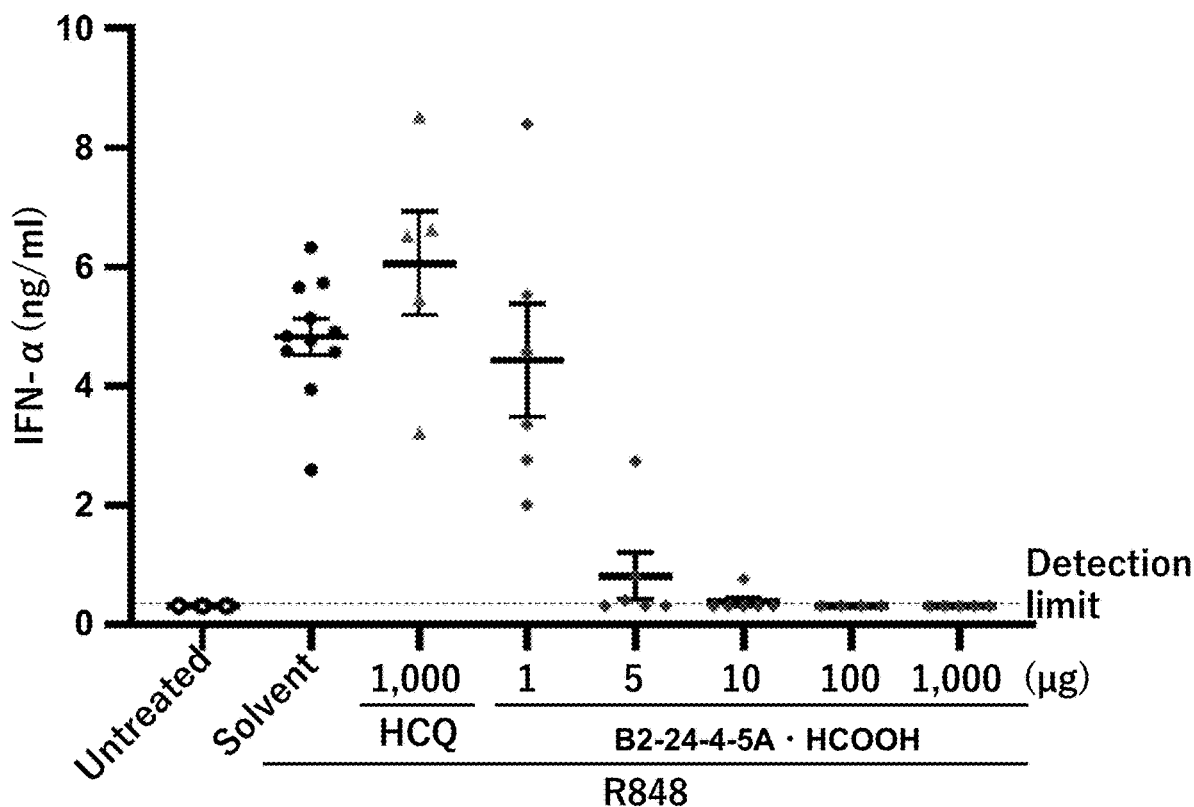
FIG. 7 shows the TLR7 inhibitory activity (suppression of IFN-α expression) by intraperitoneal administration of B2-24-4-5A·HCOOH or HCQ in mice.

Example 12: Confirmation of TLR7 Inhibition Effect by Intraperitoneal Administration of B2-24-4-5A·HCOOH in Mice Normal mice (C57BL/6N, 11 weeks old, female) were administered B2-24-4-5A·HCOOH (1, 5, 10, 100 and 1000 μg) or hydroxychloroquine sulfate (HCQ, 1000 μg) as a comparison drug intraperitoneally, followed by 5 μg of R848 after 30 minutes. The solvent was saline solution. 1 hour after R848 administration, blood was collected and the concentration of IFN-α in the serum was quantified using ELISA (used kit: Mouse IFN alpha Platinum ELISA (trade name), eBioscience). The results are shown in FIG. 7. The plots in FIG. 7 represent the data for each individual, each bold line represents the mean value of each group data, and each error bar represents the standard error of each group data.

IFN-αproduction induced by R848 was attenuated by pretreatment with B2-24-4-5A·HCOOH, and the effect was stronger than that of HCQ. 10 μg of B2-24-4-5A·HCOOH administered peritoneally had an almost complete inhibitory effect on IFN-α induction. This result indicates that it has drug efficacy at 0.5 mg/kg, assuming that the mice weighed 20 g. In other words, the TLR7 inhibitory effect of B2-24-4-5A·HCOOH in vivo was more than 100 times greater than that of HCQ.

Figure 8:
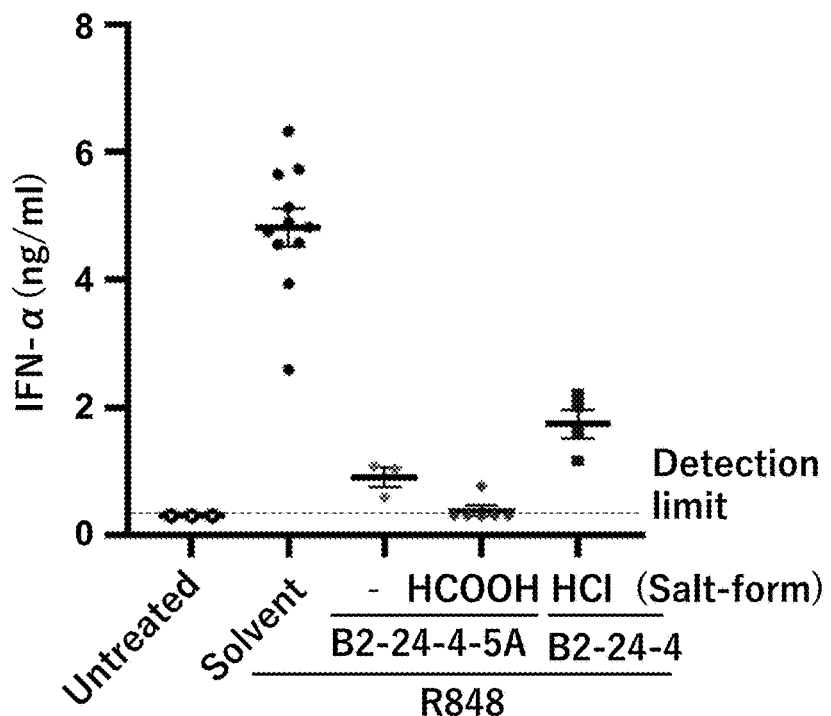
FIG. 8 shows the TLR7 inhibitory activity (suppression of IFN-α expression) by intraperitoneal administration of B2-24-4·HCl, B2-24-4-5A, B2-24-4-5A·HCOOH or HCQ in mice.

Example 13: Confirmation of TLR7 Inhibition Effect by Intraperitoneal Administration of B2-24-4·HCl, B2-24-4-5A or B2-24-4-5A·HCOOH in Mice The same method as in Example 13 was used to study the TLR7 inhibition effect of intraperitoneal administration of B2-24-4·HCl, B2-24-4-5A or B2-24-4-5A·HCOOH in mice. B2-24-4·HCl, B2-24-4-5A and B2-24-4-5A·HCOOH were administered at a dose of 10 μg. The results are shown in FIG. 8. The plots in FIG. 8 represent the data for each individual, each bold line represents the mean of each group data, and each error bar represents the standard error of each group data.

IFN-αproduction induced by R848 was attenuated by pretreatment with B2-24-4·HCl, B2-24-4-5A or B2-24-4-5A·HCOOH, and the effect was stronger with B2-24-4-5A·HCOOH, B2-24-4-5A and B2-24-4·HCl in that order.

Example 14: Confirmation of Therapeutic Effect of B2-24-4-5A·HCOOH in Mouse Model of Drug-Induced Systemic Lupus Erythematosus Systemic lupus erythematosus-like condition was induced in normal mice (BALB/c, 7 weeks old, female, n=10) by applying Beselna cream (trade name) to the right ear three times a week for 8 weeks. These mice were then divided into a saline-administered group (control, n=5) and a B2-24-4-5A·HCOOH-administered group (n=5). The saline-administered group was orally administered saline (100 l) once a day, every day, while continuing the same application of Beselna cream. The B2-24-4-5A·HCOOH-administered group received 5 mg/kg of B2-24-4-5A·HCOOH (100 l) orally once a day, every day, while continuing the same application of Beselna cream. Six weeks after the start of administration, mice were euthanized. After euthanasia, blood was drawn from the abdominal aorta of the mice, and the spleen and kidneys were removed. The removed spleens were photographed and weighed.

The removed spleen was polished on a glass slide to prepare splenocytes and stained with FITC-conjugated anti-CD3 and PE-conjugated anti-CD69 antibodies. 20 minutes later, the cells were washed with FACS buffer and suspended in 200 μL of FACS buffer containing 25 μg/mL 7-actinomycin D, respectively. The cells were then washed with FACS buffer. The fluorescence intensity of the cells was analyzed by flow cytometry. Flow cytometry measurements were performed on a FACSCanto™ II (Becton Dickinson) and data were analyzed with FlowJo software (Tree Star) to calculate the percentage of CD69 positive cells (activated T cells) to CD3 positive T cells.

The removed kidneys were fixed with 4% (w/v) paraformaldehyde, and immunohistochemical staining was entrusted to Morpho Technology, Inc. Blood collected from the abdominal aorta was centrifuged and serum was prepared. Determination of urea nitrogen and creatinine levels in the serum was entrusted to Oriental Yeast Co. The results are shown in FIGS. 9a to 9d.

Figure 9A:
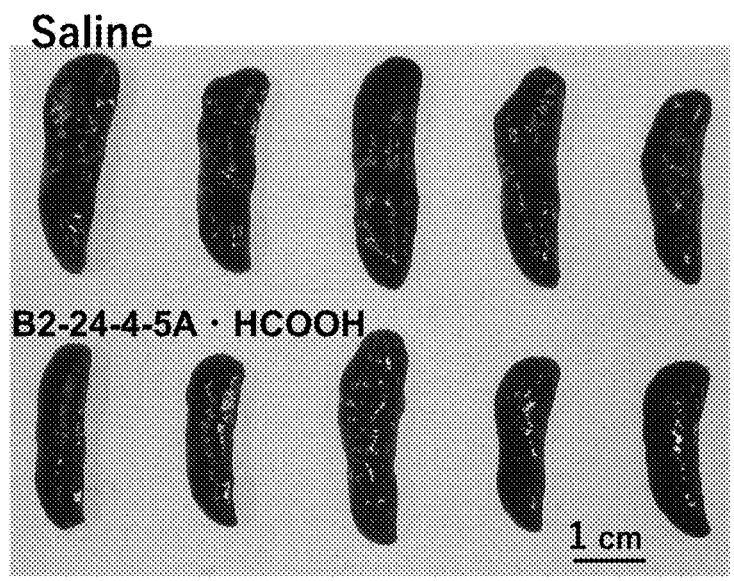
FIG. 9A shows a photograph of the spleen of mice in which a systemic lupus erythematosus-like pathology was induced (saline-administered and B2-24-4-5A·HCOOH-administered groups).
Figure 9B:
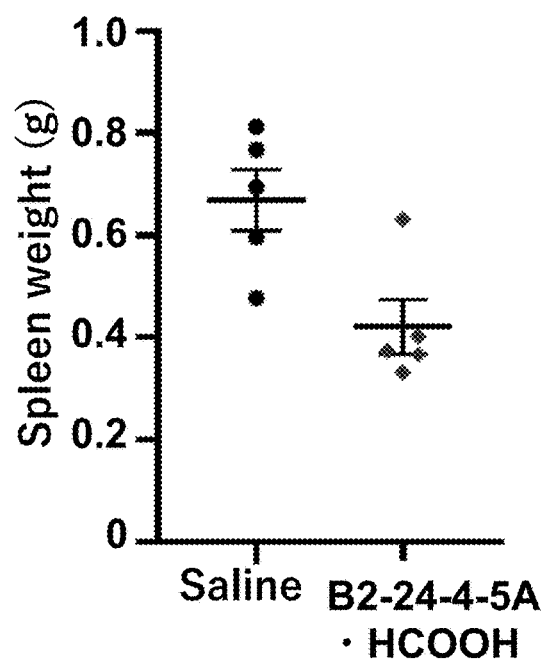
FIG. 9B shows the spleen weights of mice induced with systemic lupus erythematosus-like pathology (saline-administered and B2-24-4-5A·HCOOH-administered groups).
Figure 9C:
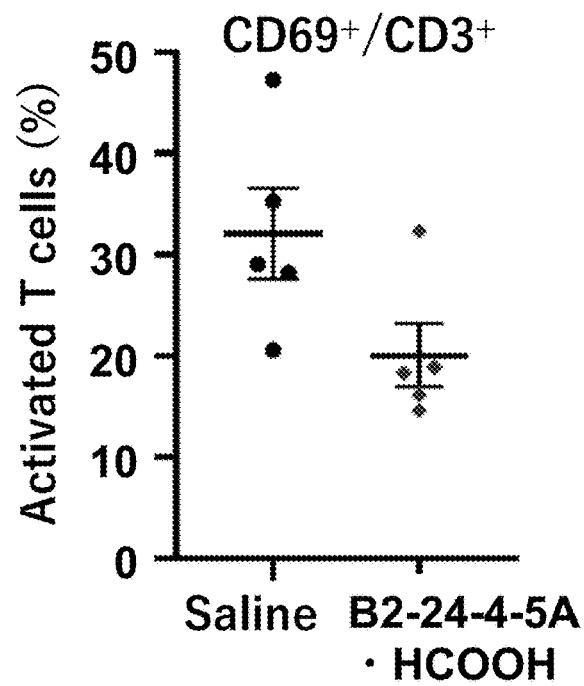
FIG. 9C shows the percentage of activated T cells in the spleen of mice induced with systemic lupus erythematosus-like pathology (saline-administered and B2-24-4-5A·HCOOH-administered groups).
Figure 9D:
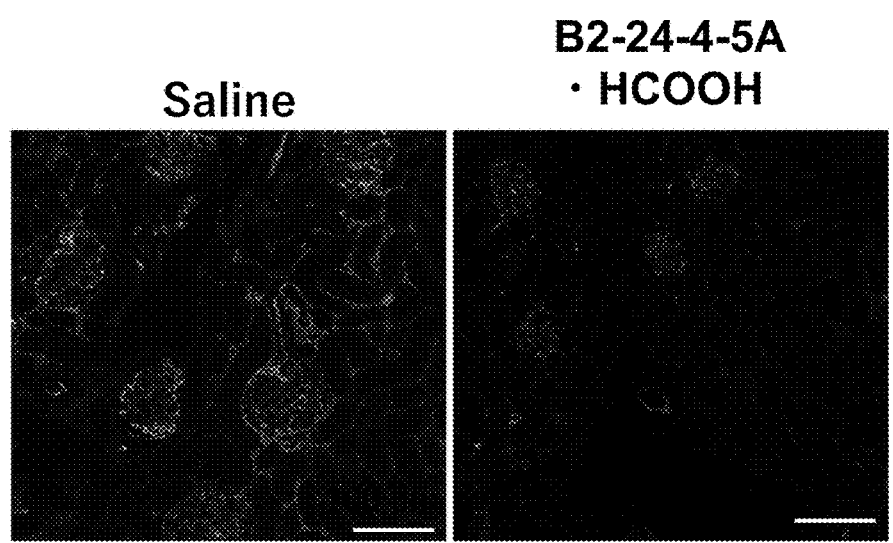
FIG. 9D shows photographs of the deposition of IgG in the glomeruli of mice induced systemic lupus erythematosus-like pathology (saline-administered and B2-24-4-5A·HCOOH-administered groups).

FIG. 9A shows a photograph of the removed spleen. FIG. 9B shows spleen weight. FIG. 9C shows the percentage of activated T cells in splenic T cells. FIG. 9D is a photograph showing IgG deposition in glomeruli. The plots in FIGS. 9B and 9C show the data for each individual, each bold line represents the mean of each group data, and each error bar represents the standard error of each group data. The scale bar in FIG. 9D represents 100 m.

As shown in FIGS. 9A to 9D, the B2-24-4-5A·HCOOH-administered group showed suppression of splenomegaly, less percentage of activated T cells in splenic T cells, and suppression of IgG deposition in glomeruli than the control saline-administered group.

Example 15: Synthesis of Formate of Chemical Compound B2-24-4

We commissioned Albany Molecular Research Inc. (USA) to prepare chemical compound B2-24-4·HCOOH. The structure of B2-24-4·HCOOH is represented by the following formula (XV).

[Chemical 75]

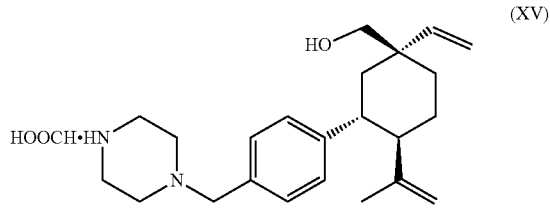

(XV)

Synthesis Example 27

Synthesis of Chemical Compound B2-24-4·HCOOH

A method for the production of chemical compound B2-24-4·HCOOH (also called ALB-210796) is as follows (also called scheme 28).

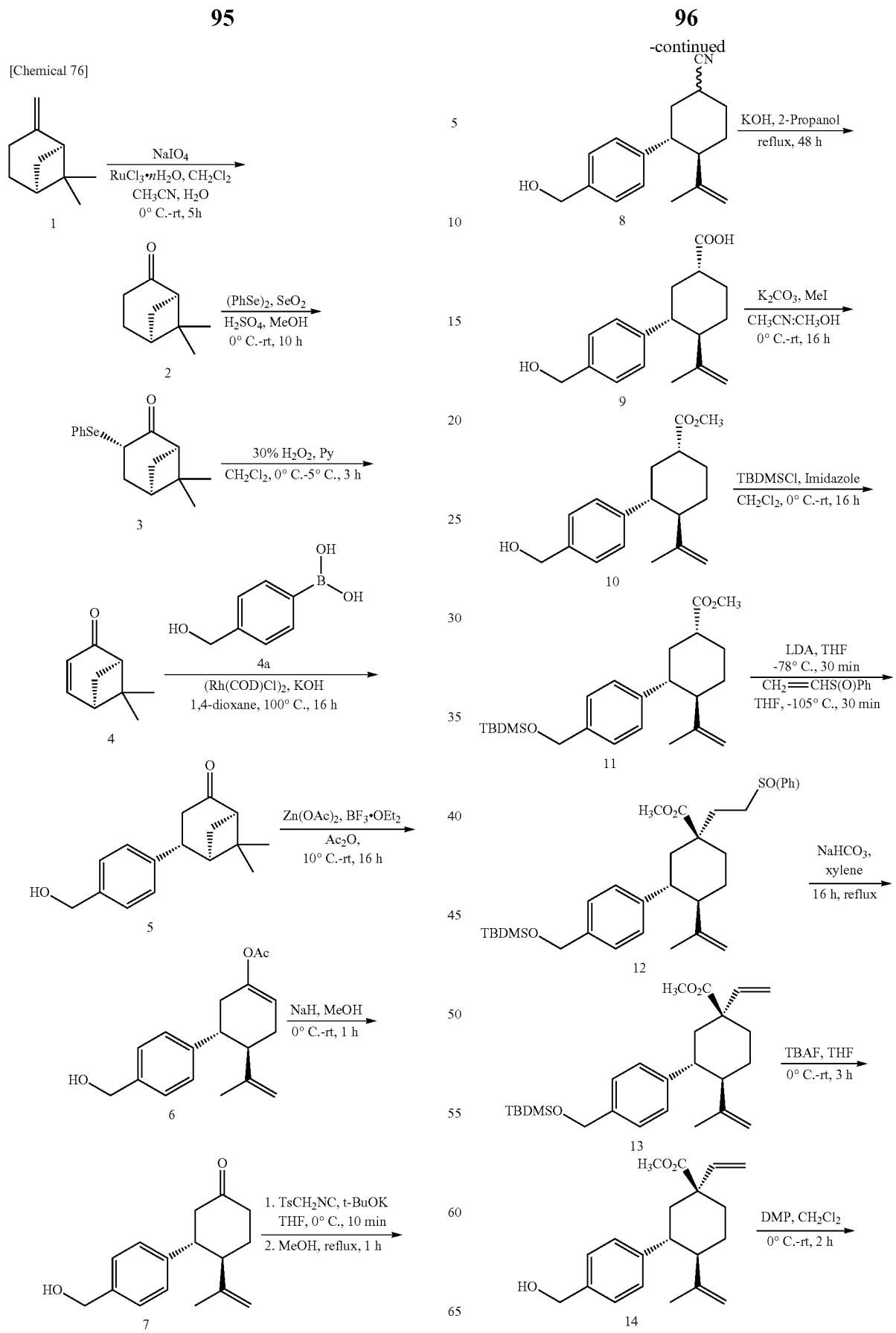

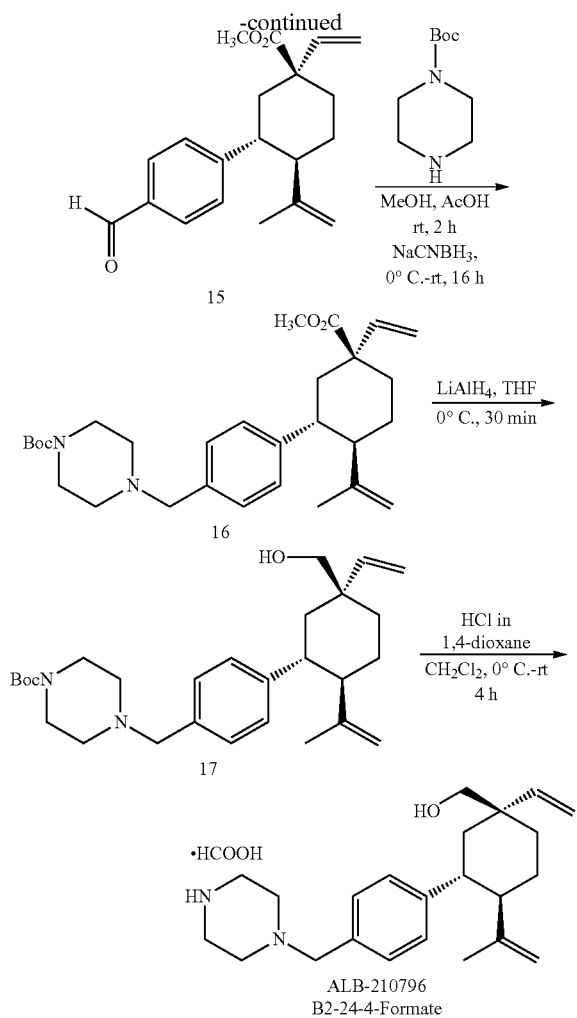

Production of Chemical Compound 2

At 0° C., NaIO$_4$ (626.4 g, 2.94 mol) was gradually added to a stirred solution of (−)-D-pinene (100.0 g, 0.73 mol) in water (1.0 L), acetonitrile (1.0 L) and CH$_2$Cl$_2$ (1.0 L), and the reaction mixture was stirred at the same temperature for 10 minutes. RuCl$_3$·nH$_2$O (4.56 g, 22.0 mmol) was gradually added to the reaction mixture at 0° C. and stirred at room temperature for 5 hours. Celite was added to the reaction mixture and filtered through a celite pad and washed with CH$_2$Cl$_2$ (500 mL). The filtrate was diluted with H$_2$O (LOL) and extracted with CH$_2$Cl$_2$ (2×500 mL). The organic layer was mixed, washed with brine (500 mL), dried over anhydrous Na$_2$SO$_4$ and concentrated under reduced pressure to obtain chemical compound 2 (100.0 g, crude) as a brown liquid. $^1$H NMR (400 MHz, CDCl$_3$) δ 2.58-2.51 (m, 3H), 2.38-2.30 (m, 1H), 2.25-2.21 (m, 1H), 2.08-2.01 (m, 1H), 1.98-1.90 (m, 1H), 1.57 (s, 1H), 1.35 (s, 3H), 0.84 (s, 3H).

Production of Chemical Compound 3

(PhSe)$_2$ (56.5 g, 0.181 mol) and SeO$_2$ (48.2 g, 0.434 mol) were added to a stirred solution of chemical compound 2 (50.0 g, 0.362 mol) in methanol (500 mL), and H$_2$SO$_4$ (13.5 mL, 0.253 mol) was dropped to the solution at 0° C. The reaction mixture was stirred at room temperature for 10 hours, quenched with ice cold water (LOL). EtOAc (LOL) was added to the mixture and the mixture was filtered through a celite pad. The organic layer was separated, washed with brine (500 mL), dried over anhydrous Na$_2$SO$_4$ and concentrated under reduced pressure. The crude chemical compound was purified by column chromatography on silica gel (60-120 mesh) using 5-10% EtOAc in eluent hexane to obtain chemical compound 3 (50.0 g, 47%) as a wine red liquid. $^1$H NMR (400 MHz, CDCl$_3$) δ 7.61-7.58 (m, 2H), 7.32-7.25 (m, 3H), 3.87 (dd, J=1.6 Hz, 8.0 Hz, 1H), 2.71-2.68 (m, 1H), 2.61-2.52 (m, 2H), 2.24-2.20 (m, 2H), 1.88 (d, J=8.00 Hz, 1H), 1.35 (s, 3H), 0.84 (m, 3H).

Production of Chemical Compound 4

At 0° C., 30% aq.H$_2$O$_2$ (26.0 mL, 0.229 mol) was dropped to a stirred solution of chemical compound 3 (45.0 g, 0.153 mol) in CH$_2$Cl$_2$ (450 mL), and then pyridine (43.8 mL, 0.544 mol) was dropped to the solution over 10 minutes and the reaction mixture was stirred at 5° C. or below for 3 hours. The reaction mixture was quenched with sodium thiosulfate (250 mL) and extracted with CH$_2$Cl$_2$ (2×250 mL). The organic layer was mixed, washed with 0.5N hydrochloric acid (2×250 mL), water (200 mL) and brine (200 mL), dried over anhydrous Na$_2$SO$_4$ and concentrated under reduced pressure at 25° C. or less. The crude chemical compound was purified by column chromatography on silica gel (60-120 mesh) using 5-10% EtOAc in eluent hexane to obtain chemical compound 4 (15.0 g, 72%) as a pale yellow oil. $^1$H NMR (400 MHz, CDCl$_3$) δ 7.54-7.50 (m, 1H), 5.95 (d, J=8.8 Hz, 1H), 2.86-2.83 (m, 1H), 2.76-2.70 (m, 1H), 2.64-2.56 (m, 1H), 2.15 (d, J=8 Hz, 1H), 1.51 (s, 3H), 1.04 (m, 3H).

Production of Chemical Compound 5

Chemical compound 4a (chemical compound 1 of scheme 4) (25.14 g, 165.43 mmol) and KOH (12.37 g, 220.58 mmol) were added to a stirred solution of chemical compound 4 (15.0 g, 110.29 mmol) in water (40.0 mL) and 1,4-dioxane (160 mL), and the reaction mixture was degassed under argon for 15 minutes. [Rh(COD)Cl]$_2$ complex (1.63 g, 3.30 mmol) was added thereto and again degassed under argon for 5 minutes. The obtained reaction mixture was stirred at 100° C. for 16 hours. The reaction mixture was cooled to room temperature, diluted with CH$_2$Cl$_2$ (500 mL), and filtered through a celite bed. The filtrate was washed with H$_2$O (500 mL), the organic layer was mixed, dried over anhydrous Na$_2$SO$_4$ and concentrated under reduced pressure. The crude chemical compound was purified by column chromatography on silica gel (60-120 mesh) using 20-40% EtOAc in eluent hexane to obtain chemical compound 5 (20 g, 74%) as a wine red oil. ESI MS m/z 245 [M+H]$^+$.

Production of Chemical Compound 6

At 10° C. or less, Zn(OAc)$_2$ (18 g, 98.29 mmol) and BF$_3$·OEt$_2$ (12.1 mL, 98.29 mmol) were added to a stirred solution of chemical compound 5 (20 g, 81.91 mmol) in Ac$_2$O (200 mL), and the solution was stirred for 16 hours at room temperature. The reaction mixture was neutralized with saturated NaHCO$_3$ (500 mL) and extracted with EtOAc (2×250 mL). The organic layer was mixed, washed with brine (250 mL), dried over anhydrous Na$_2$SO$_4$ and concentrated under reduced pressure. The crude chemical compound was purified by column chromatography on silica gel (60-120 mesh) using 30-40% EtOAc in eluent hexane to obtain chemical compound 6 (18.5 g, 68%) as an off-white solid. $^1$H-NMR (400 MHz, CDCl$_3$): δ 7.25 (d, J=8.40 Hz, 2H), 7.18 (d, J=8.00 Hz, 2H), 5.47-5.46 (m, 1H), 5.06 (s, 2H), 4.68 (s, 1H), 4.61 (s, 1H), 3.03-3.00 (m, 1H), 2.75-2.69 (m, 1H), 2.43-2.29 (m, 4H), 2.09 (s, 6H), 1.50 (s, 3H).

Production of Chemical Compound 7

At 0° C., NaH (2.26 g, 60% in mineral oil, 56.40 mmol) was gradually added to a solution of chemical compound 6 (18.5 g, 56.40 mmol) in methanol (185 mL). The reaction mixture was stirred at room temperature for 1 hour, quenched with saturated aq. NH$_4$Cl solution (100 mL) at 0° C., diluted with water (100 mL) and extracted with EtOAc (2×250 mL). The organic layer was mixed, washed with brine (200 mL), dried over anhydrous Na$_2$SO$_4$ and concentrated under reduced pressure. The crude chemical compound was washed with hexane (2×50 mL) and dried to obtain chemical compound 7 (13.5 g, crude) as an off-white solid. $^1$H-NMR (400 MHz, CDCl$_3$): δ 7.30 (d, J=8.00 Hz, 2H), 7.16 (d, J=8.00 Hz, 2H), 4.66 (s, 3H), 4.62 (s, 1H), 3.03-2.98 (m, 1H), 2.81-2.74 (m, 1H), 2.55-2.51 (m, 4H), 2.15-2.08 (m, 1H), 1.93-1.82 (m, 1H), 1.73-1.70 (m, 1H), 1.52 (s, 3H).

Production of Chemical Compound 8

At 0° C., 1M tert-BuOK solution (65.56 mL, 65.56 mmol) in THF was dropped to an ice-cold solution of p-toluenesulfonylmethylisocyanide (6.40 g, 32.78 mmol) in THF (80 mL), and the solution was stirred at the same temperature for 10 minutes. Chemical compound 7 (4 g, 16.39 mmol) in THF (10 mL) was added to the reaction mixture at 5° C. or less and stirred for 15 minutes. Methanol (40 mL) was added to the reaction mixture and stirred under reflux for 1 hour. The residual solvent was evaporated under reduced pressure. H$_2$O (100 mL) was added to the obtained residue and the residue was extracted with EtOAc (2×100 mL). The organic layer was mixed, washed with brine (50 mL), dried over anhydrous Na$_2$SO$_4$ and concentrated under reduced pressure. The crude chemical compound was purified by combiflash chromatography using 30-40% EtOAc elution in eluent hexane to obtain chemical compound 8 (1.53 g, 36%) as a pale yellow viscous material. It was used in the next reaction without further purification.

Production of Chemical Compound 9

At room temperature, KOH (4.4 g, 78.38 mmol) was added to a stirred solution of chemical compound 8 (2.0 g, 7.83 mmol) in 2-propanol (20 mL). The reaction mixture was stirred under reflux for 48 hours. The residual solvent was evaporated under reduced pressure and the obtained crude product was dissolved in EtOAc (100 mL) and washed with water (50 mL). The aqueous layer was neutralized with 2M HCl and extracted with EtOAc (2×100 mL). The organic layer was mixed, washed with brine (50 mL), dried over anhydrous Na$_2$SO$_4$ and concentrated under reduced pressure to obtain chemical compound 9 (1.0 g, crude) as a gray solid. ESI MS m/z 273 [M−H]$^+$.

Production of Chemical Compound 10

At 5° C. or less, K$_2$CO$_3$ (19.78 g, 142.32 mmol) and MeI (8.8 mL, 142.32 mmol) in that order were dropped to a stirred solution of chemical compound 9 (13.0 g, 47.44 mmol) in methanol (30 mL) and acetonitrile (150 mL). The reaction mixture was stirred at room temperature for 16 hours. The residual solvent was evaporated under reduced pressure, water (100 mL) was added to the residue and extracted with EtOAc (2×100 mL). The organic layer was mixed, washed with water (50 mL), brine (50 mL), dried over anhydrous Na$_2$SO$_4$ and concentrated under reduced pressure. The crude chemical compound was purified by combiflash chromatography using 10-20% EtOAc in eluent hexane to obtain chemical compound 10 (8.20 g, 60%) as a colorless oil. $^1$H-NMR (400 MHz, CDCl$_3$): δ 7.26 (d, J=8.0 Hz, 2H), 7.13 (d, J 8.0 Hz, 2H), 4.64 (d, J=4.80 Hz, 2H), 4.56-4.53 (m, 2H), 3.65 (s, 3H), 2.59-2.46 (m, 2H), 2.36-2.30 (m, 1H), 2.12-2.08 (m, 2H), 1.91-1.86 (m, 1H), 1.67-1.60 (m, 3H), 1.52-1.49 (m, 4H).

Production of Chemical Compound 11

At 0° C., imidazole (4.8 g, 71.12 mmol) and TBDMSCl (5.14 g, 34.14 mmol) were gradually added to a stirred solution of chemical compound 10 (8.20 g, 28.45 mmol) in CH$_2$Cl$_2$ (160 mL). The reaction mixture was stirred at room temperature for 16 hours, quenched with saturated aq. NaHCO$_3$ (200 mL) and extracted with CH$_2$Cl$_2$ (2×100 mL). The organic layer was mixed, washed with water (50 mL) and brine (50 mL), dried over anhydrous Na$_2$SO$_4$ and concentrated under reduced pressure. The crude chemical compound was purified by combiflash chromatography using 10-20% EtOAc in eluent hexane to obtain chemical compound 11 (10.0 g, 87%) as a colorless oil. $^1$H-NMR (400 MHz, CDCl$_3$): δ 7.20 (d, J=8.0 Hz, 2H), 7.09 (d, J=8.0 Hz, 2H), 4.70 (s, 2H), 4.55 (s, 1H), 4.53 (s, 1H), 3.65 (s, 3H), 2.47-2.45 (m, 2H), 2.35-2.28 (m, 1H), 2.11-2.08 (m, 2H), 1.90-1.86 (m, 1H), 1.67-1.59 (m, 2H), 1.51 (s, 1H), 1.49 (s, 3H), 0.93 (s, 9H), 0.08 (s, 6H).

Production of Chemical Compound 12

At −78° C., 2M lithium diisopropylamide solution (4.47 mL, 8.94 mmol) in THF was dropped to a stirred solution of chemical compound 11 (1.20 g, 2.98 mmol) in THF (60 mL). The reaction mixture was stirred at −78° C. for 30 minutes, then cooled to −105° C. (using MeOH, liquid N$_2$) and phenyl vinyl sulfoxide (0.6 mL, 4.47 mmol) was added thereto. The reaction mixture was stirred at −105° C. for 30 minutes. The reaction mixture was quenched with saturated NH$_4$Cl solution (25 mL) and extracted with EtOAc (2×50 mL). The organic layer was mixed, washed with brine (50 mL), dried over anhydrous Na$_2$SO$_4$ and concentrated under reduced pressure. The crude chemical compound was purified by combiflash chromatography using 30-40% EtOAc in eluent hexane to obtain chemical compound 12 (0.47 g, 28%) as a pale yellow oil. ESI MS m/z 555 [M+H]$^+$.

Production of Chemical Compound 13

At room temperature, NaHCO$_3$ (5.1 g, 61.28 mmol) was added to a stirred solution of chemical compound 12 (3.40 g, 6.128 mmol) in xylene (51 mL), and the reaction mixture was stirred under reflux for 16 hours. The reaction mixture was cooled to room temperature, diluted with H$_2$O (50 mL) and extracted with EtOAc (3×50 mL). The organic layer was mixed, washed with brine (50 mL), dried over anhydrous Na$_2$SO$_4$ and concentrated under reduced pressure. The crude chemical compound was purified by combiflash chromatography using 10-30% EtOAc in eluent hexane to obtain 13 (2.0 g, 76%) as a colorless viscous material. $^1$H-NMR (400 MHz, CDCl$_3$): δ 7.21 (d, J 8.0 Hz, 2H), 7.11 (d, J=8.0 Hz, 2H), 5.87-5.78 (m, 1H), 5.09-5.04 (m, 1H), 4.70 (s, 2H), 4.54-4.52 (m, 2H), 3.77 (s, 3H), 2.69-2.61 (m, 1H), 2.43-2.41 (m, 2H), 2.33-2.27 (m, 1H), 1.80-1.75 (m, 1H), 1.58 (s, 1H), 1.51-1.39 (m, 6H), 0.93 (s, 9H), 0.08 (s, 6H).

Production of Chemical Compound 14

At 0° C., 1M TBAF (9.32 mL, 9.32 mmol) in THF was added to a stirred solution of chemical compound 13 (2.0 g, 4.66 mmol) in THF (40.0 mL). The reaction mixture was stirred at room temperature for 3 hours, quenched with H$_2$O (50 mL) and extracted with EtOAc (2×50 mL). The organic layer was mixed, washed with brine (50 mL), dried over anhydrous Na$_2$SO$_4$ and concentrated under reduced pressure. The crude chemical compound was purified by combiflash chromatography using 20-40% EtOAc in eluent hexane to obtain chemical compound 14 (1.20 g, 82%) as a pale yellow viscous material. ESI MS m/z 332 [M+H$_2$O]+.

Production of Chemical Compound 15

At 0° C., Dess-Martin periodinane (3.23 g, 7.63 mmol) was added to a stirred solution of chemical compound 14 (1.20 g, 3.81 mmol) in CH$_2$Cl$_2$ (25.0 mL). The reaction mixture was stirred at room temperature for 2 hours, quenched with saturated Na$_2$S$_2$O$_3$ (25.0 mL), stirred for 10 minutes, and extracted with CH$_2$Cl$_2$ (2×50 mL). The organic layer was washed with saturated NaHCO$_3$ solution (25.0 mL), brine (50 mL), dried over anhydrous Na$_2$SO$_4$ and concentrated under reduced pressure. The crude chemical compound was purified by combiflash chromatography using 10-20% EtOAc in eluent hexane to obtain chemical compound 15 (1.0 g, 84%) as a pale yellow viscous material. ESI MS m/z 313 [M+H]$^+$.

Production of Chemical Compound 16

AcOH (0.1 mL, 1.6 mmol) and tert-butyl piperzine-1-carboxylate (1.2 g, 6.40 mmol) in that order were added to a stirred solution of chemical compound 15 (1.0 g, 3.20 mmol) in MeOH (20.0 mL). The reaction mixture was stirred at room temperature for 2 hours. The reaction mixture was gradually added to NaCNBH$_3$ (0.60 g, 9.6 mmol) at 0° C. and stirred at room temperature for 16 hours. The reaction mixture was quenched with H$_2$O (25 mL) and extracted with CH$_2$Cl$_2$ (2×50 mL). The organic layer was mixed, washed with brine (50 mL), dried over anhydrous Na$_2$SO$_4$ and concentrated under reduced pressure. The crude product was purified by combiflash chromatography using 30-40% EtOAc in eluent hexane to obtain chemical compound 15 (1.25 g, 81%) as a colorless viscous material. ESI MS m/z 483 [M+H]$^+$.

Production of Chemical Compound 17

At 0° C., 2M LiAlH$_4$ (3.1 mL, 6.2 mmol) in THF was dropped to a stirred solution of chemical compound 16 (1.0 g, 2.07 mmol) in THF (50 mL). The reaction mixture was stirred at 0° C. for 30 minutes, quenched with saturated NH$_4$Cl solution (25.0 mL) and extracted with EtOAc (2×50.0 mL). The organic layer was mixed, washed with brine (25.0 mL), dried over anhydrous Na$_2$SO$_4$ and concentrated under reduced pressure. The crude chemical compound was purified by combiflash chromatography using 30-50% EtOAc in eluent hexane to obtain chemical compound 17 (1.0 g, 88%) as a colorless viscous material. ESI MS m/z 455 [M+H]$^+$.

Production of Chemical Compound ALB-210796 (B2-24-4·HCOOH)

At 0° C., 4M HCl in 1,4-dioxane (10 mL) dropwise was dropped to a stirred solution of chemical compound 17 (1.0 g, 2.21 mmol) in CH$_2$Cl$_2$ (25 mL). The reaction mixture was stirred at room temperature for 4 hours and the residual solvent was evaporated under reduced pressure. The crude product was washed with hexane (2×20 mL) and purified by preparative HPLC eluting with CH$_3$CN in H$_2$O using ammonium formate as buffer. The purified fractions were concentrated under reduced pressure and lyophilized to obtain the formate salt of ALB-210796 (B2-24-4·HCOOH) (420 mg, 47%) as an off-white solid. $^1$H-NMR (400 MHz, DMSO-d$_6$): 8.30 (s, 1H), 7.15-7.10 (m, 4H), 5.89-5.81 (m, 1H), 4.94-4.89 (m, 2H), 4.54 (d, J=1.60 Hz, 1H), 4.45-4.44 (m, 1H), 3.54 (s, 2H), 3.98 (s, 2H), 2.84-2.67 (m, 5H), 2.36-2.26 (m, 5H), 1.77-1.58 (m, 5H), 1.48 (s, 3H), 1.40-1.31 (m, 2H).

Example 16: Confirmation of Therapeutic Effect of B2-24-4-5A·HCOOH in Mouse Model of Spontaneous Systemic Lupus Erythematosus Systemic lupus erythematosus model mice (NZBWF1, 20 weeks old, female, n=55) were divided into saline-administered group (control, n=25), B2-24-4-5A·HCOOH-administered group (n=10), B2-24-4·HCOOH-administered group (n=5) and HCQ-administered group (n=15). The saline-administered group received saline (100 l) orally once a day, every day; the B2-24-4-5A·HCOOH-administered group received 10 mg/kg of B2-24-4-5A·HCOOH (100 l) orally once a day, every day; the B2-24-4·HCOOH-administered group received 10 mg/kg of B2-24-4·HCOOH (100 l) orally once a day, every day; the HCQ-administered group received 10 mg/kg of HCQ (100 l) orally once a day, every day. Fifteen weeks after the start of treatment, urine was collected from surviving mice in the saline-administered group (control, n=17), B2-24-4-5A·HCOOH-administered group (n=10), B2-24-4·HCOOH-administered group (n=5), and HCQ-administered group (n=12), and the mice were euthanized. After euthanasia, blood was drawn from the abdominal aorta of the mice, and the kidneys and spleen were removed.

Mice that died of natural causes during the 15-week period from the start of treatment were counted as deaths, and survival analysis was performed using the Kaplan Meier method. Blood collected from the abdominal aorta of each mouse, excluding the deceased cases, was centrifuged and serum was prepared. Determination of urea nitrogen and creatinine levels in serum was entrusted to Oriental Yeast Co. Albumin levels in urine were determined by ELISA (used kit: Levis Urinary Albumin-Mouse (S-type) (trade name) (Fujifilm Wako Shibayagi Corporation)). The removed kidneys were fixed with 4% (w/v) paraformaldehyde, and immunohistochemical staining was entrusted to Morpho Technology, Inc. In PAS-stained kidney tissue sections, histological findings of 100 glomeruli were evaluated. For increased cells and substrate in the mesangial area, endothelial cell swelling and cellular infiltration of the capillary lumen (intratubular proliferation), and glomeruli with inflammatory crescents (extratubular proliferation), each of the 100 glomeruli was assigned a grade from grade 0 to grade 2 according to severity and scored on a 6-point scale. The results are shown in FIGS. 10A to 10H and Table 8.

Figure 10A:
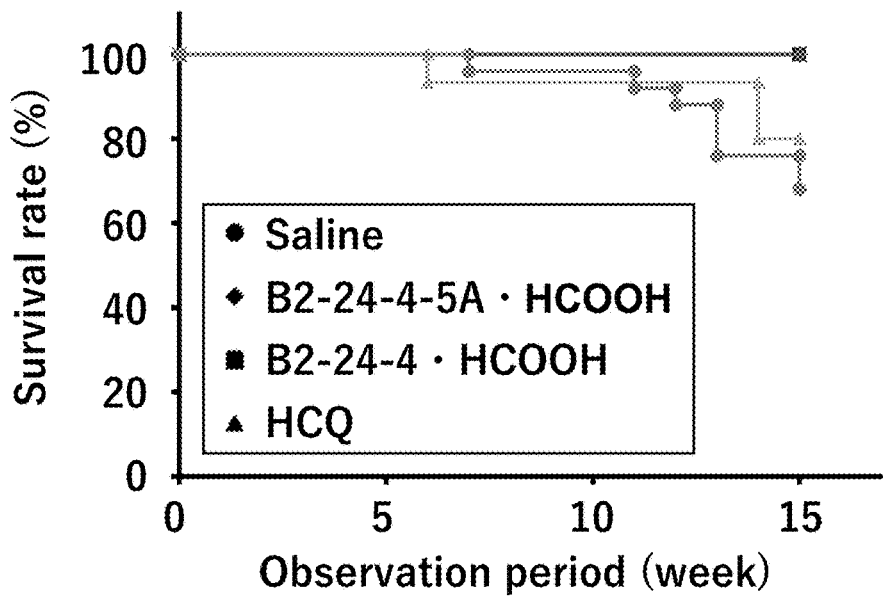
FIG. 10A shows the survival curves of systemic lupus erythematosus model mice (saline-administered, B2-24-4-5A·HCOOH-administered, B2-24-4·HCOOH-administered and HCQ-administered groups) during the treatment period.
Figure 10B:
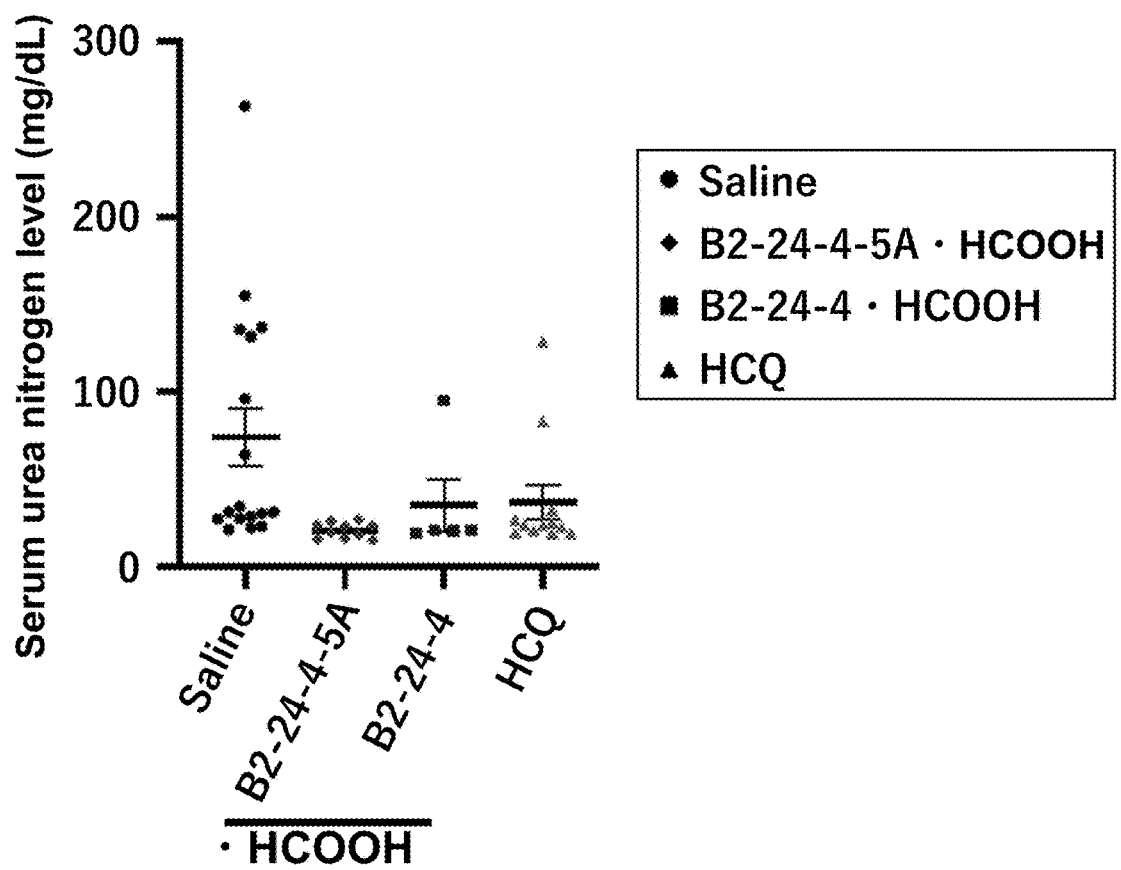
FIG. 10B shows the serum urea nitrogen levels of systemic lupus erythematosus model mice (saline-administered, B2-24-4-5A·HCOOH-administered, B2-24-4·HCOOH-administered and HCQ-administered groups).
Figure 10C:
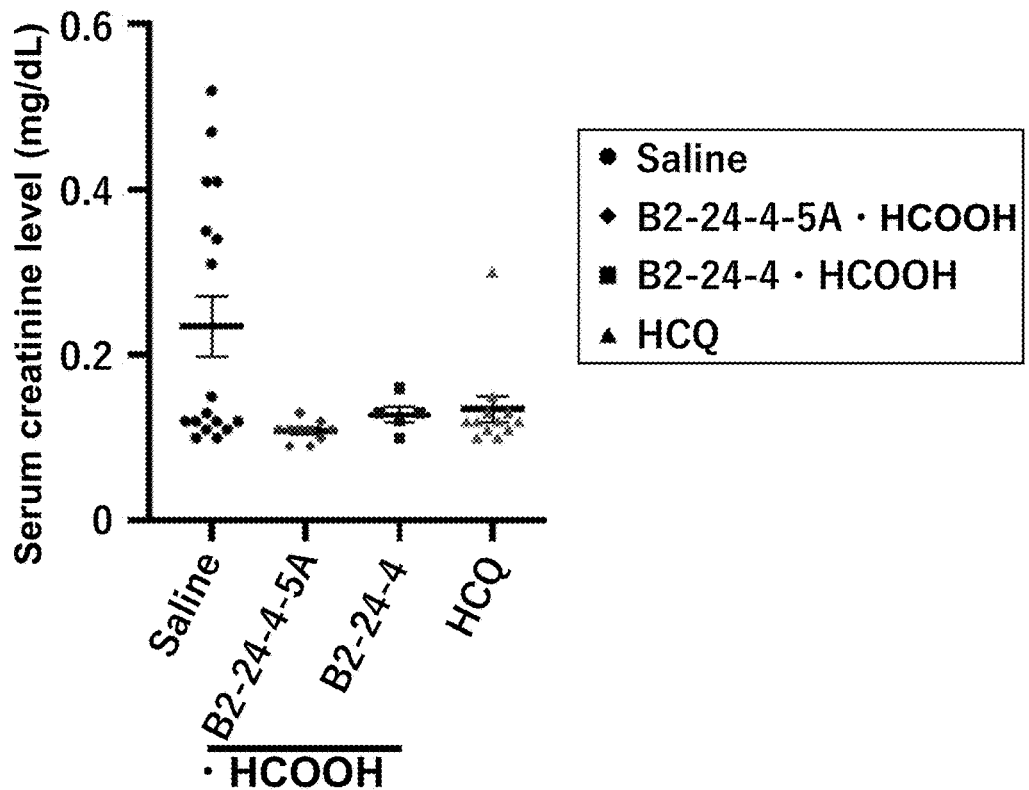
FIG. 10C shows the serum creatinine levels of systemic lupus erythematosus model mice (saline-administered, B2-24-4-5A·HCOOH-administered, B2-24-4·HCOOH-administered and HCQ-administered groups).
Figure 10D:
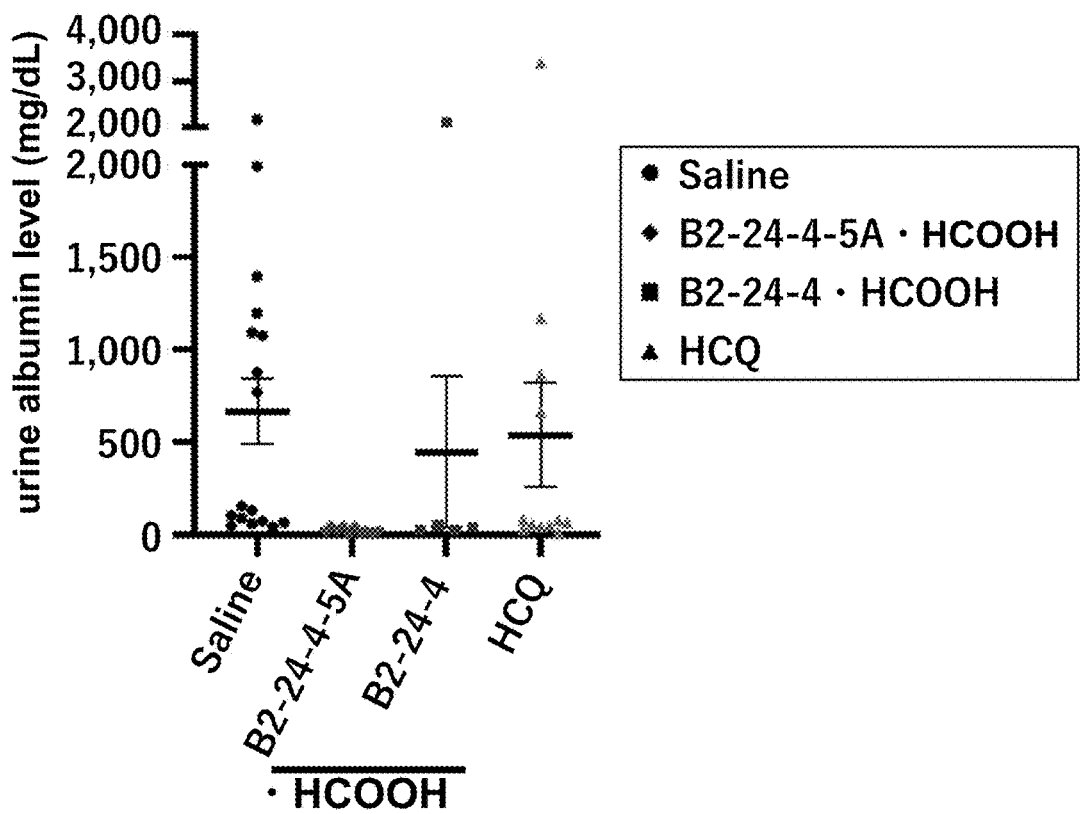
FIG. 10D shows the urinary albumin levels of systemic lupus erythematosus model mice (saline-administered, B2-24-4-5A·HCOOH-administered, B2-24-4·HCOOH-administered and HCQ-administered groups).
Figure 10E:
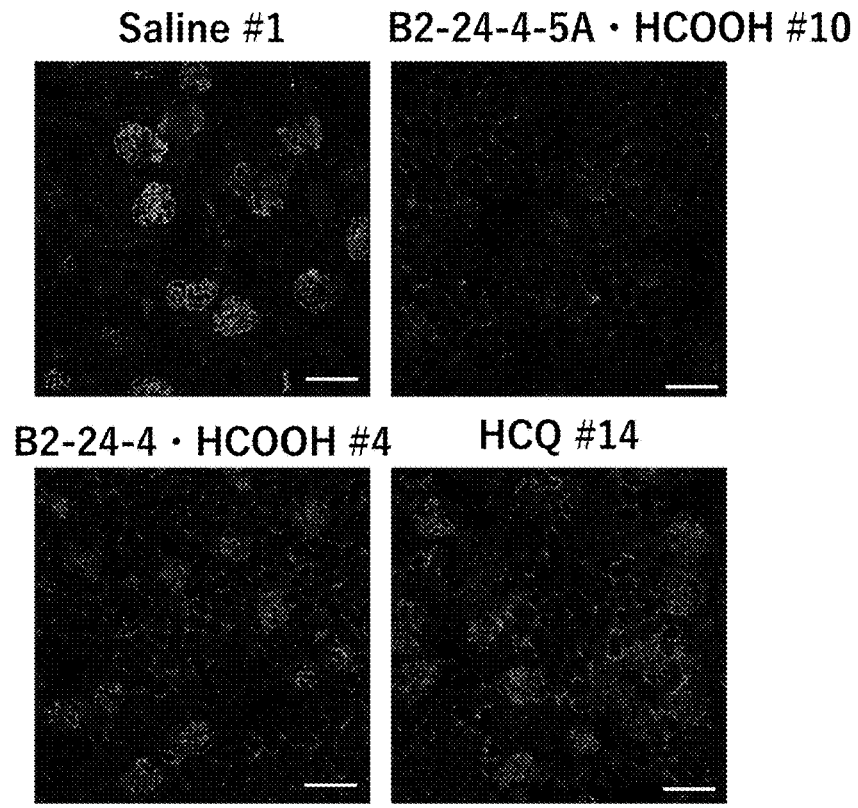
FIG. 10E shows photomicrographs of IgG deposition in glomeruli of systemic lupus erythematosus model mice (mouse (#1) in the saline-administered group, mouse (#10) in the B2-24-4-5A·HCOOH-administered group, mouse (#4) in the B2-24-4·HCOOH-administered group and mouse (#14) in the HCQ-administered group).
Figure 10F:
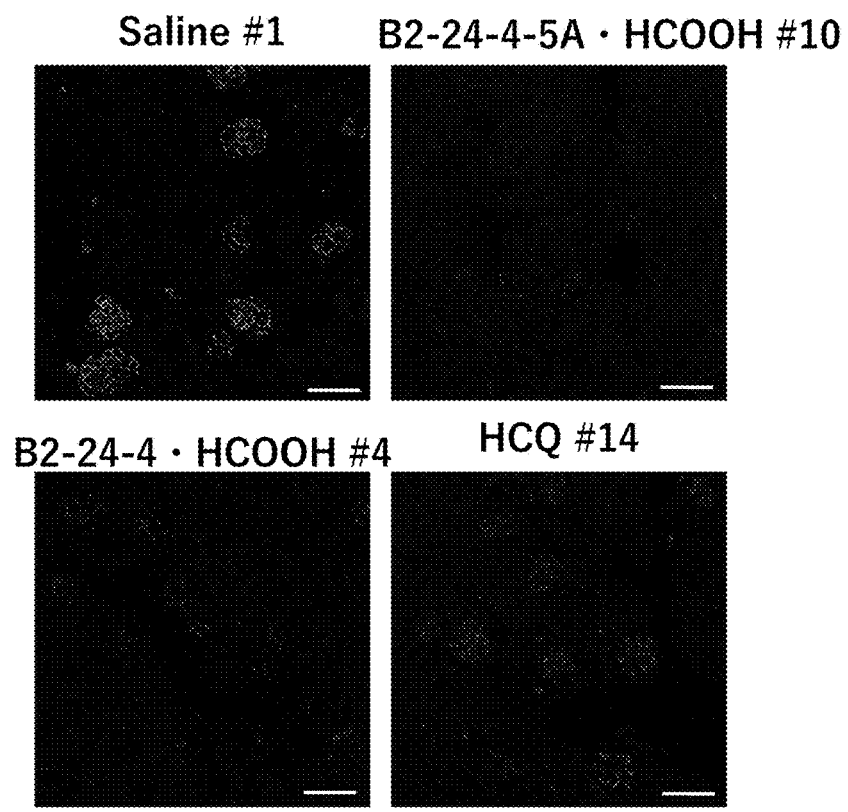
FIG. 10F shows photographs of C3 deposition in glomeruli of systemic lupus erythematosus model mice (mouse (#1) in the saline-administered group, mouse (#10) in the B2-24-4-5A·HCOOH-administered group, mouse (#4) in the B2-24-4·HCOOH-administered group and mouse (#14) in the HCQ-administered group).
Figure 10G:
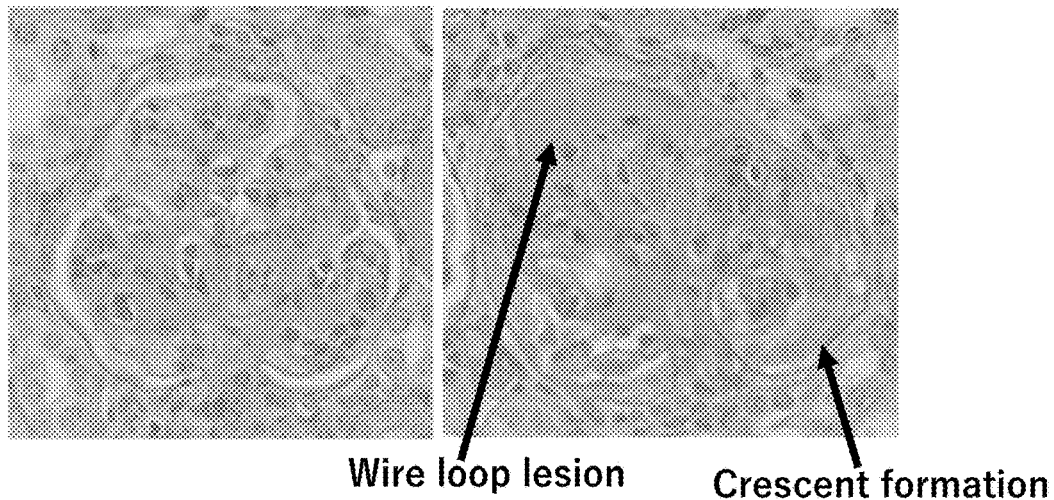
FIG. 10G shows photographs of stained kidney tissue sections of mouse (#1) in the saline-administered group.
Figure 10H:
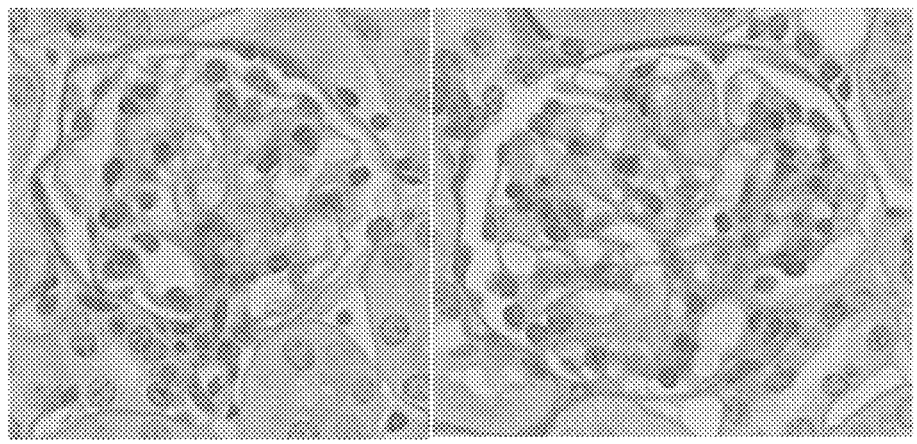
FIG. 10H shows photographs of stained renal tissue sections of mouse (#1) in the B2-24-4-5A·HCOOH-administered group.

FIG. 10A shows the survival curves during the administration period. FIG. 10B shows serum urea nitrogen levels. FIG. 10C shows serum creatinine levels. FIG. 10D shows urine albumin levels. FIG. 10E shows pictures of IgG deposition in the glomeruli of a mouse (#1) in saline-administered group, a mouse (#10) in the B2-24-4-5A·HCOOH-administered group, a mouse (#4) in the B2-24-4·HCOOH-administered group and a mouse (#14) in the HCQ-administered mouse. FIG. 10F is a photograph showing C3 deposition in the glomeruli of a mouse (#1) in the saline-administered group, a mouse (#10) in the B2-24-4-5A·HCOOH-administered group, a mouse (#4) in the B2-24-4·HCOOH-administered group and a mouse (#14) in the HCQ-administered group. FIG. 10G shows a stained photograph of a renal tissue section of a mouse (#1) in the saline-administered group. In the renal tissue sections of a mouse (#1) in the saline-administered group, findings of active glomerulonephritis such as diffuse mesangial and intratubular proliferation were observed. FIG. 10H shows stained photomicrographs of renal tissue sections of a mouse (#1) in the B2-24-4-5A·HCOOH-administered group. Only focal mesangial cell and substrate increase was observed in renal tissue sections of a mouse (#1) in the B2-24-4-5A·HCOOH-administered group. The plots in FIGS. 10B, 10C, and 10D show the data for each individual, each bold line is the mean of the group data, and each error bar standard error. Scale bars in FIGS. 10E and 10F represent 100 µm.

As is clear from FIGS. 10A to 10H, prolonged survival, suppression of the increase in serum urea nitrogen levels, suppression of the increase in serum creatinine levels, suppression of urine albumin levels, suppression of IgG deposition in glomeruli, suppression of C3 deposition in glomeruli, and a significant decrease in the activity of lupus nephritis were observed in the B2-24-4-5A·HCOOH-administered group or B2-24-4·HCOOH-administered group compared to the control saline-administered group or HCQ-administered group.

TABLE 8

| | Histological findings and scoring | | | | | | | | | |
|---|---|---|---|---|---|---|---|---|---|---|
| mouse# | Mes0 | Mes1 | Mes2 | Inside 0 | Inside 1 | Inside 2 | Outside 0 | Outside 1 | Outside 2 | score | Tubulo-interstitial inflammation |
| Saline-#1 | 1 | 16 | 83 | 2 | 10 | 88 | 81 | 17 | 2 | 3.89 | Found |
| Saline-#2 | 82 | 18 | 0 | 100 | 0 | 0 | 100 | 0 | 0 | 0.18 | Found |
| Saline-#3 | 4 | 26 | 70 | 4 | 17 | 79 | 96 | 4 | 0 | 3.45 | Found |
| Saline-#4 | 85 | 15 | 0 | 100 | 0 | 0 | 100 | 0 | 0 | 0.15 | Found |
| Saline-#5 | 11 | 29 | 60 | 8 | 40 | 52 | 80 | 15 | 5 | 3.18 | Found |
| Saline-#6 | 0 | 37 | 63 | 31 | 41 | 28 | 58 | 32 | 10 | 3.12 | Found |
| Saline-#9 | 22 | 69 | 9 | 63 | 36 | 1 | 100 | 0 | 0 | 1.25 | Found |
| Saline-#11 | 75 | 25 | 0 | 86 | 14 | 0 | 100 | 0 | 0 | 0.39 | Found |
| Saline-#12 | 7 | 13 | 80 | 9 | 34 | 57 | 74 | 18 | 8 | 3.55 | Found |
| Saline-#13 | 2 | 25 | 73 | 51 | 47 | 2 | 100 | 0 | 0 | 2.22 | Found |
| Saline-#15 | 84 | 16 | 0 | 98 | 2 | 0 | 100 | 0 | 0 | 0.18 | Not found |
| Saline-#16 | 91 | 9 | 0 | 99 | 1 | 0 | 100 | 0 | 0 | 0.10 | Not found |
| Saline-#17 | 0 | 16 | 84 | 15 | 57 | 28 | 90 | 4 | 6 | 3.13 | Found |
| Saline-#19 | 70 | 25 | 5 | 100 | 0 | 0 | 100 | 0 | 0 | 0.35 | Found |
| Saline-#21 | 91 | 9 | 0 | 100 | 0 | 0 | 100 | 0 | 0 | 0.09 | Not found |
| Saline-#22 | 13 | 32 | 55 | 37 | 39 | 24 | 40 | 46 | 14 | 3.03 | Found |
| Saline-#25 | 65 | 34 | 1 | 90 | 10 | 0 | 100 | 0 | 0 | 0.46 | Found |
| B2-24-4-5A·HCOOH-#1 | 80 | 19 | 1 | 99 | 1 | 0 | 99 | 1 | 0 | 0.23 | Not found |
| B2-24-4-5A·HCOOH-#2 | 86 | 13 | 1 | 100 | 0 | 0 | 100 | 0 | 0 | 0.15 | Found |
| B2-24-4-5A·HCOOH-#3 | 86 | 12 | 2 | 78 | 18 | 4 | 100 | 0 | 0 | 0.42 | Found |
| B2-24-4-5A·HCOOH-#4 | 92 | 8 | 0 | 99 | 1 | 0 | 100 | 0 | 0 | 0.09 | Not found |
| B2-24-4-5A·HCOOH-#5 | 80 | 20 | 0 | 96 | 4 | 0 | 100 | 0 | 0 | 0.24 | Not found |
| B2-24-4-5A·HCOOH-#6 | 97 | 3 | 0 | 100 | 0 | 0 | 100 | 0 | 0 | 0.03 | Not found |
| B2-24-4-5A·HCOOH-#7 | 96 | 4 | 0 | 100 | 0 | 0 | 100 | 0 | 0 | 0.04 | Not found |
| B2-24-4-5A·HCOOH-#8 | 92 | 8 | 0 | 94 | 6 | 0 | 100 | 0 | 0 | 0.14 | Found |
| B2-24-4-5A·HCOOH-#9 | 94 | 6 | 0 | 97 | 3 | 0 | 100 | 0 | 0 | 0.09 | Found |
| B2-24-4-5A·HCOOH-#10 | 80 | 20 | 0 | 74 | 20 | 6 | 100 | 0 | 0 | 0.52 | Found |
| B2-24-4·HCOOH-#1 | 94 | 6 | 0 | 100 | 0 | 0 | 100 | 0 | 0 | 0.06 | Not found |
| B2-24-4·HCOOH-#2 | 96 | 4 | 0 | 100 | 0 | 0 | 100 | 0 | 0 | 0.04 | Not found |
| B2-24-4·HCOOH-#3 | 18 | 69 | 13 | 11 | 60 | 29 | 100 | 0 | 0 | 2.13 | Found |
| B2-24-4·HCOOH-#4 | 67 | 33 | 0 | 100 | 0 | 0 | 100 | 0 | 0 | 0.33 | Found |
| B2-24-4·HCOOH-#5 | 77 | 23 | 0 | 100 | 0 | 0 | 100 | 0 | 0 | 0.23 | Found |
| HCQ-#1 | 15 | 72 | 13 | 43 | 38 | 19 | 100 | 0 | 0 | 1.74 | Not found |
| HCQ-#2 | 43 | 57 | 0 | 87 | 13 | 0 | 100 | 0 | 0 | 0.70 | Found |
| HCQ-#4 | 100 | 0 | 0 | 100 | 0 | 0 | 100 | 0 | 0 | 0.00 | Not found |
| HCQ-#5 | 16 | 81 | 3 | 38 | 47 | 15 | 100 | 0 | 0 | 1.64 | Found |
| HCQ-#6 | 75 | 25 | 0 | 95 | 5 | 0 | 100 | 0 | 0 | 0.30 | Found |
| HCQ-#7 | 8 | 66 | 26 | 12 | 36 | 52 | 100 | 0 | 0 | 2.58 | Found |
| HCQ-#8 | 93 | 7 | 0 | 100 | 0 | 0 | 100 | 0 | 0 | 0.07 | Not found |
| HCQ-#10 | 87 | 13 | 0 | 99 | 1 | 0 | 100 | 0 | 0 | 0.14 | Not found |
| HCQ-#12 | 7 | 46 | 47 | 15 | 64 | 21 | 53 | 26 | 21 | 3.14 | Found |
| HCQ-#13 | 68 | 31 | 1 | 96 | 4 | 0 | 100 | 0 | 0 | 0.37 | Found |
| HCQ-#14 | 20 | 43 | 37 | 22 | 58 | 20 | 96 | 4 | 0 | 2.19 | Found |
| HCQ-#15 | 84 | 16 | 0 | 98 | 2 | 0 | 100 | 0 | 0 | 0.18 | Not found |

Mes: increase in cells and substrates in the mesangium region
Inside: endothelial cell swelling and cellular infiltration of capillary lumen
Outside: glomerulus with semilunar
Grade 0: None
Grade 1: Moderate or lower
Grade 2: Moderate or higher While there were individual differences in nephritis activity in the control saline-administered group, most of the B2-24-4-5A·HCOOH-administered group showed improvement not only in glomerulonephritis but also in tubulointerstitial inflammation.

Figure 11A:
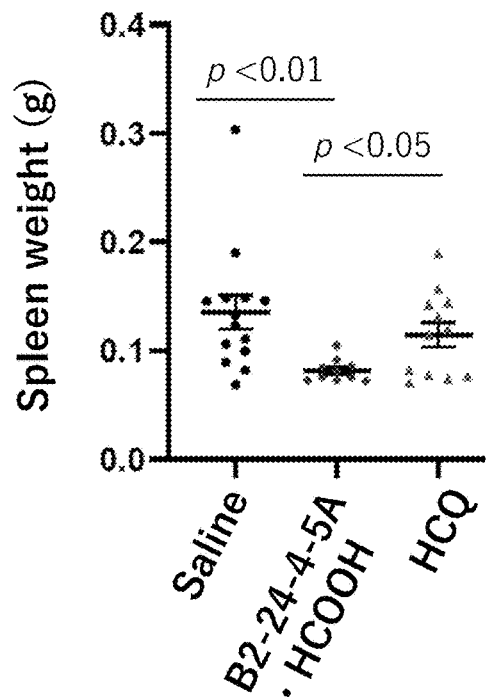
FIG. 11A shows the weight of the spleen of the systemic lupus erythematosus model mice (saline-administered, B2-24-4-5A·HCOOH-administered, and HCQ-administered groups).

Example 17: Analysis of Spleen Tissue in NZBWF1 Mice Treated with B2-24-4-5A·HCOOH The weight and splenocyte count of the spleen obtained in Example 16 were analyzed. Spleen weight is shown in FIG. 11A and splenocyte count in FIG. 11B.

Figure 11B:
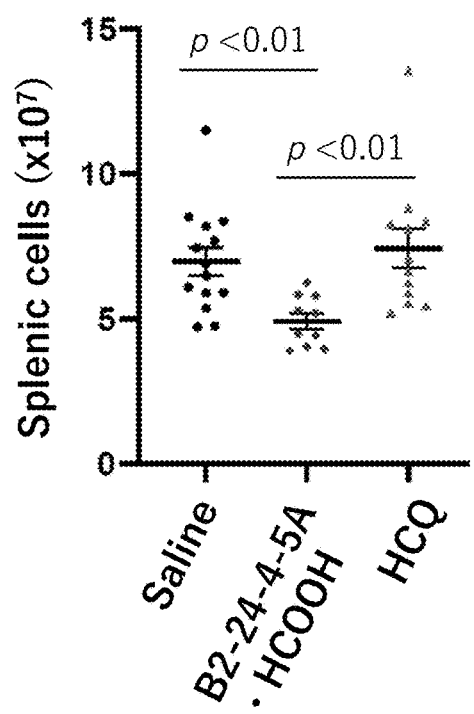
FIG. 11B shows the number of splenocytes in the systemic lupus erythematosus model mice (saline-administered, B2-24-4-5A·HCOOH-administered, and HCQ-administered groups).
Figure 12:
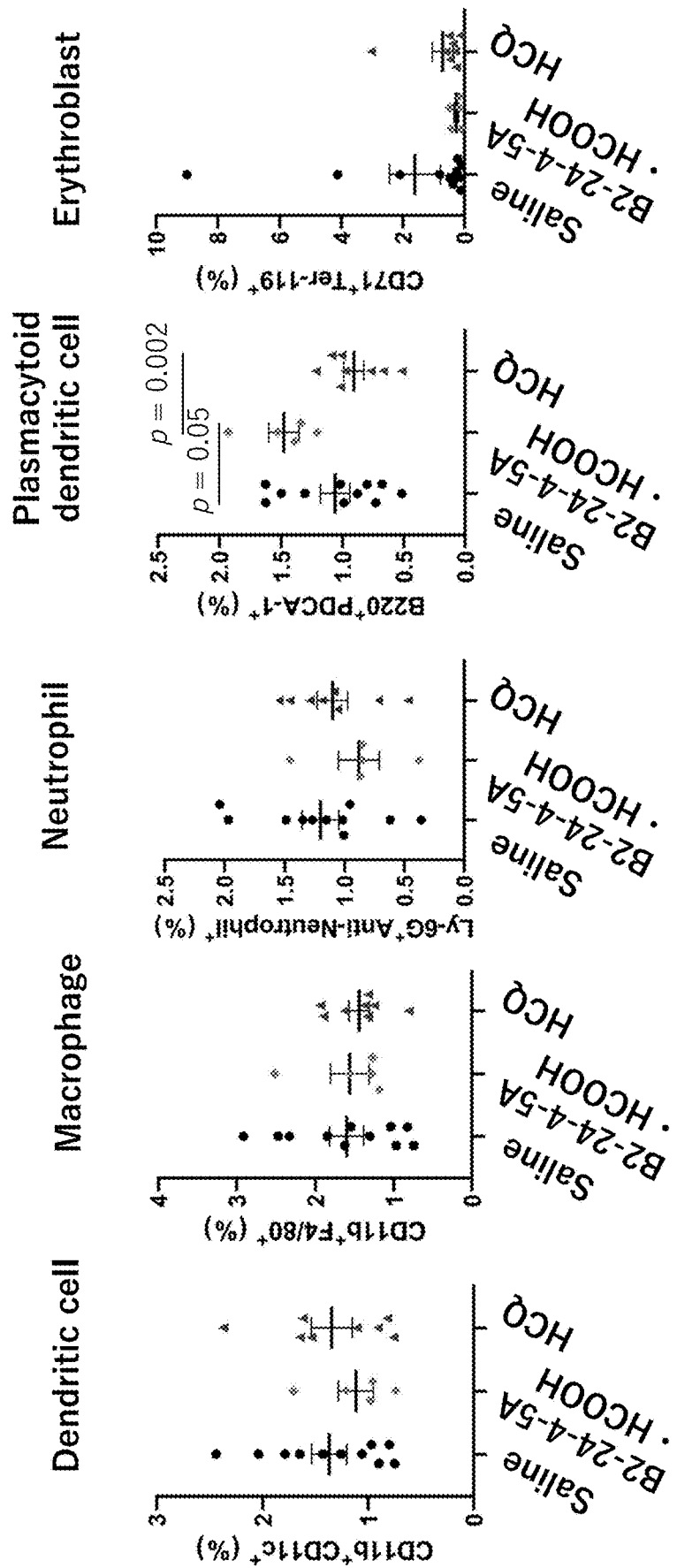
FIG. 12(a) to 12(e) show the percentage of various cells in the spleen.
Figure 13:
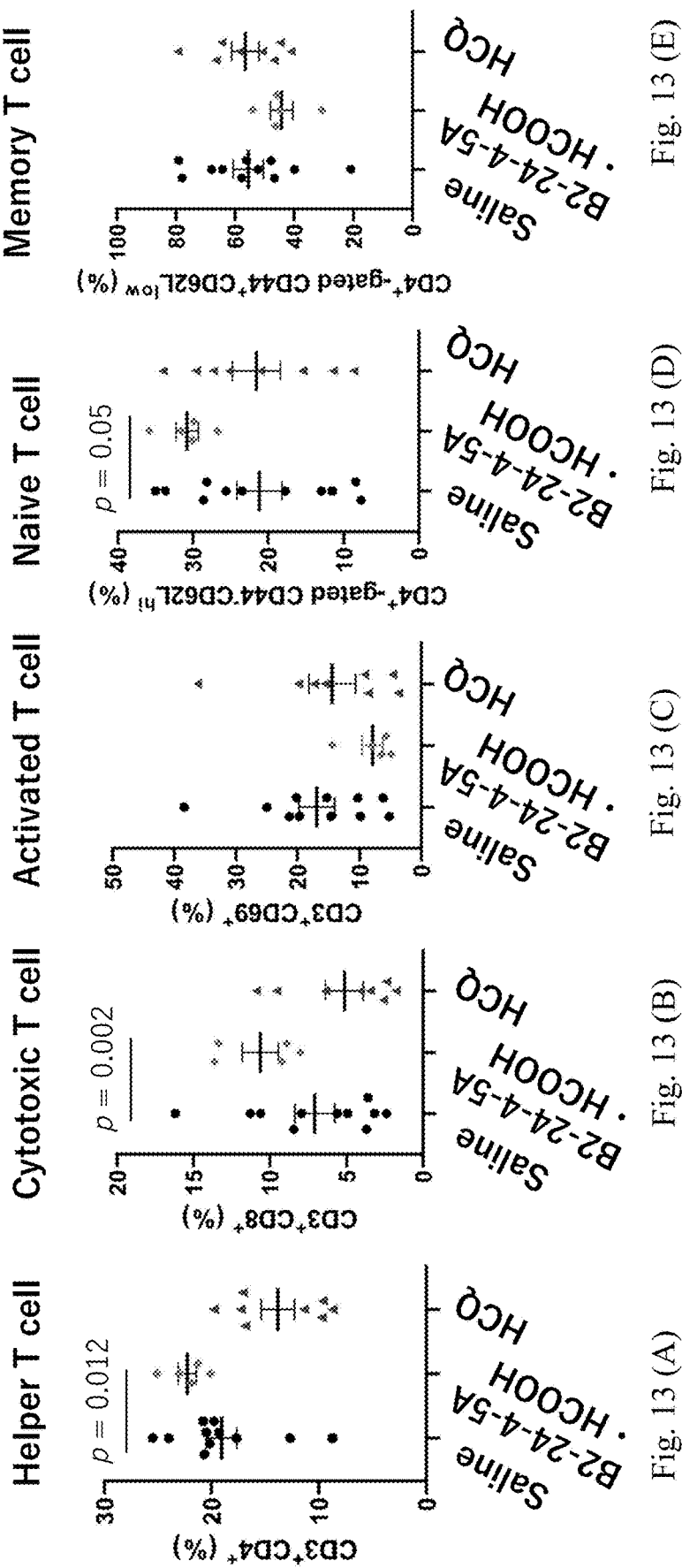
FIG. 13(a) to 13(e) show the percentage of various cells in the spleen.
Figure 14:
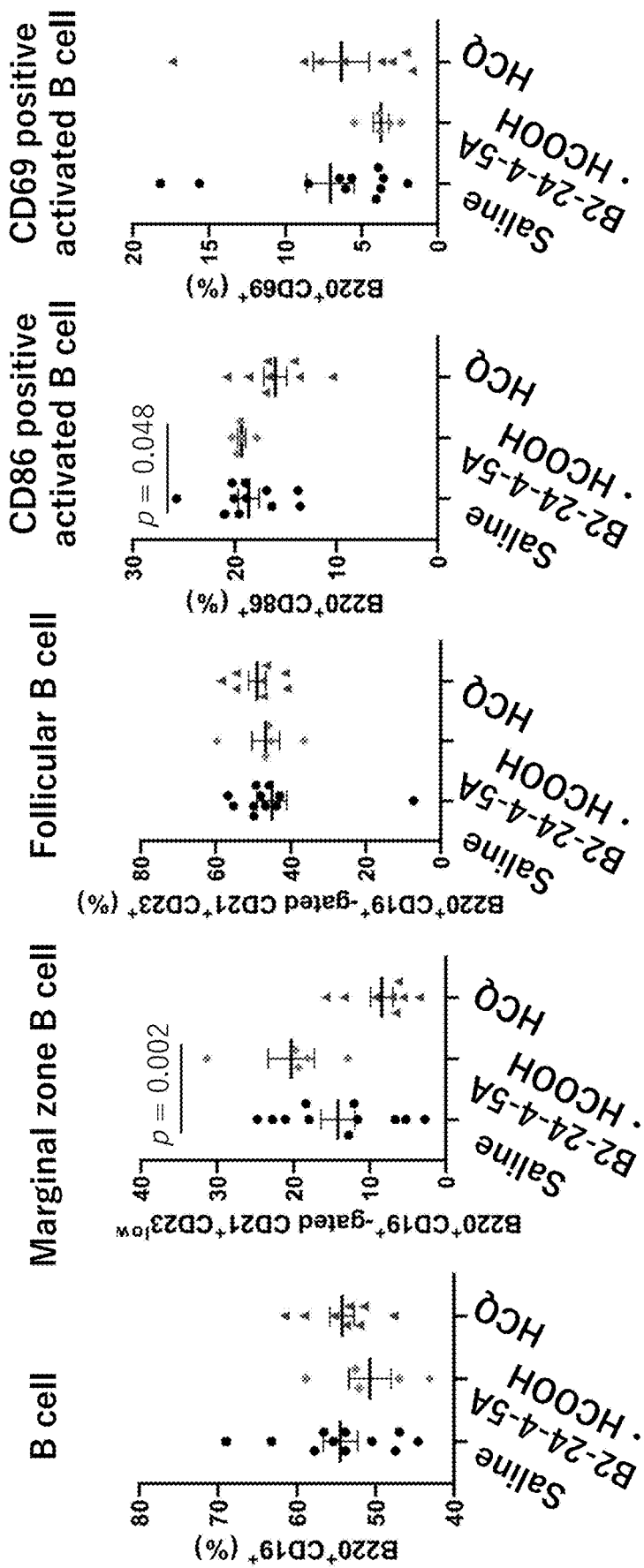
FIG. 14(a) to 14(e) show the percentage of various cells in the spleen.

Spleen weight in the B2-24-4-5A·HCOOH-administered group was significantly lower than that in the saline-administered and HCQ-administered groups. Spleen cell count in the B2-24-4-5A·HCOOH-administered group was significantly lower than that in the saline-administered and HCQ-administered groups. As shown in FIGS. 11A and 11B, the B2-24-4-5A·HCOOH-administered group showed suppression of splenomegaly than the control saline-administered and HCQ-administered groups.

Example 18: Analysis of Spleen in NZBWF1 Mice Treated with B2-24-4-5A·HCOOH

Splenocytes were prepared by grinding the spleen obtained in Example 16 on a glass slide and stained with a labeled antibody. The labeled antibodies used were FITC-labeled anti-CD11b antibody, FITC-labeled anti-CD3 antibody, FITC-labeled anti-CD62L antibody, FITC-labeled anti-B220 antibody, FITC-labeled anti-CD71 antibody, PE-labeled anti-CD11c antibody, PE-labeled anti-Gr-1 antibody, PE-labeled anti-CD8 antibody, PE-labeled anti-CD44 antibody, PE-labeled anti-CD69 antibody, PE-labeled anti-CD21 antibody, PE-labeled anti-CD86 antibody, PE-labeled anti-Ter-119 antibody, PE-Cy7-labeled anti-CD23 antibody, APC-labeled anti-F4/80 antibody, APC-labeled anti-Ly-6G antibody, APC-labeled anti-CD4 antibody, APC-labeled anti-B220 antibody, APC-labeled anti-CD19 antibody, APC-labeled anti-CD11c antibody or APC-labeled anti-PDCA-1 antibody. 20 minutes later, the cells were washed with FACS buffer and suspended in 200 µL of FACS buffer containing 25 µg/mL 7-actinomycin D. The fluorescence intensity of the cells was analyzed by flow cytometry. Flow cytometry measurements were performed on a FACSCanto™ II (Becton Dickinson), and data were analyzed with FlowJo software (Tree Star) to calculate the percentage of various cells in the spleen. The results are shown in FIGS. 12(A)-(E), 13(A)-(E), and 14(A)-(E).

In the B2-24-4-5A·HCOOH group, compared to the saline-administered and HCQ-administered groups, an increase in the percentage of plasmacytoid dendritic cells, helper T cells, cytotoxic T cells and naive T cells, and a decrease in the percentage of neutrophils, erythroblasts, activated T cells, memory T cells and CD69 positive activated B cells were observed. Thus, the inflammatory pathology associated with the development of systemic lupus erythematosus was improved by the administration of B2-24-4-5A·HCOOH.

Example 19: Analysis of Micro RNA Stimulation on IFN-α Production

The inhibitory effect of B2-24-4-5A·HCOOH on TLR7-stimulated micro RNA in mouse Flt-3 ligand-induced dendritic cells (FLDC) was investigated. Mouse bone marrow cells were cultured in RPMI 1640 medium containing 100 ng/ml Flt-3 ligand, 10% (v/v) fetal calf serum (FCS), penicillin, streptomycin, L-glutamic acid, and 2-mercaptoethanol for 8 days at 37° C. in the presence of 5% (v/v) $CO_2$. Mouse FLDC induced to differentiate by culture were spread to $1.0 \times 10^5$ cells/100 µL. Then, 0.1, 0.3, or 1 µM of B2-24-4-5A·HCOOH was added thereto. 30 minutes after the addition of B2-24-4-5A·HCOOH, Vehicle or microRNA-cationic liposomal vehicle (DOTAP) complexes containing 0.5 or 2 µg/ml microRNA were added thereto. The microRNA sequences used are listed in Table 9.

TABLE 9

| Name | Sequence (5'-3') | SEQ ID |
| --- | --- | --- |
| miR21 | UAGCUUAUCAGACUGAUGUUGA | SEQ ID: 1 |
| miR574 | UGAGUGUGUGUGUGUGAGUGUGU | SEQ ID: 2 |
| let-7b | UGAGGUAGUAGGUUGUGUGGUU | SEQ ID: 3 |
| RNA40 | GCCCGUCUGUUGUGUGACUC | SEQ ID: 4 |

Figure 15:
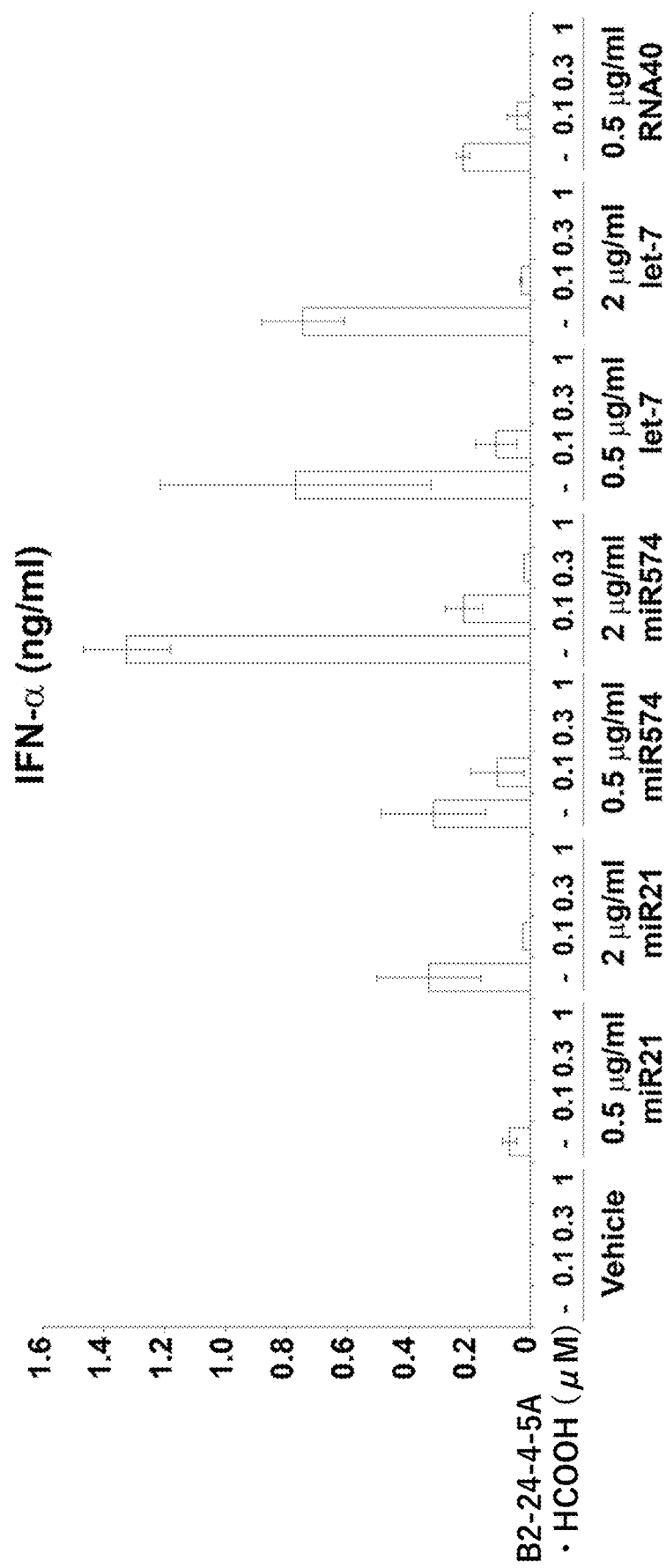
FIG. 15 shows a graph of the TLR7 inhibitory activity (suppression of IL-6 expression) of B2-24-4-5A·HCOOH in mouse Flt-3 ligand-induced dendritic cells (FLDC).

24 hours after the addition of the microRNA-DOTAP complex, the concentration of IFN-α in the medium was quantified using an ELISA method (used kit: Mouse IFN alpha Platinum ELISA (trade name), eBioscience). The results are shown in FIG. 15. As shown in FIG. 15, B2-24-4-5A·HCOOH inhibited micro RNA-stimulated IFN-α production in a concentration-dependent manner.

The invention claimed is:

1. A chemical compound represented by the following formula

[Chemical 1]

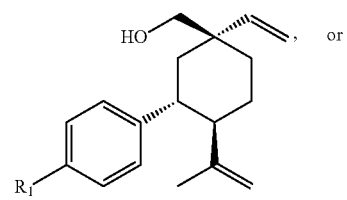

(I)

or

[Chemical 2]

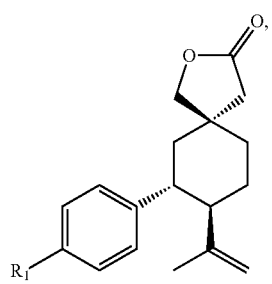

(II)

a pharmacologically acceptable salt thereof, or a prodrug thereof, wherein in formulae (I) and (II), $R_1$ is:

$C_{3-5}$ alkoxy group containing at least two oxygen atoms;

$C_{2-4}$ alkoxy group containing at least one hydroxyl group; and the following formula

[Chemical 3]

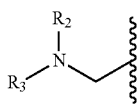

wherein $R_2$ and $R_3$ are each independently $C_{1-3}$ alkyl group; or

[Chemical 4]

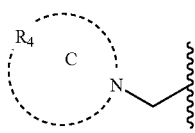

wherein C ring is a 3- to 7-membered nitrogen-containing heterocyclic ring, $R_4$ is a group represented by a combination of —NH—, —O—, —CF$_2$—, —CHF—, —C$_2$H$_2$F$_2$— or —CHF—X—CHF—, and X is $C_{1-4}$ alkyl group.

2. The chemical compound according to claim 1, the pharmacologically acceptable salt thereof, or the prodrug thereof, wherein $R_1$ is:

[Chemical 28]

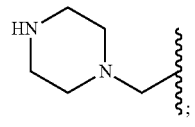

[Chemical 29]
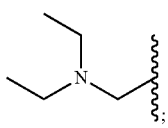
[Chemical 30]
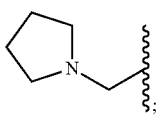
[Chemical 31]
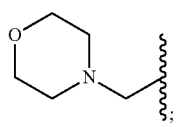
[Chemical 32]
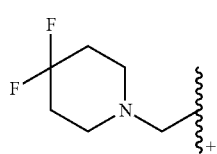
[Chemical 33]
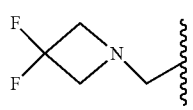
[Chemical 34]
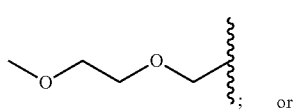
; or
[Chemical 35]
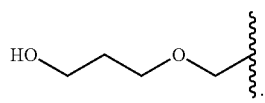
3. The compound according to claim 1, the pharmacologically acceptable salt thereof, or the prodrug thereof, wherein the chemical compound is represented by any of the following formulae:
[Chemical 13]
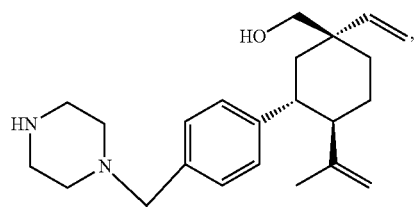
(III)
[Chemical 14]
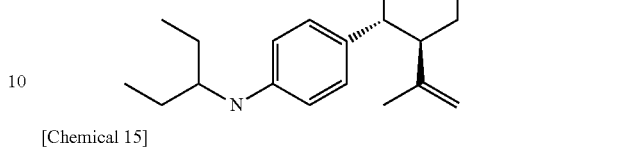
(IV)
[Chemical 15]
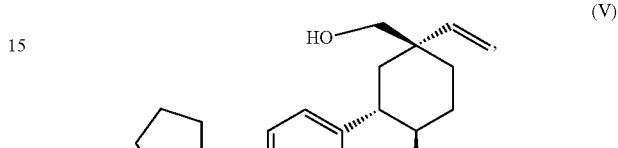
(V)
[Chemical 16]
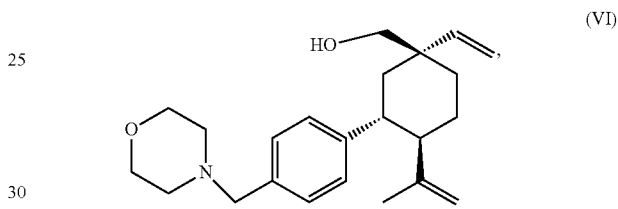
(VI)
[Chemical 17]
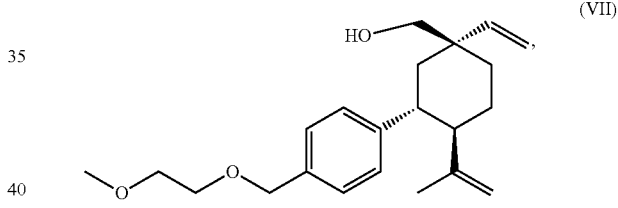
(VII)
[Chemical 18]
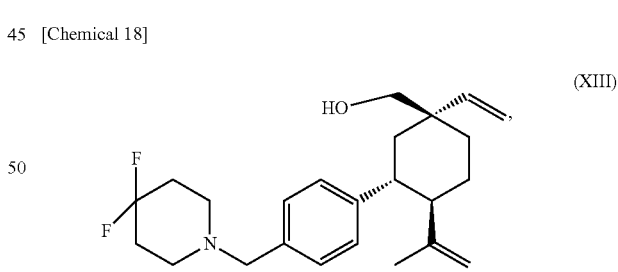
(XIII)
[Chemical 19]
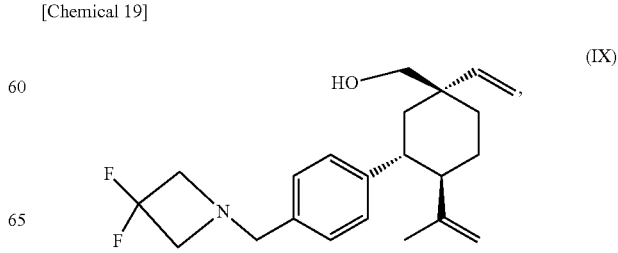
(IX)

-continued

[Chemical 20]

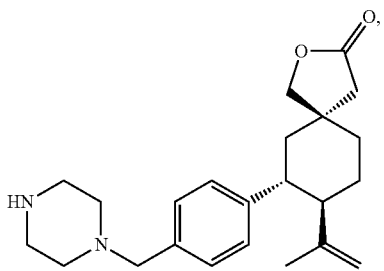

(X)

[Chemical 21]

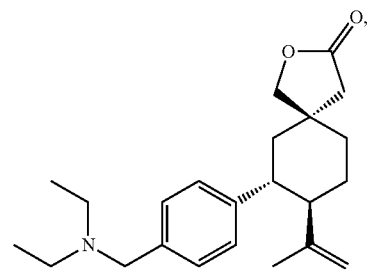

(XI)

[Chemical 22]

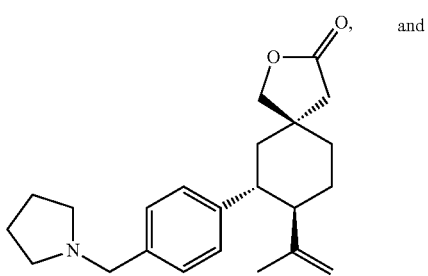

(XII) and

[Chemical 23]

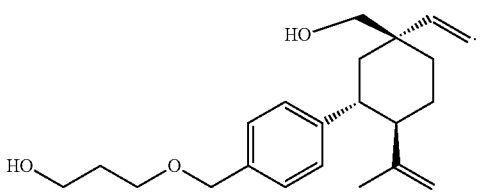

(XIII)

4. The chemical compound according to claim 1, the pharmacologically acceptable salt, or the prodrug thereof, wherein the pharmacologically acceptable salt is a hydrochloride salt or a formate salt.

5. A toll-like receptor 7 (TLR7) activation inhibitor comprising a chemical compound according to claim 1, a pharmacologically acceptable salt thereof, or a prodrug thereof.

6. The TLR7 activation inhibitor according to claim 5, comprising an inhibitory effect on production of NF-κB, IL-6, TNF-α or IFN-α due to activation of TLR7.

7. A method for treatment of a disease involving TLR7 activation in a subject, the method comprising administering an TLR7 activation inhibitor according to claim 5 to the subject, wherein the disease involving the TLR7 activation is an autoimmune disease, an autoinflammatory syndrome, autoimmune pancreatitis, atherosclerosis, sepsis, neurodegenerative disease, graft rejection, graft-versus-host disease, periodontal disease, viral immunodeficiency, IgA nephropathy, primary nephrotic syndrome, primary membranous proliferative glomerulonephritis, purpura nephritis, Langerhans cell histiocytosis, hemophagocytic lymphohistiocytosis, Rosai-Dorfman disease, obesity, type 2 diabetes mellitus or ulcerative colitis.

8. The method according to claim 7, wherein the disease involving the TLR7 activation is the autoimmune disease.

9. The method according to claim 7, wherein the autoimmune diseases is systemic lupus erythematosus, Sjogren syndrome, scleroderma, polymyositis/dermatomyositis, mixed connective tissue disease, duplication syndrome, antiphospholipid antibody syndrome, Behcet's disease, adult Still's disease, rheumatic fever, malignant rheumatoid arthritis, rheumatoid arthritis, juvenile rheumatoid arthritis, HLA-B27 related rheumatic diseases, IgG4-related syndrome, ANCA-related vasculitis, vasculitis syndrome, multiple sclerosis, psoriasis vulgaris, inflammatory bowel disease, autoimmune thyroid disease, autoimmune hemolytic anemia, idiopathic thrombocytopenia purpura, primary biliary cirrhosis, primary biliary cholangitis, myasthenia gravis, Goodpasture's syndrome, Guillain-Barre syndrome, chronic atrophic gastritis, rapidly progressive glomerulonephritis, anti-glomerular basement membrane nephritis, Addison's disease, type I diabetes mellitus, vitiligo vulgaris, pemphigus vulgaris, pemphigoid, autoimmune neutropenia, autoimmune hepatitis, or autoimmune pancreatitis.

10. The method according to claim 9, wherein the autoimmune disease is the systemic lupus erythematosus.

* * * * *